(12) United States Patent
Niespodziana et al.

(10) Patent No.: US 9,308,251 B2
(45) Date of Patent: Apr. 12, 2016

(54) PEPTIDE CARRIER FUSION PROTEINS AS ALLERGY VACCINES

(75) Inventors: Katarzyna Niespodziana, Vienna (AT); Margarete Focke-Tejkl, Vienna (AT); Susanne Vrtala, Vienna (AT); Srinita Banerjee, Vienna (AT); Kuan-Wei Chen, Vienna (AT); Milena Weber, Vienna (AT); Rudolf Valenta, Theresienfeld (AT); Katharina Marth, Vienna (AT)

(73) Assignee: BIOMAY AG, Vienna (AT)

( * ) Notice: Subject to any disclaimer, the term of this patent is extended or adjusted under 35 U.S.C. 154(b) by 0 days.

(21) Appl. No.: 14/124,925

(22) PCT Filed: Jun. 11, 2012

(86) PCT No.: PCT/EP2012/061040
§ 371 (c)(1),
(2), (4) Date: Dec. 9, 2013

(87) PCT Pub. No.: WO2012/168487
PCT Pub. Date: Dec. 13, 2012

(65) Prior Publication Data
US 2014/0193450 A1    Jul. 10, 2014

(30) Foreign Application Priority Data

Jun. 9, 2011    (EP) .................................... 11169365

(51) Int. Cl.
| | |
|---|---|
| *A61K 39/36* | (2006.01) |
| *C07K 14/005* | (2006.01) |
| *A61K 39/29* | (2006.01) |
| *C07K 14/415* | (2006.01) |
| *A61K 39/385* | (2006.01) |
| *A61K 39/12* | (2006.01) |
| *A61K 39/00* | (2006.01) |

(52) U.S. Cl.
CPC ............. *A61K 39/292* (2013.01); *A61K 39/12* (2013.01); *A61K 39/36* (2013.01); *A61K 39/385* (2013.01); *C07K 14/005* (2013.01); *C07K 14/415* (2013.01); *A61K 2039/53* (2013.01); *A61K 2039/57* (2013.01); *A61K 2039/6075* (2013.01); *A61K 2039/64* (2013.01); *A61K 2039/645* (2013.01); *C07K 2319/00* (2013.01); *C12N 2730/10122* (2013.01); *C12N 2730/10134* (2013.01)

(58) Field of Classification Search
None
See application file for complete search history.

(56) References Cited

U.S. PATENT DOCUMENTS

| | | |
|---|---|---|
| 8,258,275 B2 * | 9/2012 | Sallberg et al. .............. 536/23.1 |
| 2009/0324501 A1 | 12/2009 | Valenta et al. |
| 2012/0207788 A1 | 8/2012 | Valenta et al. |

FOREIGN PATENT DOCUMENTS

| | | |
|---|---|---|
| WO | WO 2007/140505 A2 | 12/2007 |
| WO | WO 2011/029869 A1 | 3/2011 |

OTHER PUBLICATIONS

Niespodziana et al. (Journal of Allergy and Clinical Immunology, Epub Mar. 16, 2011 in IDs on Mar. 6, 2014).*
International Search Report issued Oct. 8, 2012 in PCT/EP2012/061040.
Katarzyna Niespodziana, et al., "A hypoallergenic cat vaccine based on Fel d 1-derived peptides fused to hepatitis B PreS" Journal of Allergy and Clinical Immunology, vol. 127, No. 6, XP55014054, Jun. 1, 2011, pp. 1562-1570.
Rudolf Valenta, et al., "Recombinant allergens: What does the future hold?" Journal of Allergy and Clinical Immunology, vol. 127, No. 4, XP55014092, Apr. 1, 2011, pp. 860-864.
Johanna Edlmayr, et al., "Allergen-Specific Immunotherapy: Towards Combination Vaccines for Allergic and Infectious Diseases" Current Topics on Microbiology and Immunology, vol. 352, XP009158072, Jan. 1, 2011, pp. 121-140.
Johanna Edlmayr, et al., "A Combination Vaccine for Allergy and Rhinovirus Infections Based on Rhinovirus-Derived Surface Protein VP1 and a Nonallergenic Peptide of the Major Timothy Grass Pollen Allergen Phl p 1" Journal of Immunology, vol. 182, No. 10, XP002602736, May 1, 2009, pp. 6298-6306.
M. Focke, et al., "Developments in allergen-specific immunotherapy: from allergen extracts to allergy vaccines bypassing allergen-specific immunoglobulin E and T cell reactivity" Clinical and Experimental Allergy, vol. 40, No. 3, XP55014313, Mar. 1, 2010, pp. 385-397.
M. Focke, et al., "Non-anaphylactic surface-exposed peptides of the major birch pollen allergen, Bet v 1, for preventive vaccination" Clinical and Experimental Allergy, vol. 34, No. 10, XP002657544, Oct. 1, 2004, pp. 1525-1533.
Teresa E. Twaroch, et al., "Carrier-bound, nonallergenic Ole e 1 peptides for vaccination against olive pollen allergy" Journal of Allergy and Clinical Immunology, vol. 128, No. 1, XP55014321, Apr. 21, 2011, pp. 178-184.

(Continued)

*Primary Examiner* — Agnieszka Boesen
(74) *Attorney, Agent, or Firm* — Oblon, McClelland, Maier & Neustadt, L.L.P.

(57) ABSTRACT

The present invention relates to a polypeptide comprising at least three peptide fragments consisting of 10 to 50 consecutive amino acid residues of at least one wild-type allergen fused to the N- and C-terminus of a surface polypeptide of a virus of the hepadnaviridae family or at least one fragment of said surface polypeptide.

17 Claims, 25 Drawing Sheets

(56) References Cited

OTHER PUBLICATIONS

Nadine Mothes-Luksch, et al., "Disruption of Allergenic Activity of the Major Grass Pollen Allergen Phl p 2 by Reassembly as a Mosaic Protein" The Journal of Immunology, vol. 181, No. 7, XP002583817, Oct. 1, 2008, pp. 4864-4873.

K.-W. Chen, et al., "Carrier-bound nonallergenic Der p 2 peptides induce IgG antibodies blocking allergen-induced basophil activation in allergic patients" Allergy, European Journal of Allergy and Clinical immunology, vol. 67, No. 5, XP55039011, May 1, 2012, pp. 609-621.

* cited by examiner

Plasmid Map:

Plasmid Map:

```
  1 M VRYTTEGGT KTEAEDVIPE GWKADTSYES KVRYTTEGGT KTEAEDVIPE GWKADTSYES
 61 KGGWSSKPRK GMGTNLSVPN PLGFFPDHQL DPAFGANSNN PDWDFNPIKD HWPAANQVGV
121 GAFGPGLTPP HGGILGWSPQ AQGILTTVST IPPPASTNRQ SGRQPTPISP PLRDSHPQAM
181 QWNSTAFHQA LQDPRVRGLY FPAGGSSSGT VNPAPNIASH ISSISARTGD PVTNVRYTTE
241 GGTKTEAEDV IPEGWKADTS YESKVRYTTE GGTKTEAEDV IPEGWKADTS YESK
```

Fig. 2 A

```
  1 MFRFLTEKGM KNVFDDVVPE KYTIGATYAP EEFRFLTEKG MKNVFDDVVP EKYTIGATYA
 61 PEEGGWSSKP RKGMTNLSV PNPLGFFPDH QLDPAFGANS NNPDWDFNPI KDHWPAANQV
121 GVGAFGPGLT PPHGGILGWS PQAQGILTTV STIPPPASTN RQSGRQPTPI SPPLRDSHPQ
181 AMQWNSTAFH QALQDPRVRG LYFPAGGSSS GTVNPAPNIA SHISSISART GDPVTNFRFL
241 TEKGMKNVFD DVVPEKYTIG ATYAPEEFRF LTEKGMKNVF DDVVPEKYTI GATYAPEE
```

Fig. 2 B

```
  1 MEAAFNDAIK ASTGGAYESY KFIPALEAAV KAEEVKVIPA GELQVIEKVD AAFKVAATAA
 61 NAAPANDKGG WSSKPRKGMG TNLSVPNPLG FFPDHQLDPA FGANSNNPDW DFNPIKDHWP
121 AANQVGVGAF GPGLTPPHGG ILGWSPQAQG ILTTVSTIPP PASTNRQSGR QPTPISPPLR
181 DSHPQAMQWN STAFHQALQD PRVRGLYFPA GGSSSGTVNP APNIASHISS ISARTGDPVT
241 NADLGYGPAT PAAPAAGYTP ATPAAPAEAA PAGKATTEEQ KLIEKINAGF KAALAAAAGV
301 QPADKYR.
```

Fig 2 C

```
  1 GKATTEEQKL IEDVNASFRA AMATTANVPP ADKGKATTEE QKLIEDVNAS FRAAMATTAN
 61 VPPADKGGWS SKPRKGMGTN LSVPNPLGFF PDHQLDPAFG ANSNNPDWDF NPIKDHWPAA
121 NQVGVGAFGP GLTPPHGGIL GWSPQAQGIL TTVSTIPPPA STNRQSGRQP TPISPPLRDS
181 HPQAMQWNST AFHQALQDPR VRGLYFPAGG SSSGTVNPAP NIASHISSIS ARTGDPVTNG
241 KATTEEQKLI EDVNASFRAA MATTANVPPA DKGKATTEEQ KLIEDVNASF RAAMATTANV
301 PPADK
```

Fig. 2 D

```
  1 LFPKVAPQA ISSVENIEGN GGPGTIKKIS FPEGPFKYVK DRVDELFPKV APQAISSVEN
 61 IEGNGGPGTI KKISPEGPFK YVKDRVDEGG WSSKPRKGMG TNLSVPNPLG FFPDHQLDPA
121 FGANSNNPDW DFNPIKDHWP AANQVGVGAF GPGLTPPHGG ILGWSPQAQG ILTTVSTIPP
181 PASTNRQSGR QPTPISPPLR DSHPQAMQWN STAFHQALQD PRVRGLYFPA GGSSSGTVNP
241 APNIASHISS ISARTGDPVT NLFPKVAPQA ISSVENIEGN GGPGTIKKIS PEGPFKYVKD
301 RVDELFPKVA PQAISSVENI EGNGGPGTIK KISPEGPFKY VKDRVDE
```

Fig 2 E

```
  1 LFPKVAPQA ISSVENIEGN GGPGTIKKIS FPEGPFKYVK DRVDELFPKV APQAISSVEN
 61 IEGNGGPGTI KKISPEGPFK YVKDRVDEGG WSSKPRKGMG TNLSVPNPLG FFPDHQLDPA
121 FGANSNNPDW DFNPIKDHWP AANQVGVGAF GPGLTPPHGG ILGWSPQAQG ILTTVSTIPP
181 PASTNRQSGR QPTPISPPLR DSHPQAMQWN STAFHQALQD PRVRGLYFPA GGSSSGTVNP
241 APNIASHISS ISARTGDPVT NPEGFPFKYV DRVDEVDHTN FKYNYSVIEG GPIGDTLEKI
301 SNEIKIPEGF PFKYVDRVDE DHTNFKYNYS VIEGGPIGDT LEKISNEIKI
```

Fig 2 F

```
  1 MADLGYGPAT PAAPAAGYTP ATPAAPAEAA PAGKATTEEQ KLIEKINAGF KAALAAAAGV
 61 QPADKYRGGW SSKPRKGMGT NLSVPNPLGF FPDHQLDPAF GANSNNPDWD FNPIKDHWPA
121 ANQVGVGAFG PGLTPPHGGI LGWSPQAQGI LTTVSTIPPP ASTNRQSGRQ PTPISPPLRD
181 SHPQAMQWNS TAFHQALQDP RVRGLYFPAG GSSSGTVNPA PNIASHISSI SARTGDPVTN
241 EAAFNDAIKA STGGAYESYK FIPALEAAVK AEEVKVIPAG ELQVIEKVDA AFKVAATAAN
301 AAPANDK
```

Fig 2 G

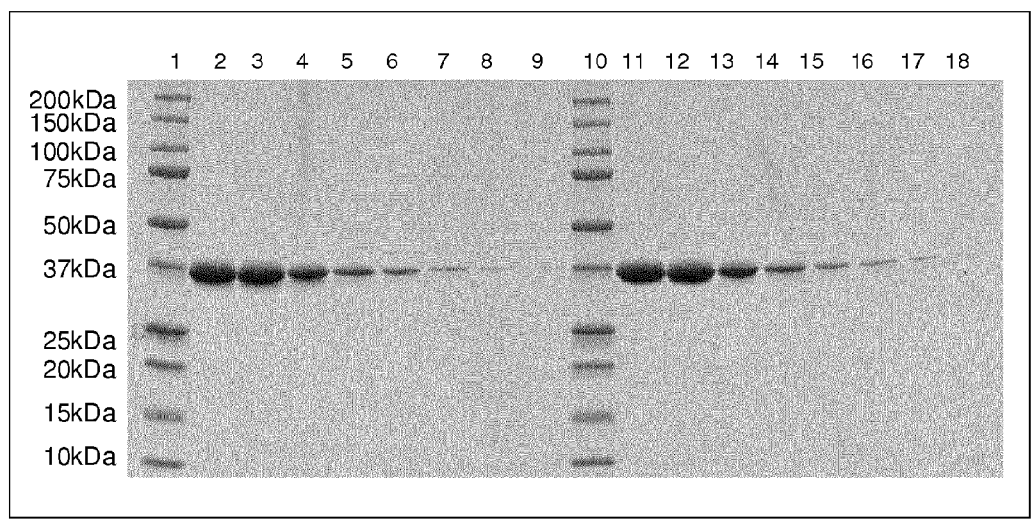

Fig. 3 A

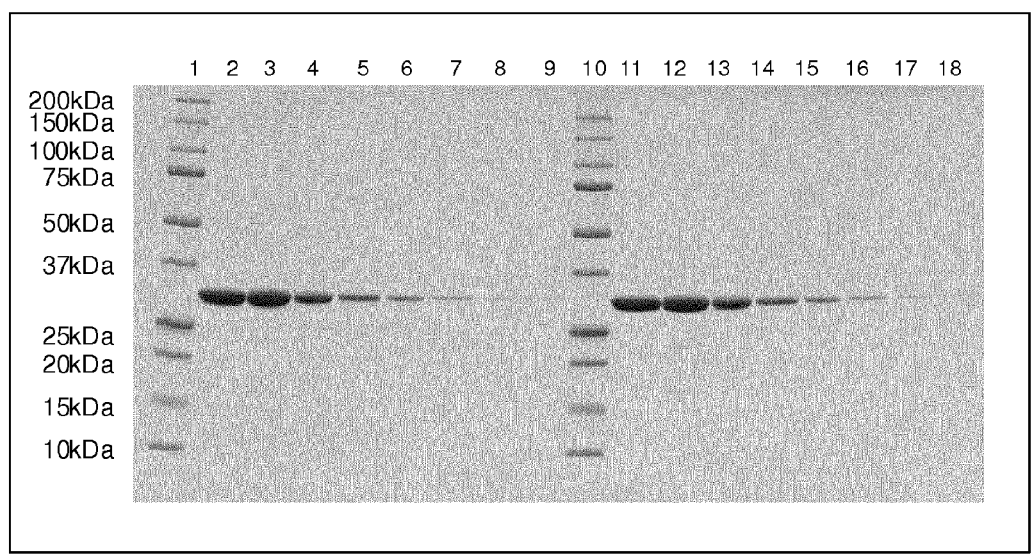

Fig. 3 B

HBV Der p2-2xP2-2xP4

HGSEPCIIHRGKPFQLEAVFEANQNSKTAK*HGSEPCIIHRGKPFQLEAVFEANQNSKTAK*GG
WSSKPRKGMGTNLSVPNPLGFFPDHQLDPAFGANSNNPDWDFNPIKDHWPAANQVGVGAFGP
GLTPPHGGILGWSPQAQGILTTVSTIPPPASTNRQSGRQPTPISPPLRDSHPQAMQWNSTAF
HQALQDPRVRGLYFPAGGSSSGTVNPAPNIASHISSISARTGDPVTNEVDVPGIDPNACHYM
KCPLVKGQQYDIKYTWIVPKIAPKSEN*EVDVPGIDPNACHYMKCPLVKGQQYDIKYTWIVPK
IAPKSEN*

Fig. 18A

HBV Der p2-3xP2-3xP4

HGSEPCIIHRGKPFQLEAVFEANQNSKTAK*HGSEPCIIHRGKPFQLEAVFEANQNSKTAK*HG
SEPCIIHRGKPFQLEAVFEANQNSKTAKGGWSSKPRKGMGTNLSVPNPLGFFPDHQLDPAFG
ANSNNPDWDFNPIKDHWPAANQVGVGAFGPGLTPPHGGILGWSPQAQGILTTVSTIPPPAST
NRQSGRQPTPISPPLRDSHPQAMQWNSTAFHQALQDPRVRGLYFPAGGSSSGTVNPAPNIAS
HISSISARTGDPVTNEVDVPGIDPNACHYMKCPLVKGQQYDIKYTWIVPKIAPKSEN*EVDVP
GIDPNACHYMKCPLVKGQQYDIKYTWIVPKIAPKSEN*EVDVPGIDPNACHYMKCPLVKGQQY
DIKYTWIVPKIAPKSEN

Fig. 18B

HBV Der p23-2xP4-2xP5

GYFADPKDPHKFYICSNWEAVHKDCPGNTGYFADPKDPHKFYICSNWEAVHKDCPGNTGGWS
SKPRKGMGTNLSVPNPLGFFPDHQLDPAFGANSNNPDWDFNPIKDHWPAANQVGVGAFGPGL
TPPHGGILGWSPQAQGILTTVSTIPPPASTNRQSGRQPTPISPPLRDSHPQAMQWNSTAFHQ
ALQDPRVRGLYFPAGGSSSGTVNPAPNIASHISSISARTGDPVTNKFYICSNWEAVHKDCPG
NTRWNEDEETCTKFYICSNWEAVHKDCPGNTRWNEDEETCT

Fig. 18C

HBV Der p23-4xP6

GYFADPKDPHKFYISSNWEAVHKDSPGNTRWNEDEETST*GYFADPKDPHKFYISSNWEAVHK*
*DSPGNTRWNEDEETST*GGWSSKPRKGMGTNLSVPNPLGFFPDHQLDPAFGANSNNPDWDFNP
IKDHWPAANQVGVGAFGPGLTPPHGGILGWSPQAQGILTTVSTIPPPASTNRQSGRQPTPIS
PPLRDSHPQAMQWNSTAFHQALQDPRVRGLYFPAGGSSSGTVNPAPNIASHISSISARTGDP
VTNGYFADPKDPHKFYISSNWEAVHKDSPGNTRWNEDEETST*GYFADPKDPHKFYISSNWEA*
*VHKDSPGNTRWNEDEETST*

Fig. 18D

Columns 1-26: individual house dust mite allergic patient´s sera
NA: serum from non allergic individual
BC: buffer control

SEQUENCE LISTING

<160> NUMBER OF SEQ ID NOS: 152

<210> SEQ ID NO 1
<211> LENGTH: 28
<212> TYPE: PRT
<213> ORGANISM: Artificial Sequence
<220> FEATURE:
<223> OTHER INFORMATION: Synthetic Peptide

```
<400> SEQUENCE: 1

His Val Glu Lys Gly Ser Asn Pro Asn Tyr Leu Ala Leu Leu Val Lys
1               5                   10                  15

Tyr Val Asn Gly Asp Gly Asp Val Val Ala Val Cys
            20                  25

<210> SEQ ID NO 2
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 2

Glu Pro Val Val Val His Ile Thr Asp Asp Asn Glu Glu Pro Ile Ala
1               5                   10                  15

Pro Tyr His Phe Asp Leu Ser Gly His Ala Phe Gly Ala Met Ala Cys
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 3

Ile Pro Lys Val Pro Pro Gly Pro Asn Ile Thr Ala Thr Tyr Gly Asp
1               5                   10                  15

Lys Trp Leu Asp Ala Lys Ser Thr Trp Tyr Gly Lys Pro Thr Gly Cys
            20                  25                  30

<210> SEQ ID NO 4
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 4

Gly Tyr Lys Asp Val Asp Lys Pro Pro Phe Ser Gly Met Thr Gly Cys
1               5                   10                  15

Gly Asn Thr Pro Ile Phe Lys Ser Gly Arg Gly Cys
            20                  25

<210> SEQ ID NO 5
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 5

Cys Val Arg Tyr Thr Thr Glu Gly Gly Thr Lys Thr Glu Ala Glu Asp
1               5                   10                  15

Val Ile Pro Glu Gly Trp Lys Ala Asp Thr Ser Tyr Glu Ser Lys
            20                  25                  30

<210> SEQ ID NO 6
<211> LENGTH: 34
<212> TYPE: PRT
<213> ORGANISM: Artificial Sequence
<220> FEATURE:
<223> OTHER INFORMATION: Synthetic Peptide
```

```
<400> SEQUENCE: 6

Val Pro Lys Val Thr Phe Thr Val Glu Lys Gly Ser Asn Glu Lys His
1               5                   10                  15

Leu Ala Val Leu Val Lys Tyr Glu Gly Asp Thr Met Ala Glu Val Glu
            20                  25                  30

Leu Cys

<210> SEQ ID NO 7
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 7

Cys Val Glu Lys Gly Ser Asn Glu Lys His Leu Ala Val Leu Val Lys
1               5                   10                  15

Tyr Glu Gly Asp Thr Met Ala Glu Val Glu Leu Arg Glu His Gly Ser
            20                  25                  30

Asp

<210> SEQ ID NO 8
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 8

Arg Glu His Gly Ser Asp Glu Trp Val Ala Met Thr Lys Gly Glu Gly
1               5                   10                  15

Gly Val Trp Thr Phe Asp Ser Glu Glu Pro Leu Gln Gly Pro Phe Asn
            20                  25                  30

Cys

<210> SEQ ID NO 9
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 9

Cys Phe Arg Phe Leu Thr Glu Lys Gly Met Lys Asn Val Phe Asp Asp
1               5                   10                  15

Val Val Pro Glu Lys Tyr Thr Ile Gly Ala Thr Tyr Ala Pro Glu Glu
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 10

Gly Lys Ala Thr Thr Glu Glu Gln Lys Leu Ile Glu Asp Val Asn Ala
1               5                   10                  15

Ser Phe Arg Ala Ala Met Ala Thr Thr Ala Asn Val Pro Pro Ala Asp
            20                  25                  30
```

<210> SEQ ID NO 11
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 11

```
Tyr Lys Thr Phe Glu Ala Ala Phe Thr Val Ser Ser Lys Arg Asn Leu
1               5                   10                  15

Ala Asp Ala Val Ser Lys Ala Pro Gln Leu Val Pro Lys Leu Asp Glu
            20                  25                  30

Val Tyr Asn
        35
```

<210> SEQ ID NO 12
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 12

```
Ala Ala Asp His Ala Ala Pro Glu Asp Lys Tyr Glu Ala Phe Val Leu
1               5                   10                  15

His Phe Ser Glu Ala Leu Arg Ile Ile Ala Gly Thr Pro Glu Val His
            20                  25                  30

Ala
```

<210> SEQ ID NO 13
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 13

```
Asp Ala Val Ser Lys Ala Pro Gln Leu Val Pro Lys Leu Asp Glu Val
1               5                   10                  15

Tyr Asn Ala Ala Tyr Asn Ala Ala Asp His Ala Ala Pro Glu Asp Lys
            20                  25                  30

Tyr
```

<210> SEQ ID NO 14
<211> LENGTH: 294
<212> TYPE: PRT
<213> ORGANISM: Artificial Sequence
<220> FEATURE:
<223> OTHER INFORMATION: Synthetic Peptide

<400> SEQUENCE: 14

```
Met Val Arg Tyr Thr Thr Glu Gly Gly Thr Lys Thr Glu Ala Glu Asp
1               5                   10                  15

Val Ile Pro Glu Gly Trp Lys Ala Asp Thr Ser Tyr Glu Ser Lys Val
            20                  25                  30

Arg Tyr Thr Thr Glu Gly Gly Thr Lys Thr Glu Ala Glu Asp Val Ile
            35                  40                  45

Pro Glu Gly Trp Lys Ala Asp Thr Ser Tyr Glu Ser Lys Gly Gly Trp
        50                  55                  60

Ser Ser Lys Pro Arg Lys Gly Met Gly Thr Asn Leu Ser Val Pro Asn
65                  70                  75                  80
```

```
Pro Leu Gly Phe Phe Pro Asp His Gln Leu Asp Pro Ala Phe Gly Ala
                85                  90                  95
Asn Ser Asn Asn Pro Asp Trp Asp Phe Asn Pro Ile Lys Asp His Trp
            100                 105                 110
Pro Ala Ala Asn Gln Val Gly Val Gly Ala Phe Gly Pro Gly Leu Thr
        115                 120                 125
Pro Pro His Gly Gly Ile Leu Gly Trp Ser Pro Gln Ala Gln Gly Ile
    130                 135                 140
Leu Thr Thr Val Ser Thr Ile Pro Pro Ala Ser Thr Asn Arg Gln
145                 150                 155                 160
Ser Gly Arg Gln Pro Thr Pro Ile Ser Pro Leu Arg Asp Ser His
                165                 170                 175
Pro Gln Ala Met Gln Trp Asn Ser Thr Ala Phe His Gln Ala Leu Gln
            180                 185                 190
Asp Pro Arg Val Arg Gly Leu Tyr Phe Pro Ala Gly Gly Ser Ser Ser
        195                 200                 205
Gly Thr Val Asn Pro Ala Pro Asn Ile Ala Ser His Ile Ser Ser Ile
    210                 215                 220
Ser Ala Arg Thr Gly Asp Pro Val Thr Asn Val Arg Tyr Thr Thr Glu
225                 230                 235                 240
Gly Gly Thr Lys Thr Glu Ala Glu Asp Val Ile Pro Glu Gly Trp Lys
                245                 250                 255
Ala Asp Thr Ser Tyr Glu Ser Lys Val Arg Tyr Thr Thr Glu Gly Gly
            260                 265                 270
Thr Lys Thr Glu Ala Glu Asp Val Ile Pro Glu Gly Trp Lys Ala Asp
        275                 280                 285
Thr Ser Tyr Glu Ser Lys
    290

<210> SEQ ID NO 15
<211> LENGTH: 298
<212> TYPE: PRT
<213> ORGANISM: Artificial Sequence
<220> FEATURE:
<223> OTHER INFORMATION: Synthetic Peptide

<400> SEQUENCE: 15

Met Phe Arg Phe Leu Thr Glu Lys Gly Met Lys Asn Val Phe Asp Asp
1               5                   10                  15
Val Val Pro Glu Lys Tyr Thr Ile Gly Ala Thr Tyr Ala Pro Glu Glu
            20                  25                  30
Phe Arg Phe Leu Thr Glu Lys Gly Met Lys Asn Val Phe Asp Asp Val
        35                  40                  45
Val Pro Glu Lys Tyr Thr Ile Gly Ala Thr Tyr Ala Pro Glu Glu Gly
    50                  55                  60
Gly Trp Ser Ser Lys Pro Arg Lys Gly Met Gly Thr Asn Leu Ser Val
65                  70                  75                  80
Pro Asn Pro Leu Gly Phe Phe Pro Asp His Gln Leu Asp Pro Ala Phe
                85                  90                  95
Gly Ala Asn Ser Asn Asn Pro Asp Trp Asp Phe Asn Pro Ile Lys Asp
            100                 105                 110
His Trp Pro Ala Ala Asn Gln Val Gly Val Gly Ala Phe Gly Pro Gly
        115                 120                 125
Leu Thr Pro Pro His Gly Gly Ile Leu Gly Trp Ser Pro Gln Ala Gln
    130                 135                 140
```

```
Gly Ile Leu Thr Thr Val Ser Thr Ile Pro Pro Ala Ser Thr Asn
145                 150                 155                 160

Arg Gln Ser Gly Arg Gln Pro Thr Pro Ile Ser Pro Pro Leu Arg Asp
            165                 170                 175

Ser His Pro Gln Ala Met Gln Trp Asn Ser Thr Ala Phe His Gln Ala
        180                 185                 190

Leu Gln Asp Pro Arg Val Arg Gly Leu Tyr Phe Pro Ala Gly Gly Ser
            195                 200                 205

Ser Ser Gly Thr Val Asn Pro Ala Pro Asn Ile Ala Ser His Ile Ser
210                 215                 220

Ser Ile Ser Ala Arg Thr Gly Asp Pro Val Thr Asn Phe Arg Phe Leu
225                 230                 235                 240

Thr Glu Lys Gly Met Lys Asn Val Phe Asp Asp Val Val Pro Glu Lys
                245                 250                 255

Tyr Thr Ile Gly Ala Thr Tyr Ala Pro Glu Glu Phe Arg Phe Leu Thr
            260                 265                 270

Glu Lys Gly Met Lys Asn Val Phe Asp Asp Val Val Pro Glu Lys Tyr
        275                 280                 285

Thr Ile Gly Ala Thr Tyr Ala Pro Glu Glu
    290                 295

<210> SEQ ID NO 16
<211> LENGTH: 307
<212> TYPE: PRT
<213> ORGANISM: Artificial Sequence
<220> FEATURE:
<223> OTHER INFORMATION: Synthetic Peptide

<400> SEQUENCE: 16

Met Glu Ala Ala Phe Asn Asp Ala Ile Lys Ala Ser Thr Gly Gly Ala
1               5                   10                  15

Tyr Glu Ser Tyr Lys Phe Ile Pro Ala Leu Glu Ala Val Lys Ala
            20                  25                  30

Glu Glu Val Lys Val Ile Pro Ala Gly Glu Leu Gln Val Ile Glu Lys
            35                  40                  45

Val Asp Ala Ala Phe Lys Val Ala Ala Thr Ala Ala Asn Ala Ala Pro
50                  55                  60

Ala Asn Asp Lys Gly Gly Trp Ser Ser Lys Pro Arg Lys Gly Met Gly
65                  70                  75                  80

Thr Asn Leu Ser Val Pro Asn Pro Leu Gly Phe Phe Pro Asp His Gln
            85                  90                  95

Leu Asp Pro Ala Phe Gly Ala Asn Ser Asn Asn Pro Asp Trp Asp Phe
        100                 105                 110

Asn Pro Ile Lys Asp His Trp Pro Ala Ala Asn Gln Val Gly Val Gly
            115                 120                 125

Ala Phe Gly Pro Gly Leu Thr Pro Pro His Gly Gly Ile Leu Gly Trp
        130                 135                 140

Ser Pro Gln Ala Gln Gly Ile Leu Thr Thr Val Ser Thr Ile Pro Pro
145                 150                 155                 160

Pro Ala Ser Thr Asn Arg Gln Ser Gly Arg Gln Pro Thr Pro Ile Ser
                165                 170                 175

Pro Pro Leu Arg Asp Ser His Pro Gln Ala Met Gln Trp Asn Ser Thr
            180                 185                 190

Ala Phe His Gln Ala Leu Gln Asp Pro Arg Val Arg Gly Leu Tyr Phe
        195                 200                 205
```

```
Pro Ala Gly Gly Ser Ser Gly Thr Val Asn Pro Ala Pro Asn Ile
        210                 215                 220

Ala Ser His Ile Ser Ser Ile Ser Ala Arg Thr Gly Asp Pro Val Thr
225                 230                 235                 240

Asn Ala Asp Leu Gly Tyr Gly Pro Ala Thr Pro Ala Ala Pro Ala Ala
                245                 250                 255

Gly Tyr Thr Pro Ala Thr Pro Ala Ala Pro Ala Glu Ala Ala Pro Ala
                260                 265                 270

Gly Lys Ala Thr Thr Glu Glu Gln Lys Leu Ile Glu Lys Ile Asn Ala
                275                 280                 285

Gly Phe Lys Ala Ala Leu Ala Ala Ala Ala Gly Val Gln Pro Ala Asp
                290                 295                 300

Lys Tyr Arg
305

<210> SEQ ID NO 17
<211> LENGTH: 305
<212> TYPE: PRT
<213> ORGANISM: Artificial Sequence
<220> FEATURE:
<223> OTHER INFORMATION: Synthetic Peptide

<400> SEQUENCE: 17

Gly Lys Ala Thr Thr Glu Glu Gln Lys Leu Ile Glu Asp Val Asn Ala
1               5                   10                  15

Ser Phe Arg Ala Ala Met Ala Thr Thr Ala Asn Val Pro Pro Ala Asp
                20                  25                  30

Lys Gly Lys Ala Thr Thr Glu Glu Gln Lys Leu Ile Glu Asp Val Asn
                35                  40                  45

Ala Ser Phe Arg Ala Ala Met Ala Thr Thr Ala Asn Val Pro Pro Ala
50                  55                  60

Asp Lys Gly Gly Trp Ser Ser Lys Pro Arg Lys Gly Met Gly Thr Asn
65                  70                  75                  80

Leu Ser Val Pro Asn Pro Leu Gly Phe Phe Pro Asp His Gln Leu Asp
                85                  90                  95

Pro Ala Phe Gly Ala Asn Ser Asn Asn Pro Asp Trp Asp Phe Asn Pro
                100                 105                 110

Ile Lys Asp His Trp Pro Ala Ala Asn Gln Val Gly Val Gly Ala Phe
                115                 120                 125

Gly Pro Gly Leu Thr Pro Pro His Gly Gly Ile Leu Gly Trp Ser Pro
                130                 135                 140

Gln Ala Gln Gly Ile Leu Thr Thr Val Ser Thr Ile Pro Pro Pro Ala
145                 150                 155                 160

Ser Thr Asn Arg Gln Ser Gly Arg Gln Pro Thr Pro Ile Ser Pro Pro
                165                 170                 175

Leu Arg Asp Ser His Pro Gln Ala Met Gln Trp Asn Ser Thr Ala Phe
                180                 185                 190

His Gln Ala Leu Gln Asp Pro Arg Val Arg Gly Leu Tyr Phe Pro Ala
                195                 200                 205

Gly Gly Ser Ser Ser Gly Thr Val Asn Pro Ala Pro Asn Ile Ala Ser
                210                 215                 220

His Ile Ser Ser Ile Ser Ala Arg Thr Gly Asp Pro Val Thr Asn Gly
225                 230                 235                 240

Lys Ala Thr Thr Glu Glu Gln Lys Leu Ile Glu Asp Val Asn Ala Ser
                245                 250                 255
```

```
Phe Arg Ala Ala Met Ala Thr Thr Ala Asn Val Pro Pro Ala Asp Lys
            260                 265                 270

Gly Lys Ala Thr Thr Glu Glu Gln Lys Leu Ile Glu Asp Val Asn Ala
            275                 280                 285

Ser Phe Arg Ala Ala Met Ala Thr Thr Ala Asn Val Pro Pro Ala Asp
            290                 295                 300

Lys
305

<210> SEQ ID NO 18
<211> LENGTH: 346
<212> TYPE: PRT
<213> ORGANISM: Artificial Sequence
<220> FEATURE:
<223> OTHER INFORMATION: Synthetic Peptide

<400> SEQUENCE: 18

Leu Phe Pro Lys Val Ala Pro Gln Ala Ile Ser Ser Val Glu Asn Ile
1               5                   10                  15

Glu Gly Asn Gly Gly Pro Gly Thr Ile Lys Lys Ile Ser Phe Pro Glu
            20                  25                  30

Gly Pro Phe Lys Tyr Val Lys Asp Arg Val Asp Glu Leu Phe Pro Lys
            35                  40                  45

Val Ala Pro Gln Ala Ile Ser Ser Val Glu Asn Ile Glu Gly Asn Gly
50                  55                  60

Gly Pro Gly Thr Ile Lys Lys Ile Ser Pro Glu Gly Pro Phe Lys Tyr
65                  70                  75                  80

Val Lys Asp Arg Val Asp Glu Gly Gly Trp Ser Ser Lys Pro Arg Lys
            85                  90                  95

Gly Met Gly Thr Asn Leu Ser Val Pro Asn Pro Leu Gly Phe Phe Pro
            100                 105                 110

Asp His Gln Leu Asp Pro Ala Phe Gly Ala Asn Ser Asn Asn Pro Asp
            115                 120                 125

Trp Asp Phe Asn Pro Ile Lys Asp His Trp Pro Ala Ala Asn Gln Val
130                 135                 140

Gly Val Gly Ala Phe Gly Pro Gly Leu Thr Pro Pro His Gly Gly Ile
145                 150                 155                 160

Leu Gly Trp Ser Pro Gln Ala Gln Gly Ile Leu Thr Thr Val Ser Thr
            165                 170                 175

Ile Pro Pro Pro Ala Ser Thr Asn Arg Gln Ser Gly Arg Gln Pro Thr
            180                 185                 190

Pro Ile Ser Pro Pro Leu Arg Asp Ser His Pro Gln Ala Met Gln Trp
            195                 200                 205

Asn Ser Thr Ala Phe His Gln Ala Leu Gln Asp Pro Arg Val Arg Gly
            210                 215                 220

Leu Tyr Phe Pro Ala Gly Gly Ser Ser Ser Gly Thr Val Asn Pro Ala
225                 230                 235                 240

Pro Asn Ile Ala Ser His Ile Ser Ser Ile Ser Ala Arg Thr Gly Asp
            245                 250                 255

Pro Val Thr Asn Leu Phe Pro Lys Val Ala Pro Gln Ala Ile Ser Ser
            260                 265                 270

Val Glu Asn Ile Glu Gly Asn Gly Gly Pro Gly Thr Ile Lys Lys Ile
            275                 280                 285

Ser Pro Glu Gly Pro Phe Lys Tyr Val Lys Asp Arg Val Asp Glu Leu
            290                 295                 300
```

```
Phe Pro Lys Val Ala Pro Gln Ala Ile Ser Ser Val Glu Asn Ile Glu
305                 310                 315                 320

Gly Asn Gly Gly Pro Gly Thr Ile Lys Lys Ile Ser Pro Glu Gly Pro
                325                 330                 335

Phe Lys Tyr Val Lys Asp Arg Val Asp Glu
            340                 345
```

<210> SEQ ID NO 19
<211> LENGTH: 349
<212> TYPE: PRT
<213> ORGANISM: Artificial Sequence
<220> FEATURE:
<223> OTHER INFORMATION: Synthetic Peptide

<400> SEQUENCE: 19

```
Leu Phe Pro Lys Val Ala Pro Gln Ala Ile Ser Ser Val Glu Asn Ile
1               5                   10                  15

Glu Gly Asn Gly Gly Pro Gly Thr Ile Lys Lys Ile Ser Phe Pro Glu
            20                  25                  30

Gly Pro Phe Lys Tyr Val Lys Asp Arg Val Asp Glu Leu Phe Pro Lys
        35                  40                  45

Val Ala Pro Gln Ala Ile Ser Ser Val Glu Asn Ile Glu Gly Asn Gly
    50                  55                  60

Gly Pro Gly Thr Ile Lys Lys Ile Ser Pro Glu Gly Pro Phe Lys Tyr
65                  70                  75                  80

Val Lys Asp Arg Val Asp Glu Gly Gly Trp Ser Ser Lys Pro Arg Lys
                85                  90                  95

Gly Met Gly Thr Asn Leu Ser Val Pro Asn Pro Leu Gly Phe Phe Pro
            100                 105                 110

Asp His Gln Leu Asp Pro Ala Phe Gly Ala Asn Ser Asn Asn Pro Asp
        115                 120                 125

Trp Asp Phe Asn Pro Ile Lys Asp His Trp Pro Ala Ala Asn Gln Val
130                 135                 140

Gly Val Gly Ala Phe Gly Pro Gly Leu Thr Pro Pro His Gly Gly Ile
145                 150                 155                 160

Leu Gly Trp Ser Pro Gln Ala Gln Gly Ile Leu Thr Thr Val Ser Thr
                165                 170                 175

Ile Pro Pro Pro Ala Ser Thr Asn Arg Gln Ser Gly Arg Gln Pro Thr
            180                 185                 190

Pro Ile Ser Pro Pro Leu Arg Asp Ser His Pro Gln Ala Met Gln Trp
        195                 200                 205

Asn Ser Thr Ala Phe His Gln Ala Leu Gln Asp Pro Arg Val Arg Gly
    210                 215                 220

Leu Tyr Phe Pro Ala Gly Gly Ser Ser Ser Gly Thr Val Asn Pro Ala
225                 230                 235                 240

Pro Asn Ile Ala Ser His Ile Ser Ser Ile Ser Ala Arg Thr Gly Asp
                245                 250                 255

Pro Val Thr Asn Pro Glu Gly Phe Pro Phe Lys Tyr Val Asp Arg Val
            260                 265                 270

Asp Glu Val Asp His Thr Asn Phe Lys Tyr Asn Tyr Ser Val Ile Glu
        275                 280                 285

Gly Gly Pro Ile Gly Asp Thr Leu Glu Lys Ile Ser Asn Glu Ile Lys
    290                 295                 300

Ile Pro Glu Gly Phe Pro Phe Lys Tyr Val Asp Arg Val Asp Glu Asp
305                 310                 315                 320
```

His Thr Asn Phe Lys Tyr Asn Tyr Ser Val Ile Glu Gly Gly Pro Ile
            325                 330                 335

Gly Asp Thr Leu Glu Lys Ile Ser Asn Glu Ile Lys Ile
            340                 345

<210> SEQ ID NO 20
<211> LENGTH: 307
<212> TYPE: PRT
<213> ORGANISM: Artificial Sequence
<220> FEATURE:
<223> OTHER INFORMATION: Synthetic Peptide

<400> SEQUENCE: 20

Met Ala Asp Leu Gly Tyr Gly Pro Ala Thr Pro Ala Ala Pro Ala Ala
1               5                   10                  15

Gly Tyr Thr Pro Ala Thr Pro Ala Ala Pro Ala Glu Ala Ala Pro Ala
            20                  25                  30

Gly Lys Ala Thr Thr Glu Glu Gln Lys Leu Ile Glu Lys Ile Asn Ala
        35                  40                  45

Gly Phe Lys Ala Ala Leu Ala Ala Ala Gly Val Gln Pro Ala Asp
    50                  55                  60

Lys Tyr Arg Gly Gly Trp Ser Ser Lys Pro Arg Lys Gly Met Gly Thr
65                  70                  75                  80

Asn Leu Ser Val Pro Asn Pro Leu Gly Phe Phe Pro Asp His Gln Leu
                85                  90                  95

Asp Pro Ala Phe Gly Ala Asn Ser Asn Asn Pro Asp Trp Asp Phe Asn
            100                 105                 110

Pro Ile Lys Asp His Trp Pro Ala Ala Asn Gln Val Gly Val Gly Ala
            115                 120                 125

Phe Gly Pro Gly Leu Thr Pro Pro His Gly Gly Ile Leu Gly Trp Ser
    130                 135                 140

Pro Gln Ala Gln Gly Ile Leu Thr Thr Val Ser Thr Ile Pro Pro Pro
145                 150                 155                 160

Ala Ser Thr Asn Arg Gln Ser Gly Arg Gln Pro Thr Pro Ile Ser Pro
                165                 170                 175

Pro Leu Arg Asp Ser His Pro Gln Ala Met Gln Trp Asn Ser Thr Ala
            180                 185                 190

Phe His Gln Ala Leu Gln Asp Pro Arg Val Arg Gly Leu Tyr Phe Pro
        195                 200                 205

Ala Gly Gly Ser Ser Ser Gly Thr Val Asn Pro Ala Pro Asn Ile Ala
    210                 215                 220

Ser His Ile Ser Ser Ile Ser Ala Arg Thr Gly Asp Pro Val Thr Asn
225                 230                 235                 240

Glu Ala Ala Phe Asn Asp Ala Ile Lys Ala Ser Thr Gly Gly Ala Tyr
                245                 250                 255

Glu Ser Tyr Lys Phe Ile Pro Ala Leu Glu Ala Ala Val Lys Ala Glu
            260                 265                 270

Glu Val Lys Val Ile Pro Ala Gly Glu Leu Gln Val Ile Glu Lys Val
        275                 280                 285

Asp Ala Ala Phe Lys Val Ala Thr Ala Ala Asn Ala Ala Pro Ala
    290                 295                 300

Asn Asp Lys
305

<210> SEQ ID NO 21

```
<211> LENGTH: 173
<212> TYPE: PRT
<213> ORGANISM: Hepatitis B virus

<400> SEQUENCE: 21

Gly Gly Trp Ser Ser Lys Pro Arg Lys Gly Met Gly Thr Asn Leu Ser
1               5                   10                  15

Val Pro Asn Pro Leu Gly Phe Phe Pro Asp His Gln Leu Asp Pro Ala
                20                  25                  30

Phe Gly Ala Asn Ser Asn Asn Pro Asp Trp Asp Phe Asn Pro Ile Lys
            35                  40                  45

Asp His Trp Pro Ala Ala Asn Gln Val Gly Val Gly Ala Phe Gly Pro
        50                  55                  60

Gly Leu Thr Pro Pro His Gly Gly Ile Leu Gly Trp Ser Pro Gln Ala
65                  70                  75                  80

Gln Gly Ile Leu Thr Thr Val Ser Thr Ile Pro Pro Pro Ala Ser Thr
                85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Ala Phe His Gln
        115                 120                 125

Ala Leu Gln Asp Pro Arg Val Arg Gly Leu Tyr Phe Pro Ala Gly Gly
    130                 135                 140

Ser Ser Ser Gly Thr Val Asn Pro Ala Pro Asn Ile Ala Ser His Ile
145                 150                 155                 160

Ser Ser Ile Ser Ala Arg Thr Gly Asp Pro Val Thr Asn
                165                 170

<210> SEQ ID NO 22
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 22

Ala Thr Thr Glu Glu Gln Lys Leu Ile Glu Lys Ile Asn Ala Gly Phe
1               5                   10                  15

Lys Ala Ala Leu Ala Ala Ala Gly Val Gln Pro Ala Asp Lys Tyr
                20                  25                  30

Arg

<210> SEQ ID NO 23
<211> LENGTH: 40
<212> TYPE: PRT
<213> ORGANISM: Artificial Sequence
<220> FEATURE:
<223> OTHER INFORMATION: Alt a 1 derived hypoallergenic molecule

<400> SEQUENCE: 23

Ala Pro Leu Glu Ser Arg Gln Asp Thr Ala Ser Cys Pro Val Thr Thr
1               5                   10                  15

Glu Gly Asp Tyr Val Trp Lys Ile Ser Glu Phe Tyr Gly Arg Lys Pro
                20                  25                  30

Glu Gly Thr Tyr Tyr Asn Ser Leu
            35                  40

<210> SEQ ID NO 24
<211> LENGTH: 37
```

```
<212> TYPE: PRT
<213> ORGANISM: Artificial Sequence
<220> FEATURE:
<223> OTHER INFORMATION: Alt a 1 derived hypoallergenic molecule

<400> SEQUENCE: 24

Gly Phe Asn Ile Lys Ala Thr Asn Gly Gly Thr Leu Asp Phe Thr Cys
1               5                   10                  15

Ser Ala Gln Ala Asp Lys Leu Glu Asp His Lys Trp Tyr Ser Cys Gly
            20                  25                  30

Glu Asn Ser Phe Met
        35

<210> SEQ ID NO 25
<211> LENGTH: 30
<212> TYPE: PRT
<213> ORGANISM: Artificial Sequence
<220> FEATURE:
<223> OTHER INFORMATION: Alt a 1 derived hypoallergenic molecule

<400> SEQUENCE: 25

Glu Asn Ser Phe Met Asp Phe Ser Phe Asp Ser Asp Arg Ser Gly Leu
1               5                   10                  15

Leu Leu Lys Gln Lys Val Ser Asp Asp Ile Thr Tyr Val Ala
            20                  25                  30

<210> SEQ ID NO 26
<211> LENGTH: 37
<212> TYPE: PRT
<213> ORGANISM: Artificial Sequence
<220> FEATURE:
<223> OTHER INFORMATION: Alt a 1 derived hypoallergenic molecule

<400> SEQUENCE: 26

Thr Ala Thr Leu Pro Asn Tyr Cys Arg Ala Gly Gly Asn Gly Pro Lys
1               5                   10                  15

Asp Phe Val Cys Gln Gly Val Ala Asp Ala Tyr Ile Thr Leu Val Thr
            20                  25                  30

Leu Pro Lys Ser Ser
        35

<210> SEQ ID NO 27
<211> LENGTH: 40
<212> TYPE: PRT
<213> ORGANISM: Artificial Sequence
<220> FEATURE:
<223> OTHER INFORMATION: Alt a 2 derived hypoallergenic molecule

<400> SEQUENCE: 27

Met His Ser Ser Asn Asn Phe Phe Lys Asp Asn Ile Phe Arg Ser Leu
1               5                   10                  15

Ser Lys Glu Asp Pro Asp Tyr Ser Arg Asn Ile Glu Gly Gln Val Ile
            20                  25                  30

Arg Leu His Trp Asp Trp Ala Gln
        35                  40

<210> SEQ ID NO 28
<211> LENGTH: 40
<212> TYPE: PRT
<213> ORGANISM: Artificial Sequence
<220> FEATURE:
<223> OTHER INFORMATION: Alt a 2 derived hypoallergenic molecule

<400> SEQUENCE: 28
```

```
Leu Leu Met Leu Ser Ala Lys Arg Met Lys Val Ala Phe Lys Leu Asp
1               5                   10                  15

Ile Glu Lys Asp Gln Arg Val Trp Asp Arg Cys Thr Ala Asp Asp Leu
            20                  25                  30

Lys Gly Arg Asn Gly Phe Lys Arg
        35                  40
```

<210> SEQ ID NO 29
<211> LENGTH: 40
<212> TYPE: PRT
<213> ORGANISM: Artificial Sequence
<220> FEATURE:
<223> OTHER INFORMATION: Alt a 2 derived hypoallergenic molecule

<400> SEQUENCE: 29

```
Cys Leu Gln Phe Thr Leu Tyr Arg Pro Arg Asp Leu Leu Ser Leu Leu
1               5                   10                  15

Asn Glu Ala Phe Phe Ser Ala Phe Arg Glu Asn Arg Glu Thr Ile Ile
            20                  25                  30

Asn Thr Asp Leu Glu Tyr Ala Ala
        35                  40
```

<210> SEQ ID NO 30
<211> LENGTH: 40
<212> TYPE: PRT
<213> ORGANISM: Artificial Sequence
<220> FEATURE:
<223> OTHER INFORMATION: Alt a 2 derived hypoallergenic molecule

<400> SEQUENCE: 30

```
Lys Ser Ile Ser Met Ala Arg Leu Glu Asp Leu Trp Lys Glu Tyr Gln
1               5                   10                  15

Lys Ile Phe Pro Ser Ile Gln Val Ile Thr Ser Ala Phe Arg Ser Ile
            20                  25                  30

Glu Pro Glu Leu Thr Val Tyr Thr
        35                  40
```

<210> SEQ ID NO 31
<211> LENGTH: 30
<212> TYPE: PRT
<213> ORGANISM: Artificial Sequence
<220> FEATURE:
<223> OTHER INFORMATION: Alt a 2 derived hypoallergenic molecule

<400> SEQUENCE: 31

```
Cys Leu Lys Lys Ile Glu Ala Ser Phe Glu Leu Ile Glu Glu Asn Gly
1               5                   10                  15

Asp Pro Lys Ile Thr Ser Glu Ile Gln Leu Leu Lys Ala Ser
            20                  25                  30
```

<210> SEQ ID NO 32
<211> LENGTH: 34
<212> TYPE: PRT
<213> ORGANISM: Artificial Sequence
<220> FEATURE:
<223> OTHER INFORMATION: Alt a 6 derived hypoallergenic molecule

<400> SEQUENCE: 32

```
Met Thr Ile Thr Lys Ile His Ala Arg Ser Val Tyr Asp Ser Arg Gly
1               5                   10                  15

Asn Pro Thr Val Glu Val Asp Ile Val Thr Glu Thr Gly Leu His Arg
            20                  25                  30
```

```
Ala Ile

<210> SEQ ID NO 33
<211> LENGTH: 40
<212> TYPE: PRT
<213> ORGANISM: Artificial Sequence
<220> FEATURE:
<223> OTHER INFORMATION: Alt a 6 derived hypoallergenic molecule

<400> SEQUENCE: 33

Val Thr Glu Thr Gly Leu His Arg Ala Ile Val Pro Ser Gly Ala Ser
1               5                   10                  15

Thr Gly Ser His Glu Ala Cys Glu Leu Arg Asp Gly Asp Lys Ser Lys
            20                  25                  30

Trp Gly Gly Lys Gly Val Thr Lys
        35                  40

<210> SEQ ID NO 34
<211> LENGTH: 42
<212> TYPE: PRT
<213> ORGANISM: Artificial Sequence
<220> FEATURE:
<223> OTHER INFORMATION: Alt a 6 derived hypoallergenic molecule

<400> SEQUENCE: 34

Ala Pro Ala Leu Ile Lys Glu Lys Leu Asp Val Lys Asp Gln Ser Ala
1               5                   10                  15

Val Asp Ala Phe Leu Asn Lys Leu Asp Gly Thr Thr Asn Lys Thr Asn
            20                  25                  30

Leu Gly Ala Asn Ala Ile Leu Gly Val Ser
        35                  40

<210> SEQ ID NO 35
<211> LENGTH: 41
<212> TYPE: PRT
<213> ORGANISM: Artificial Sequence
<220> FEATURE:
<223> OTHER INFORMATION: Alt a 6 derived hypoallergenic molecule

<400> SEQUENCE: 35

Glu Lys Gly Val Pro Leu Tyr Ala His Ile Ser Asp Leu Ala Gly Thr
1               5                   10                  15

Lys Lys Pro Tyr Val Leu Pro Val Pro Phe Gln Asn Val Leu Asn Gly
            20                  25                  30

Gly Ser His Ala Gly Gly Arg Leu Ala
        35                  40

<210> SEQ ID NO 36
<211> LENGTH: 40
<212> TYPE: PRT
<213> ORGANISM: Artificial Sequence
<220> FEATURE:
<223> OTHER INFORMATION: Alt a 6 derived hypoallergenic molecule

<400> SEQUENCE: 36

Cys Glu Ala Pro Thr Phe Ser Glu Ala Met Arg Gln Gly Ala Glu Val
1               5                   10                  15

Tyr Gln Lys Leu Lys Ala Leu Ala Lys Lys Thr Tyr Gly Gln Ser Ala
            20                  25                  30

Gly Asn Val Gly Asp Glu Gly Gly
        35                  40
```

```
<210> SEQ ID NO 37
<211> LENGTH: 40
<212> TYPE: PRT
<213> ORGANISM: Artificial Sequence
<220> FEATURE:
<223> OTHER INFORMATION: Alt a 6 derived hypoallergenic molecule

<400> SEQUENCE: 37

Ile Lys Ile Ala Met Asp Val Ala Ser Ser Glu Phe Tyr Lys Ala Asp
1               5                   10                  15

Glu Lys Lys Tyr Asp Leu Asp Phe Lys Asn Pro Asp Ser Asp Lys Ser
            20                  25                  30

Lys Trp Leu Thr Tyr Glu Gln Leu
        35                  40

<210> SEQ ID NO 38
<211> LENGTH: 40
<212> TYPE: PRT
<213> ORGANISM: Artificial Sequence
<220> FEATURE:
<223> OTHER INFORMATION: Alt a 6 derived hypoallergenic molecule

<400> SEQUENCE: 38

Val Ser Ile Glu Asp Pro Phe Ala Glu Asp Asp Trp Glu Ala Trp Ser
1               5                   10                  15

Tyr Phe Phe Lys Thr Tyr Asp Gly Gln Ile Val Gly Asp Asp Leu Thr
            20                  25                  30

Val Thr Asn Pro Glu Phe Ile Lys
        35                  40

<210> SEQ ID NO 39
<211> LENGTH: 40
<212> TYPE: PRT
<213> ORGANISM: Artificial Sequence
<220> FEATURE:
<223> OTHER INFORMATION: Alt a 6 derived hypoallergenic molecule

<400> SEQUENCE: 39

Ala Lys Asp Ala Phe Gly Ala Gly Trp Gly Val Met Val Ser His Arg
1               5                   10                  15

Ser Gly Glu Thr Glu Asp Val Thr Ile Ala Asp Ile Val Val Gly Leu
            20                  25                  30

Arg Ser Gly Gln Ile Lys Thr Gly
        35                  40

<210> SEQ ID NO 40
<211> LENGTH: 38
<212> TYPE: PRT
<213> ORGANISM: Artificial Sequence
<220> FEATURE:
<223> OTHER INFORMATION: Alt a 6 derived hypoallergenic molecule

<400> SEQUENCE: 40

Ala Pro Ala Arg Ser Glu Arg Leu Ala Lys Leu Asn Gln Ile Leu Arg
1               5                   10                  15

Ile Glu Glu Glu Leu Gly Asp Asn Ala Val Tyr Ala Gly Asn Asn Phe
            20                  25                  30

Arg Thr Ala Val Asn Leu
        35

<210> SEQ ID NO 41
<211> LENGTH: 40
```

<212> TYPE: PRT
<213> ORGANISM: Artificial Sequence
<220> FEATURE:
<223> OTHER INFORMATION: Amb a 1 derived hypoallergenic molecule

<400> SEQUENCE: 41

```
Glu Ile Leu Pro Val Asn Glu Thr Arg Arg Leu Thr Thr Ser Gly Ala
1               5                   10                  15

Tyr Asn Ile Ile Asp Gly Cys Trp Arg Gly Lys Ala Asp Trp Ala Glu
            20                  25                  30

Asn Arg Lys Ala Leu Ala Asp Cys
        35                  40
```

<210> SEQ ID NO 42
<211> LENGTH: 41
<212> TYPE: PRT
<213> ORGANISM: Artificial Sequence
<220> FEATURE:
<223> OTHER INFORMATION: Amb a 1 derived hypoallergenic molecule

<400> SEQUENCE: 42

```
Gly Gly Lys Asp Gly Asp Ile Tyr Thr Val Thr Ser Glu Leu Asp Asp
1               5                   10                  15

Asp Val Ala Asn Pro Lys Glu Gly Thr Leu Arg Phe Gly Ala Ala Gln
            20                  25                  30

Asn Arg Pro Leu Trp Ile Ile Phe Glu
        35                  40
```

<210> SEQ ID NO 43
<211> LENGTH: 31
<212> TYPE: PRT
<213> ORGANISM: Artificial Sequence
<220> FEATURE:
<223> OTHER INFORMATION: Amb a 1 derived hypoallergenic molecule

<400> SEQUENCE: 43

```
Ile Arg Leu Asp Lys Glu Met Val Val Asn Ser Asp Lys Thr Ile Asp
1               5                   10                  15

Gly Arg Gly Ala Lys Val Glu Ile Ile Asn Ala Gly Phe Thr Leu
            20                  25                  30
```

<210> SEQ ID NO 44
<211> LENGTH: 41
<212> TYPE: PRT
<213> ORGANISM: Artificial Sequence
<220> FEATURE:
<223> OTHER INFORMATION: Amb a 1 derived hypoallergenic molecule

<400> SEQUENCE: 44

```
Asn Val Ile Ile His Asn Ile Asn Met His Asp Val Lys Val Asn Pro
1               5                   10                  15

Gly Gly Leu Ile Lys Ser Asn Asp Gly Pro Ala Ala Pro Arg Ala Gly
            20                  25                  30

Ser Asp Gly Asp Ala Ile Ser Ile Ser
        35                  40
```

<210> SEQ ID NO 45
<211> LENGTH: 39
<212> TYPE: PRT
<213> ORGANISM: Artificial Sequence
<220> FEATURE:
<223> OTHER INFORMATION: Amb a 1 derived hypoallergenic molecule

<400> SEQUENCE: 45

-continued

Gly Thr Thr Arg Leu Thr Val Ser Asn Ser Leu Phe Thr Gln His Gln
1 5 10 15

Phe Val Leu Leu Phe Gly Ala Gly Asp Glu Asn Ile Glu Asp Arg Gly
20 25 30

Met Leu Ala Thr Val Ala Phe
35

<210> SEQ ID NO 46
<211> LENGTH: 37
<212> TYPE: PRT
<213> ORGANISM: Artificial Sequence
<220> FEATURE:
<223> OTHER INFORMATION: Amb a 1 derived hypoallergenic molecule

<400> SEQUENCE: 46

Asn Thr Phe Thr Asp Asn Val Asp Gln Arg Met Pro Arg Cys Arg His
1 5 10 15

Gly Phe Phe Gln Val Val Asn Asn Asn Tyr Asp Lys Trp Gly Ser Tyr
20 25 30

Ala Ile Gly Gly Ser
35

<210> SEQ ID NO 47
<211> LENGTH: 46
<212> TYPE: PRT
<213> ORGANISM: Artificial Sequence
<220> FEATURE:
<223> OTHER INFORMATION: Amb a 1 derived hypoallergenic molecule

<400> SEQUENCE: 47

Ile Leu Ser Gln Gly Asn Arg Phe Cys Ala Pro Asp Glu Arg Ser Lys
1 5 10 15

Lys Asn Val Leu Gly Arg His Gly Glu Ala Ala Ala Glu Ser Met Lys
20 25 30

Trp Asn Trp Arg Thr Asn Lys Asp Val Leu Glu Asn Gly Ala
35 40 45

<210> SEQ ID NO 48
<211> LENGTH: 41
<212> TYPE: PRT
<213> ORGANISM: Artificial Sequence
<220> FEATURE:
<223> OTHER INFORMATION: Amb a 1 derived hypoallergenic molecule

<400> SEQUENCE: 48

Gly Val Asp Pro Val Leu Thr Pro Glu Gln Ser Ala Gly Met Ile Pro
1 5 10 15

Ala Glu Pro Gly Glu Ser Ala Leu Ser Leu Thr Ser Ser Ala Gly Val
20 25 30

Leu Ser Cys Gln Pro Gly Ala Pro Cys
35 40

<210> SEQ ID NO 49
<211> LENGTH: 44
<212> TYPE: PRT
<213> ORGANISM: Artificial Sequence
<220> FEATURE:
<223> OTHER INFORMATION: Art v 1 derived hypoallergenic molecule

<400> SEQUENCE: 49

Ser Lys Leu Cys Glu Lys Thr Ser Lys Thr Tyr Ser Gly Lys Cys Asp
1 5 10 15

```
Asn Lys Lys Cys Asp Lys Lys Cys Ile Glu Trp Glu Lys Ala Gln His
                20                  25                  30

Gly Ala Cys His Lys Arg Glu Ala Gly Lys Glu Ser
            35                  40
```

<210> SEQ ID NO 50
<211> LENGTH: 31
<212> TYPE: PRT
<213> ORGANISM: Artificial Sequence
<220> FEATURE:
<223> OTHER INFORMATION: Art v 1 derived hypoallergenic molecule

<400> SEQUENCE: 50

```
Ser Cys Phe Cys Tyr Phe Asp Cys Ser Lys Ser Pro Pro Gly Ala Thr
1               5                   10                  15

Pro Ala Pro Pro Gly Ala Ala Pro Pro Ala Ala Gly Gly Ser
                20                  25                  30
```

<210> SEQ ID NO 51
<211> LENGTH: 41
<212> TYPE: PRT
<213> ORGANISM: Artificial Sequence
<220> FEATURE:
<223> OTHER INFORMATION: Art v 1 derived hypoallergenic molecule

<400> SEQUENCE: 51

```
Ala Pro Pro Pro Ala Ala Gly Gly Ser Pro Ser Pro Ala Asp Gly
1               5                   10                  15

Gly Ser Pro Pro Pro Ala Asp Gly Gly Ser Pro Pro Val Asp Gly
                20                  25                  30

Gly Ser Pro Pro Pro Pro Ser Thr His
            35                  40
```

<210> SEQ ID NO 52
<211> LENGTH: 38
<212> TYPE: PRT
<213> ORGANISM: Artificial Sequence
<220> FEATURE:
<223> OTHER INFORMATION: Can f 1 derived hypoallergenic molecule

<400> SEQUENCE: 52

```
Gln Asp Thr Pro Ala Leu Gly Lys Asp Thr Val Ala Val Ser Gly Lys
1               5                   10                  15

Trp Tyr Leu Lys Ala Met Thr Ala Asp Gln Glu Val Pro Glu Lys Pro
                20                  25                  30

Asp Ser Val Thr Pro Met
            35
```

<210> SEQ ID NO 53
<211> LENGTH: 40
<212> TYPE: PRT
<213> ORGANISM: Artificial Sequence
<220> FEATURE:
<223> OTHER INFORMATION: Can f 1 derived hypoallergenic molecule

<400> SEQUENCE: 53

```
Asp Ser Val Thr Pro Met Ile Leu Lys Ala Gln Lys Gly Gly Asn Leu
1               5                   10                  15

Glu Ala Lys Ile Thr Met Leu Thr Asn Gly Gln Cys Gln Asn Ile Thr
                20                  25                  30

Val Val Leu His Lys Thr Ser Glu
            35                  40
```

<210> SEQ ID NO 54
<211> LENGTH: 41
<212> TYPE: PRT
<213> ORGANISM: Artificial Sequence
<220> FEATURE:
<223> OTHER INFORMATION: Can f 1 derived hypoallergenic molecule

<400> SEQUENCE: 54

Cys Gln Asn Ile Thr Val Val Leu His Lys Thr Ser Glu Pro Gly Lys
1               5                   10                  15

Tyr Thr Ala Tyr Glu Gly Gln Arg Val Val Phe Ile Gln Pro Ser Pro
            20                  25                  30

Val Arg Asp His Tyr Ile Leu Tyr Cys
        35                  40

<210> SEQ ID NO 55
<211> LENGTH: 40
<212> TYPE: PRT
<213> ORGANISM: Artificial Sequence
<220> FEATURE:
<223> OTHER INFORMATION: Can f 1 derived hypoallergenic molecule

<400> SEQUENCE: 55

Gln Pro Ser Pro Val Arg Asp His Tyr Ile Leu Tyr Cys Glu Gly Glu
1               5                   10                  15

Leu His Gly Arg Gln Ile Arg Met Ala Lys Leu Leu Gly Arg Asp Pro
            20                  25                  30

Glu Gln Ser Gln Glu Ala Leu Glu
        35                  40

<210> SEQ ID NO 56
<211> LENGTH: 40
<212> TYPE: PRT
<213> ORGANISM: Artificial Sequence
<220> FEATURE:
<223> OTHER INFORMATION: Can f 1 derived hypoallergenic molecule

<400> SEQUENCE: 56

Arg Asp Pro Glu Gln Ser Gln Glu Ala Leu Glu Asp Phe Arg Glu Phe
1               5                   10                  15

Ser Arg Ala Lys Gly Leu Asn Gln Glu Ile Leu Glu Leu Ala Gln Ser
            20                  25                  30

Glu Thr Cys Ser Pro Gly Gly Gln
        35                  40

<210> SEQ ID NO 57
<211> LENGTH: 40
<212> TYPE: PRT
<213> ORGANISM: Artificial Sequence
<220> FEATURE:
<223> OTHER INFORMATION: Can f 2 derived hypoallergenic molecule

<400> SEQUENCE: 57

Gln Glu Gly Asn His Glu Glu Pro Gln Gly Gly Leu Glu Glu Leu Ser
1               5                   10                  15

Gly Arg Trp His Ser Val Ala Leu Ala Ser Asn Lys Ser Asp Leu Ile
            20                  25                  30

Lys Pro Trp Gly His Phe Arg Val
        35                  40

<210> SEQ ID NO 58

<211> LENGTH: 40
<212> TYPE: PRT
<213> ORGANISM: Artificial Sequence
<220> FEATURE:
<223> OTHER INFORMATION: Can f 2 derived hypoallergenic molecule

<400> SEQUENCE: 58

Pro Trp Gly His Phe Arg Val Phe Ile His Ser Met Ser Ala Lys Asp
1               5                   10                  15

Gly Asn Leu His Gly Asp Ile Leu Ile Pro Gln Asp Gly Gln Cys Glu
            20                  25                  30

Lys Val Ser Leu Thr Ala Phe Lys
        35                  40

<210> SEQ ID NO 59
<211> LENGTH: 38
<212> TYPE: PRT
<213> ORGANISM: Artificial Sequence
<220> FEATURE:
<223> OTHER INFORMATION: Can f 2 derived hypoallergenic molecule

<400> SEQUENCE: 59

Cys Glu Lys Val Ser Leu Thr Ala Phe Lys Thr Ala Thr Ser Asn Lys
1               5                   10                  15

Phe Asp Leu Glu Tyr Trp Gly His Asn Asp Leu Tyr Leu Ala Glu Val
            20                  25                  30

Asp Pro Lys Ser Tyr Leu
        35

<210> SEQ ID NO 60
<211> LENGTH: 39
<212> TYPE: PRT
<213> ORGANISM: Artificial Sequence
<220> FEATURE:
<223> OTHER INFORMATION: Can f 2 derived hypoallergenic molecule

<400> SEQUENCE: 60

Asn Asp Leu Tyr Leu Ala Glu Val Asp Pro Lys Ser Tyr Leu Ile Leu
1               5                   10                  15

Tyr Met Ile Asn Gln Tyr Asn Asp Thr Ser Leu Val Ala His Leu
            20                  25                  30

Met Val Arg Asp Leu Ser Arg
        35

<210> SEQ ID NO 61
<211> LENGTH: 42
<212> TYPE: PRT
<213> ORGANISM: Artificial Sequence
<220> FEATURE:
<223> OTHER INFORMATION: Can f 2 derived hypoallergenic molecule

<400> SEQUENCE: 61

Val Arg Asp Leu Ser Arg Gln Gln Asp Phe Leu Pro Ala Phe Glu Ser
1               5                   10                  15

Val Cys Glu Asp Ile Gly Leu His Lys Asp Gln Ile Val Val Leu Ser
            20                  25                  30

Asp Asp Asp Arg Cys Gln Gly Ser Arg Asp
        35                  40

<210> SEQ ID NO 62
<211> LENGTH: 34
<212> TYPE: PRT
<213> ORGANISM: Artificial Sequence

```
<220> FEATURE:
<223> OTHER INFORMATION: Fel d 2 derived hypoallergenic molecule

<400> SEQUENCE: 62

Glu Ala His Gln Ser Glu Ile Ala His Arg Phe Asn Asp Leu Gly Glu
1               5                   10                  15

Glu His Phe Arg Gly Leu Val Leu Val Ala Phe Ser Gln Tyr Leu Gln
            20                  25                  30

Gln Cys

<210> SEQ ID NO 63
<211> LENGTH: 35
<212> TYPE: PRT
<213> ORGANISM: Artificial Sequence
<220> FEATURE:
<223> OTHER INFORMATION: Fel d 2 derived hypoallergenic molecule

<400> SEQUENCE: 63

Cys Thr Val Ala Ser Leu Arg Asp Lys Tyr Gly Glu Met Ala Asp Cys
1               5                   10                  15

Cys Glu Lys Lys Glu Pro Glu Arg Asn Glu Cys Phe Leu Gln His Lys
            20                  25                  30

Asp Asp Asn
        35

<210> SEQ ID NO 64
<211> LENGTH: 30
<212> TYPE: PRT
<213> ORGANISM: Artificial Sequence
<220> FEATURE:
<223> OTHER INFORMATION: Fel d 2 derived hypoallergenic molecule

<400> SEQUENCE: 64

Asn Glu Gln Arg Phe Leu Gly Lys Tyr Leu Tyr Glu Ile Ala Arg Arg
1               5                   10                  15

His Pro Tyr Phe Tyr Ala Pro Glu Leu Leu Tyr Tyr Ala Glu
            20                  25                  30

<210> SEQ ID NO 65
<211> LENGTH: 31
<212> TYPE: PRT
<213> ORGANISM: Artificial Sequence
<220> FEATURE:
<223> OTHER INFORMATION: Fel d 2 derived hypoallergenic molecule

<400> SEQUENCE: 65

Cys Ala Asp Asp Arg Ala Asp Leu Ala Lys Tyr Ile Cys Glu Asn Gln
1               5                   10                  15

Asp Ser Ile Ser Thr Lys Leu Lys Glu Cys Cys Gly Lys Pro Val
            20                  25                  30

<210> SEQ ID NO 66
<211> LENGTH: 30
<212> TYPE: PRT
<213> ORGANISM: Artificial Sequence
<220> FEATURE:
<223> OTHER INFORMATION: Fel d 2 derived hypoallergenic molecule

<400> SEQUENCE: 66

Val Glu Asp Lys Glu Val Cys Lys Asn Tyr Gln Glu Ala Lys Asp Val
1               5                   10                  15

Phe Leu Gly Thr Phe Leu Tyr Glu Tyr Ser Arg Arg His Pro
            20                  25                  30
```

<210> SEQ ID NO 67
<211> LENGTH: 30
<212> TYPE: PRT
<213> ORGANISM: Artificial Sequence
<220> FEATURE:
<223> OTHER INFORMATION: Fel d 2 derived hypoallergenic molecule

<400> SEQUENCE: 67

```
Leu Ala Lys Glu Tyr Glu Ala Thr Leu Glu Lys Cys Cys Ala Thr Asp
1               5                   10                  15

Asp Pro Pro Ala Cys Tyr Ala His Val Phe Asp Glu Phe Lys
            20                  25                  30
```

<210> SEQ ID NO 68
<211> LENGTH: 30
<212> TYPE: PRT
<213> ORGANISM: Artificial Sequence
<220> FEATURE:
<223> OTHER INFORMATION: Fel d 2 derived hypoallergenic molecule

<400> SEQUENCE: 68

```
Glu Lys Gln Ile Lys Lys Gln Ser Ala Leu Val Glu Leu Leu Lys His
1               5                   10                  15

Lys Pro Lys Ala Thr Glu Glu Gln Leu Lys Thr Val Met Gly
            20                  25                  30
```

<210> SEQ ID NO 69
<211> LENGTH: 30
<212> TYPE: PRT
<213> ORGANISM: Artificial Sequence
<220> FEATURE:
<223> OTHER INFORMATION: Fel d 2 derived hypoallergenic molecule

<400> SEQUENCE: 69

```
Val Asp Lys Cys Cys Ala Ala Glu Asp Lys Glu Ala Cys Phe Ala Glu
1               5                   10                  15

Glu Gly Pro Lys Leu Val Ala Ala Ala Gln Ala Ala Leu Ala
            20                  25                  30
```

<210> SEQ ID NO 70
<211> LENGTH: 42
<212> TYPE: PRT
<213> ORGANISM: Artificial Sequence
<220> FEATURE:
<223> OTHER INFORMATION: Fel d 2 derived hypoallergenic molecule

<400> SEQUENCE: 70

```
Cys Pro Phe Glu Asp His Val Lys Leu Val Asn Glu Val Thr Glu Phe
1               5                   10                  15

Ala Lys Gly Cys Val Ala Asp Gln Ser Ala Ala Asn Cys Glu Lys Ser
            20                  25                  30

Leu His Glu Leu Leu Gly Asp Lys Leu Cys
        35                  40
```

<210> SEQ ID NO 71
<211> LENGTH: 41
<212> TYPE: PRT
<213> ORGANISM: Artificial Sequence
<220> FEATURE:
<223> OTHER INFORMATION: Fel d 2 derived hypoallergenic molecule

<400> SEQUENCE: 71

Cys Phe Leu Gln His Lys Asp Asp Asn Pro Gly Phe Gly Gln Leu Val

```
                1               5                  10                  15
Thr Pro Glu Ala Asp Ala Met Cys Thr Ala Phe His Glu Asn Glu Gln
                20                  25                  30

Arg Phe Leu Gly Lys Tyr Leu Tyr Glu
            35                  40

<210> SEQ ID NO 72
<211> LENGTH: 42
<212> TYPE: PRT
<213> ORGANISM: Artificial Sequence
<220> FEATURE:
<223> OTHER INFORMATION: Fel d 2 derived hypoallergenic molecule

<400> SEQUENCE: 72

Glu Glu Tyr Lys Gly Val Phe Thr Glu Cys Cys Glu Ala Ala Asp Lys
1               5                   10                  15

Ala Ala Cys Leu Thr Pro Lys Val Asp Ala Leu Arg Glu Lys Val Leu
                20                  25                  30

Ala Ser Ser Ala Lys Glu Arg Leu Lys Cys
            35                  40

<210> SEQ ID NO 73
<211> LENGTH: 38
<212> TYPE: PRT
<213> ORGANISM: Artificial Sequence
<220> FEATURE:
<223> OTHER INFORMATION: Fel d 2 derived hypoallergenic molecule

<400> SEQUENCE: 73

Cys Ala Ser Leu Gln Lys Phe Gly Glu Arg Ala Phe Lys Ala Trp Ser
1               5                   10                  15

Val Ala Arg Leu Ser Gln Lys Phe Pro Lys Ala Glu Phe Ala Glu Ile
                20                  25                  30

Ser Lys Leu Val Thr Asp
            35

<210> SEQ ID NO 74
<211> LENGTH: 38
<212> TYPE: PRT
<213> ORGANISM: Artificial Sequence
<220> FEATURE:
<223> OTHER INFORMATION: Fel d 2 derived hypoallergenic molecule

<400> SEQUENCE: 74

Phe Ala Glu Ile Ser Lys Leu Val Thr Asp Leu Ala Lys Ile His Lys
1               5                   10                  15

Glu Cys Cys His Gly Asp Leu Leu Glu Cys Ala Asp Asp Arg Ala Asp
                20                  25                  30

Leu Ala Lys Tyr Ile Cys
            35

<210> SEQ ID NO 75
<211> LENGTH: 38
<212> TYPE: PRT
<213> ORGANISM: Artificial Sequence
<220> FEATURE:
<223> OTHER INFORMATION: Fel d 2 derived hypoallergenic molecule

<400> SEQUENCE: 75

Cys Gly Lys Pro Val Leu Glu Lys Ser His Cys Ile Ser Glu Val Glu
1               5                   10                  15

Arg Asp Glu Leu Pro Ala Asp Leu Pro Pro Leu Ala Val Asp Phe Val
```

20                  25                  30
Glu Asp Lys Glu Val Cys
        35

<210> SEQ ID NO 76
<211> LENGTH: 42
<212> TYPE: PRT
<213> ORGANISM: Artificial Sequence
<220> FEATURE:
<223> OTHER INFORMATION: Fel d 2 derived hypoallergenic molecule

<400> SEQUENCE: 76

Cys Glu Leu Phe Glu Lys Leu Gly Glu Tyr Gly Phe Gln Asn Ala Leu
1               5                   10                  15

Leu Val Arg Tyr Thr Lys Lys Val Pro Gln Val Ser Thr Pro Thr Leu
                20                  25                  30

Val Glu Val Ser Arg Ser Leu Gly Lys Val
        35                  40

<210> SEQ ID NO 77
<211> LENGTH: 39
<212> TYPE: PRT
<213> ORGANISM: Artificial Sequence
<220> FEATURE:
<223> OTHER INFORMATION: Fel d 2 derived hypoallergenic molecule

<400> SEQUENCE: 77

Cys Thr His Pro Glu Ala Glu Arg Leu Ser Cys Ala Glu Asp Tyr Leu
1               5                   10                  15

Ser Val Val Leu Asn Arg Leu Cys Val Leu His Glu Lys Thr Pro Val
                20                  25                  30

Ser Glu Arg Val Thr Lys Cys
        35

<210> SEQ ID NO 78
<211> LENGTH: 42
<212> TYPE: PRT
<213> ORGANISM: Artificial Sequence
<220> FEATURE:
<223> OTHER INFORMATION: Fel d 2 derived hypoallergenic molecule

<400> SEQUENCE: 78

Cys Thr Glu Ser Leu Val Asn Arg Arg Pro Cys Phe Ser Ala Leu Gln
1               5                   10                  15

Val Asp Glu Thr Tyr Val Pro Lys Glu Phe Ser Ala Glu Thr Phe Thr
                20                  25                  30

Phe His Ala Asp Leu Cys Thr Leu Pro Glu
        35                  40

<210> SEQ ID NO 79
<211> LENGTH: 40
<212> TYPE: PRT
<213> ORGANISM: Artificial Sequence
<220> FEATURE:
<223> OTHER INFORMATION: Ole e 1 derived hypoallergenic molecule

<400> SEQUENCE: 79

Glu Asp Ile Pro Gln Pro Pro Val Ser Gln Phe His Ile Gln Gly Gln
1               5                   10                  15

Val Tyr Cys Asp Thr Cys Arg Ala Gly Phe Ile Thr Glu Leu Ser Glu
                20                  25                  30

Phe Ile Pro Gly Ala Ser Leu Arg

```
              35                  40

<210> SEQ ID NO 80
<211> LENGTH: 31
<212> TYPE: PRT
<213> ORGANISM: Artificial Sequence
<220> FEATURE:
<223> OTHER INFORMATION: Ole e 1 derived hypoallergenic molecule

<400> SEQUENCE: 80

Gly Ala Ser Leu Arg Leu Gln Cys Lys Asp Lys Glu Asn Gly Asp Val
1               5                   10                  15

Thr Phe Thr Glu Val Gly Tyr Thr Arg Ala Glu Gly Leu Tyr Ser
            20                  25                  30

<210> SEQ ID NO 81
<211> LENGTH: 37
<212> TYPE: PRT
<213> ORGANISM: Artificial Sequence
<220> FEATURE:
<223> OTHER INFORMATION: Ole e 1 derived hypoallergenic molecule

<400> SEQUENCE: 81

Gly Leu Tyr Ser Met Leu Val Glu Arg Asp His Lys Asn Glu Phe Cys
1               5                   10                  15

Glu Ile Thr Leu Ile Ser Ser Gly Arg Lys Asp Cys Asn Glu Ile Pro
            20                  25                  30

Thr Glu Gly Trp Ala
        35

<210> SEQ ID NO 82
<211> LENGTH: 35
<212> TYPE: PRT
<213> ORGANISM: Artificial Sequence
<220> FEATURE:
<223> OTHER INFORMATION: Ole e 1 derived hypoallergenic molecule

<400> SEQUENCE: 82

Gly Arg Lys Asp Cys Asn Glu Ile Pro Thr Glu Gly Trp Ala Lys Pro
1               5                   10                  15

Ser Leu Lys Phe Lys Leu Asn Thr Val Asn Gly Thr Thr Arg Thr Val
            20                  25                  30

Asn Pro Leu
        35

<210> SEQ ID NO 83
<211> LENGTH: 39
<212> TYPE: PRT
<213> ORGANISM: Artificial Sequence
<220> FEATURE:
<223> OTHER INFORMATION: Ole e 1 derived hypoallergenic molecule

<400> SEQUENCE: 83

Leu Asn Thr Val Asn Gly Thr Thr Arg Thr Val Asn Pro Leu Gly Phe
1               5                   10                  15

Phe Lys Lys Glu Ala Leu Pro Lys Cys Ala Gln Val Tyr Asn Lys Leu
            20                  25                  30

Gly Met Tyr Pro Pro Asn Met
        35

<210> SEQ ID NO 84
<211> LENGTH: 30
<212> TYPE: PRT
```

```
<213> ORGANISM: Artificial Sequence
<220> FEATURE:
<223> OTHER INFORMATION: Par j 2 derived hypoallergenic molecule

<400> SEQUENCE: 84

Gly Glu Glu Ala Cys Gly Lys Val Val Gln Asp Ile Met Pro Cys Leu
 1               5                  10                  15
His Phe Val Lys Gly Glu Glu Lys Glu Pro Ser Lys Glu Cys
            20                  25                  30

<210> SEQ ID NO 85
<211> LENGTH: 36
<212> TYPE: PRT
<213> ORGANISM: Artificial Sequence
<220> FEATURE:
<223> OTHER INFORMATION: Par j 2 derived hypoallergenic molecule

<400> SEQUENCE: 85

Cys Leu His Phe Val Lys Gly Glu Glu Lys Glu Pro Ser Lys Glu Cys
 1               5                  10                  15
Cys Ser Gly Thr Lys Lys Leu Ser Glu Glu Val Lys Thr Thr Glu Gln
            20                  25                  30
Lys Arg Glu Ala
        35

<210> SEQ ID NO 86
<211> LENGTH: 37
<212> TYPE: PRT
<213> ORGANISM: Artificial Sequence
<220> FEATURE:
<223> OTHER INFORMATION: Par j 2 derived hypoallergenic molecule

<400> SEQUENCE: 86

Cys Cys Ser Gly Thr Lys Lys Leu Ser Glu Glu Val Lys Thr Thr Glu
 1               5                  10                  15
Gln Lys Arg Glu Ala Cys Lys Cys Ile Val Arg Ala Thr Lys Gly Ile
            20                  25                  30
Ser Gly Ile Lys Asn
        35

<210> SEQ ID NO 87
<211> LENGTH: 37
<212> TYPE: PRT
<213> ORGANISM: Artificial Sequence
<220> FEATURE:
<223> OTHER INFORMATION: Par j 2 derived hypoallergenic molecule

<400> SEQUENCE: 87

Glu Leu Val Ala Glu Val Pro Lys Lys Cys Asp Ile Lys Thr Thr Leu
 1               5                  10                  15
Pro Pro Ile Thr Ala Asp Phe Asp Cys Ser Lys Ile Gln Ser Thr Ile
            20                  25                  30
Phe Arg Gly Tyr Tyr
        35

<210> SEQ ID NO 88
<211> LENGTH: 30
<212> TYPE: PRT
<213> ORGANISM: Artificial Sequence
<220> FEATURE:
<223> OTHER INFORMATION: Der p 1 derived hypoallergenic molecule

<400> SEQUENCE: 88
```

-continued

```
Thr Asn Ala Cys Ser Ile Asn Gly Asn Ala Pro Ala Glu Ile Asp Leu
1               5                  10                  15
Arg Gln Met Arg Thr Val Thr Pro Ile Arg Met Gln Gly Gly
            20                  25                  30
```

<210> SEQ ID NO 89
<211> LENGTH: 33
<212> TYPE: PRT
<213> ORGANISM: Artificial Sequence
<220> FEATURE:
<223> OTHER INFORMATION: Der p 1 derived hypoallergenic molecule

<400> SEQUENCE: 89

```
Asn Gln Ser Leu Asp Leu Ala Glu Gln Glu Leu Val Asp Cys Ala Ser
1               5                  10                  15
Gln His Gly Cys His Gly Asp Thr Ile Pro Arg Gly Ile Glu Tyr Ile
            20                  25                  30
Gln
```

<210> SEQ ID NO 90
<211> LENGTH: 31
<212> TYPE: PRT
<213> ORGANISM: Artificial Sequence
<220> FEATURE:
<223> OTHER INFORMATION: Der p 1 derived hypoallergenic molecule

<400> SEQUENCE: 90

```
His Asn Gly Val Val Gln Glu Ser Tyr Tyr Arg Tyr Val Ala Arg Glu
1               5                  10                  15
Gln Ser Cys Arg Arg Pro Asn Ala Gln Arg Phe Gly Ile Ser Asn
            20                  25                  30
```

<210> SEQ ID NO 91
<211> LENGTH: 37
<212> TYPE: PRT
<213> ORGANISM: Artificial Sequence
<220> FEATURE:
<223> OTHER INFORMATION: Der p 1 derived hypoallergenic molecule

<400> SEQUENCE: 91

```
Arg Glu Gln Ser Cys Arg Arg Pro Asn Ala Gln Arg Phe Gly Ile Ser
1               5                  10                  15
Asn Tyr Cys Gln Ile Tyr Pro Pro Asn Val Asn Lys Ile Arg Glu Ala
            20                  25                  30
Leu Ala Gln Thr His
        35
```

<210> SEQ ID NO 92
<211> LENGTH: 31
<212> TYPE: PRT
<213> ORGANISM: Artificial Sequence
<220> FEATURE:
<223> OTHER INFORMATION: Der p 1 derived hypoallergenic molecule

<400> SEQUENCE: 92

```
Lys Asp Leu Asp Ala Phe Arg His Tyr Asp Gly Arg Thr Ile Ile Gln
1               5                  10                  15
Arg Asp Asn Gly Tyr Gln Pro Asn Tyr His Ala Val Asn Ile Val
            20                  25                  30
```

<210> SEQ ID NO 93
<211> LENGTH: 33
<212> TYPE: PRT

-continued

<213> ORGANISM: Artificial Sequence
<220> FEATURE:
<223> OTHER INFORMATION: Der p 1 derived hypoallergenic molecule

<400> SEQUENCE: 93

```
Gly Arg Thr Ile Ile Gln Arg Asp Asn Gly Tyr Gln Pro Asn Tyr His
1               5                   10                  15

Ala Val Asn Ile Val Gly Tyr Ser Asn Ala Gln Gly Val Asp Tyr Trp
                20                  25                  30

Ile
```

<210> SEQ ID NO 94
<211> LENGTH: 34
<212> TYPE: PRT
<213> ORGANISM: Artificial Sequence
<220> FEATURE:
<223> OTHER INFORMATION: Der p 1 derived hypoallergenic molecule

<400> SEQUENCE: 94

```
Val Gly Tyr Ser Asn Ala Gln Gly Val Asp Tyr Trp Ile Val Arg Asn
1               5                   10                  15

Ser Trp Asp Thr Asn Trp Gly Asp Asn Gly Tyr Gly Tyr Phe Ala Ala
                20                  25                  30

Asn Ile
```

<210> SEQ ID NO 95
<211> LENGTH: 35
<212> TYPE: PRT
<213> ORGANISM: Artificial Sequence
<220> FEATURE:
<223> OTHER INFORMATION: Der p 1 derived hypoallergenic molecule

<400> SEQUENCE: 95

```
Val Arg Asn Ser Trp Asp Thr Asn Trp Gly Asp Asn Gly Tyr Gly Tyr
1               5                   10                  15

Phe Ala Ala Asn Ile Asp Leu Met Met Ile Glu Glu Tyr Pro Tyr Val
                20                  25                  30

Val Ile Leu
        35
```

<210> SEQ ID NO 96
<211> LENGTH: 33
<212> TYPE: PRT
<213> ORGANISM: Artificial Sequence
<220> FEATURE:
<223> OTHER INFORMATION: Der p 2 derived hypoallergenic molecule

<400> SEQUENCE: 96

```
Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
                20                  25                  30

Lys
```

<210> SEQ ID NO 97
<211> LENGTH: 31
<212> TYPE: PRT
<213> ORGANISM: Artificial Sequence
<220> FEATURE:
<223> OTHER INFORMATION: Der p 2 derived hypoallergenic molecule

<400> SEQUENCE: 97

```
Cys His Gly Ser Glu Pro Cys Ile Ile His Arg Gly Lys Pro Phe Gln
1               5                   10                  15

Leu Glu Ala Val Phe Glu Ala Asn Gln Asn Ser Lys Thr Ala Lys
            20                  25                  30
```

<210> SEQ ID NO 98
<211> LENGTH: 32
<212> TYPE: PRT
<213> ORGANISM: Artificial Sequence
<220> FEATURE:
<223> OTHER INFORMATION: Der p 2 derived hypoallergenic molecule

<400> SEQUENCE: 98

```
Glu Ala Asn Gln Asn Ser Lys Thr Ala Lys Ile Glu Ile Lys Ala Ser
1               5                   10                  15

Ile Glu Gly Leu Glu Val Asp Val Pro Gly Ile Asp Pro Asn Ala Cys
            20                  25                  30
```

<210> SEQ ID NO 99
<211> LENGTH: 42
<212> TYPE: PRT
<213> ORGANISM: Artificial Sequence
<220> FEATURE:
<223> OTHER INFORMATION: Der p 2 derived hypoallergenic molecule

<400> SEQUENCE: 99

```
Glu Val Asp Val Pro Gly Ile Asp Pro Asn Ala Cys His Tyr Met Lys
1               5                   10                  15

Cys Pro Leu Val Lys Gly Gln Gln Tyr Asp Ile Lys Tyr Thr Trp Ile
            20                  25                  30

Val Pro Lys Ile Ala Pro Lys Ser Glu Asn
            35                  40
```

<210> SEQ ID NO 100
<211> LENGTH: 32
<212> TYPE: PRT
<213> ORGANISM: Artificial Sequence
<220> FEATURE:
<223> OTHER INFORMATION: Der p 2 derived hypoallergenic molecule

<400> SEQUENCE: 100

```
Ala Pro Lys Ser Glu Asn Val Val Val Thr Val Lys Val Met Gly Asp
1               5                   10                  15

Asn Gly Val Leu Ala Cys Ala Ile Ala Thr His Ala Lys Ile Arg Asp
            20                  25                  30
```

<210> SEQ ID NO 101
<211> LENGTH: 35
<212> TYPE: PRT
<213> ORGANISM: Artificial Sequence
<220> FEATURE:
<223> OTHER INFORMATION: Der p 5 derived hypoallergenic molecule

<400> SEQUENCE: 101

```
Met Glu Asp Lys Lys His Asp Tyr Gln Asn Glu Phe Asp Phe Leu Leu
1               5                   10                  15

Met Glu Arg Ile His Glu Gln Ile Lys Lys Gly Glu Leu Ala Leu Phe
            20                  25                  30

Tyr Leu Gln
        35
```

<210> SEQ ID NO 102
<211> LENGTH: 36

```
<212> TYPE: PRT
<213> ORGANISM: Artificial Sequence
<220> FEATURE:
<223> OTHER INFORMATION: Der p 5 derived hypoallergenic molecule

<400> SEQUENCE: 102

Lys Lys Gly Glu Leu Ala Leu Phe Tyr Leu Gln Glu Gln Ile Asn His
1               5                   10                  15

Phe Glu Glu Lys Pro Thr Lys Glu Met Lys Asp Lys Ile Val Ala Glu
            20                  25                  30

Met Asp Thr Ile
        35

<210> SEQ ID NO 103
<211> LENGTH: 31
<212> TYPE: PRT
<213> ORGANISM: Artificial Sequence
<220> FEATURE:
<223> OTHER INFORMATION: Der p 5 derived hypoallergenic molecule

<400> SEQUENCE: 103

Asp Gly Val Arg Gly Val Leu Asp Arg Leu Met Gln Arg Lys Asp Leu
1               5                   10                  15

Asp Ile Phe Glu Gln Tyr Asn Leu Glu Met Ala Lys Lys Ser Gly
            20                  25                  30

<210> SEQ ID NO 104
<211> LENGTH: 36
<212> TYPE: PRT
<213> ORGANISM: Artificial Sequence
<220> FEATURE:
<223> OTHER INFORMATION: Der p 5 derived hypoallergenic molecule

<400> SEQUENCE: 104

Asp Leu Asp Ile Phe Glu Gln Tyr Asn Leu Glu Met Ala Lys Lys Ser
1               5                   10                  15

Gly Asp Ile Leu Glu Arg Asp Leu Lys Lys Glu Glu Ala Arg Val Lys
            20                  25                  30

Lys Ile Glu Val
        35

<210> SEQ ID NO 105
<211> LENGTH: 30
<212> TYPE: PRT
<213> ORGANISM: Artificial Sequence
<220> FEATURE:
<223> OTHER INFORMATION: Der p 7 derived hypoallergenic molecule

<400> SEQUENCE: 105

Asp Pro Ile His Tyr Asp Lys Ile Thr Glu Glu Ile Asn Lys Ala Val
1               5                   10                  15

Asp Glu Ala Val Ala Ala Ile Glu Lys Ser Glu Thr Phe Asp
            20                  25                  30

<210> SEQ ID NO 106
<211> LENGTH: 31
<212> TYPE: PRT
<213> ORGANISM: Artificial Sequence
<220> FEATURE:
<223> OTHER INFORMATION: Der p 7 derived hypoallergenic molecule

<400> SEQUENCE: 106

Val Ala Ala Ile Glu Lys Ser Glu Thr Phe Asp Pro Met Lys Val Pro
1               5                   10                  15
```

```
Asp His Ser Asp Lys Phe Glu Arg His Ile Gly Ile Ile Asp Leu
            20                  25                  30

<210> SEQ ID NO 107
<211> LENGTH: 31
<212> TYPE: PRT
<213> ORGANISM: Artificial Sequence
<220> FEATURE:
<223> OTHER INFORMATION: Der p 7 derived hypoallergenic molecule

<400> SEQUENCE: 107

Leu Lys Gly Glu Leu Asp Met Arg Asn Ile Gln Val Arg Gly Leu Lys
1               5                   10                  15

Gln Met Lys Arg Val Gly Asp Ala Asn Val Lys Ser Glu Asp Gly
            20                  25                  30

<210> SEQ ID NO 108
<211> LENGTH: 36
<212> TYPE: PRT
<213> ORGANISM: Artificial Sequence
<220> FEATURE:
<223> OTHER INFORMATION: Der p 7 derived hypoallergenic molecule

<400> SEQUENCE: 108

Val His Asp Asp Val Val Ser Met Glu Tyr Asp Leu Ala Tyr Lys Leu
1               5                   10                  15

Gly Asp Leu His Pro Asn Thr His Val Ile Ser Asp Ile Gln Asp Phe
            20                  25                  30

Val Val Glu Leu
        35

<210> SEQ ID NO 109
<211> LENGTH: 31
<212> TYPE: PRT
<213> ORGANISM: Artificial Sequence
<220> FEATURE:
<223> OTHER INFORMATION: Der p 7 derived hypoallergenic molecule

<400> SEQUENCE: 109

Leu Ser Leu Glu Val Ser Glu Glu Gly Asn Met Thr Leu Thr Ser Phe
1               5                   10                  15

Glu Val Arg Gln Phe Ala Asn Val Val Asn His Ile Gly Gly Leu
            20                  25                  30

<210> SEQ ID NO 110
<211> LENGTH: 34
<212> TYPE: PRT
<213> ORGANISM: Artificial Sequence
<220> FEATURE:
<223> OTHER INFORMATION: Der p 7 derived hypoallergenic molecule

<400> SEQUENCE: 110

Leu Ser Asp Val Leu Thr Ala Ile Phe Gln Asp Thr Val Arg Ala Glu
1               5                   10                  15

Met Thr Lys Val Leu Ala Pro Ala Phe Lys Lys Glu Leu Glu Arg Asn
            20                  25                  30

Asn Gln

<210> SEQ ID NO 111
<211> LENGTH: 35
<212> TYPE: PRT
<213> ORGANISM: Artificial Sequence
<220> FEATURE:
```

<223> OTHER INFORMATION: Der p 10 derived hypoallergenic molecule

<400> SEQUENCE: 111

Met Glu Ala Ile Lys Lys Met Gln Ala Met Lys Leu Glu Lys Asp
1               5                   10                  15

Asn Ala Ile Asp Arg Ala Glu Ile Ala Glu Gln Lys Ala Arg Asp Ala
            20                  25                  30

Asn Leu Arg
        35

<210> SEQ ID NO 112
<211> LENGTH: 35
<212> TYPE: PRT
<213> ORGANISM: Artificial Sequence
<220> FEATURE:
<223> OTHER INFORMATION: Der p 10 derived hypoallergenic molecule

<400> SEQUENCE: 112

Ala Glu Lys Ser Glu Glu Glu Val Arg Ala Leu Gln Lys Lys Ile Gln
1               5                   10                  15

Gln Ile Glu Asn Glu Leu Asp Gln Val Gln Glu Gln Leu Ser Ala Ala
            20                  25                  30

Asn Thr Lys
        35

<210> SEQ ID NO 113
<211> LENGTH: 40
<212> TYPE: PRT
<213> ORGANISM: Artificial Sequence
<220> FEATURE:
<223> OTHER INFORMATION: Der p 10 derived hypoallergenic molecule

<400> SEQUENCE: 113

Leu Glu Glu Lys Glu Lys Ala Leu Gln Thr Ala Glu Gly Asp Val Ala
1               5                   10                  15

Ala Leu Asn Arg Arg Ile Gln Leu Ile Glu Glu Asp Leu Glu Arg Ser
            20                  25                  30

Glu Glu Arg Leu Lys Ile Ala Thr
        35                  40

<210> SEQ ID NO 114
<211> LENGTH: 35
<212> TYPE: PRT
<213> ORGANISM: Artificial Sequence
<220> FEATURE:
<223> OTHER INFORMATION: Der p 10 derived hypoallergenic molecule

<400> SEQUENCE: 114

Ala Lys Leu Glu Glu Ala Ser Gln Ser Ala Asp Glu Ser Glu Arg Met
1               5                   10                  15

Arg Lys Met Leu Glu His Arg Ser Ile Thr Asp Glu Glu Arg Met Glu
            20                  25                  30

Gly Leu Glu
        35

<210> SEQ ID NO 115
<211> LENGTH: 31
<212> TYPE: PRT
<213> ORGANISM: Artificial Sequence
<220> FEATURE:
<223> OTHER INFORMATION: Der p 10 derived hypoallergenic molecule

<400> SEQUENCE: 115

Arg Met Glu Gly Leu Glu Asn Gln Leu Lys Glu Ala Arg Met Met Ala
1               5                   10                  15

Glu Asp Ala Asp Arg Lys Tyr Asp Glu Val Ala Arg Lys Leu Ala
            20                  25                  30

<210> SEQ ID NO 116
<211> LENGTH: 31
<212> TYPE: PRT
<213> ORGANISM: Artificial Sequence
<220> FEATURE:
<223> OTHER INFORMATION: Der p 10 derived hypoallergenic molecule

<400> SEQUENCE: 116

Asp Leu Glu Arg Ala Glu Glu Arg Ala Glu Thr Gly Glu Ser Lys Ile
1               5                   10                  15

Val Glu Leu Glu Glu Glu Leu Arg Val Val Gly Asn Asn Leu Lys
            20                  25                  30

<210> SEQ ID NO 117
<211> LENGTH: 41
<212> TYPE: PRT
<213> ORGANISM: Artificial Sequence
<220> FEATURE:
<223> OTHER INFORMATION: Der p 10 derived hypoallergenic molecule

<400> SEQUENCE: 117

Ser Glu Glu Lys Ala Gln Gln Arg Glu Ala His Glu Gln Gln Ile
1               5                   10                  15

Arg Ile Met Thr Thr Lys Leu Lys Glu Ala Glu Ala Arg Ala Glu Phe
            20                  25                  30

Ala Glu Arg Ser Val Gln Lys Leu Gln
        35                  40

<210> SEQ ID NO 118
<211> LENGTH: 35
<212> TYPE: PRT
<213> ORGANISM: Artificial Sequence
<220> FEATURE:
<223> OTHER INFORMATION: Der p 10 derived hypoallergenic molecule

<400> SEQUENCE: 118

Gln Lys Glu Val Asp Arg Leu Glu Asp Glu Leu Val His Glu Lys Glu
1               5                   10                  15

Lys Tyr Lys Ser Ile Ser Asp Glu Leu Asp Gln Thr Phe Ala Glu Leu
            20                  25                  30

Thr Gly Tyr
        35

<210> SEQ ID NO 119
<211> LENGTH: 35
<212> TYPE: PRT
<213> ORGANISM: Artificial Sequence
<220> FEATURE:
<223> OTHER INFORMATION: Der p 21 derived hypoallergenic molecule

<400> SEQUENCE: 119

Met Phe Ile Val Gly Asp Lys Lys Glu Asp Trp Arg Met Ala Phe
1               5                   10                  15

Asp Arg Leu Met Met Glu Glu Leu Glu Thr Lys Ile Asp Gln Val Glu
            20                  25                  30

Lys Gly Leu
        35

-continued

<210> SEQ ID NO 120
<211> LENGTH: 37
<212> TYPE: PRT
<213> ORGANISM: Artificial Sequence
<220> FEATURE:
<223> OTHER INFORMATION: Der p 21 derived hypoallergenic molecule

<400> SEQUENCE: 120

Leu His Leu Ser Glu Gln Tyr Lys Glu Leu Glu Lys Thr Lys Ser Lys
1               5                   10                  15

Glu Leu Lys Glu Gln Ile Leu Arg Glu Leu Thr Ile Gly Glu Asn Phe
            20                  25                  30

Met Lys Gly Ala Leu
        35

<210> SEQ ID NO 121
<211> LENGTH: 31
<212> TYPE: PRT
<213> ORGANISM: Artificial Sequence
<220> FEATURE:
<223> OTHER INFORMATION: Der p 21 derived hypoallergenic molecule

<400> SEQUENCE: 121

Gly Ala Leu Lys Phe Phe Glu Met Glu Ala Lys Arg Thr Asp Leu Asn
1               5                   10                  15

Met Phe Glu Arg Tyr Asn Tyr Glu Phe Ala Leu Glu Ser Ile Lys
            20                  25                  30

<210> SEQ ID NO 122
<211> LENGTH: 33
<212> TYPE: PRT
<213> ORGANISM: Artificial Sequence
<220> FEATURE:
<223> OTHER INFORMATION: Der p 21 derived hypoallergenic molecule

<400> SEQUENCE: 122

Tyr Asn Tyr Glu Phe Ala Leu Glu Ser Ile Lys Leu Leu Ile Lys Lys
1               5                   10                  15

Leu Asp Glu Leu Ala Lys Lys Val Lys Ala Val Asn Pro Asp Glu Tyr
            20                  25                  30

Tyr

<210> SEQ ID NO 123
<211> LENGTH: 32
<212> TYPE: PRT
<213> ORGANISM: Artificial Sequence
<220> FEATURE:
<223> OTHER INFORMATION: Clone 30 derived hypoallergenic molecule

<400> SEQUENCE: 123

Met Ala Asn Asp Asn Asp Asp Pro Thr Thr Thr Val His Pro Thr
1               5                   10                  15

Thr Thr Glu Gln Pro Asp Asp Lys Phe Glu Cys Pro Ser Arg Phe Gly
            20                  25                  30

<210> SEQ ID NO 124
<211> LENGTH: 34
<212> TYPE: PRT
<213> ORGANISM: Artificial Sequence
<220> FEATURE:
<223> OTHER INFORMATION: Clone 30 derived hypoallergenic molecule

<400> SEQUENCE: 124

```
Pro Thr Thr Thr Glu Gln Pro Asp Asp Lys Phe Glu Cys Pro Ser Arg
1               5                   10                  15

Phe Gly Tyr Phe Ala Asp Pro Lys Asp Pro His Lys Phe Tyr Ile Cys
            20                  25                  30

Ser Asn

<210> SEQ ID NO 125
<211> LENGTH: 39
<212> TYPE: PRT
<213> ORGANISM: Artificial Sequence
<220> FEATURE:
<223> OTHER INFORMATION: Clone 30 derived hypoallergenic molecule

<400> SEQUENCE: 125

Gly Tyr Phe Ala Asp Pro Lys Asp Pro His Lys Phe Tyr Ile Cys Ser
1               5                   10                  15

Asn Trp Glu Ala Val His Lys Asp Cys Pro Gly Asn Thr Arg Trp Asn
            20                  25                  30

Glu Asp Glu Glu Thr Cys Thr
            35

<210> SEQ ID NO 126
<211> LENGTH: 30
<212> TYPE: PRT
<213> ORGANISM: Artificial Sequence
<220> FEATURE:
<223> OTHER INFORMATION: Bet v 1 derived hypoallergenic molecule

<400> SEQUENCE: 126

Leu Phe Pro Lys Val Ala Pro Gln Ala Ile Ser Ser Val Glu Asn Ile
1               5                   10                  15

Glu Gly Asn Gly Gly Pro Gly Thr Ile Lys Lys Ile Ser Phe
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: Bet v 1 derived hypoallergenic molecule

<400> SEQUENCE: 127

Gly Pro Gly Thr Ile Lys Lys Ile Ser Phe Pro Glu Gly Phe Pro Phe
1               5                   10                  15

Lys Tyr Val Lys Asp Arg Val Asp Glu Val Asp His Thr Asn
            20                  25                  30

<210> SEQ ID NO 128
<211> LENGTH: 30
<212> TYPE: PRT
<213> ORGANISM: Artificial Sequence
<220> FEATURE:
<223> OTHER INFORMATION: Bet v 1 derived hypoallergenic molecule

<400> SEQUENCE: 128

Val Asp His Thr Asn Phe Lys Tyr Asn Tyr Ser Val Ile Glu Gly Gly
1               5                   10                  15

Pro Ile Gly Asp Thr Leu Glu Lys Ile Ser Asn Glu Ile Lys
            20                  25                  30

<210> SEQ ID NO 129
<211> LENGTH: 35
```

```
<212> TYPE: PRT
<213> ORGANISM: Artificial Sequence
<220> FEATURE:
<223> OTHER INFORMATION: Fel d 1 chain 1 derived hypoallergenic molecule

<400> SEQUENCE: 129

Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
            20                  25                  30

Val Val Cys
        35

<210> SEQ ID NO 130
<211> LENGTH: 36
<212> TYPE: PRT
<213> ORGANISM: Artificial Sequence
<220> FEATURE:
<223> OTHER INFORMATION: Fel d 1 chain 1 derived hypoallergenic molecule

<400> SEQUENCE: 130

Leu Glu Asn Ala Arg Ile Leu Lys Asn Cys Val Asp Ala Lys Met Thr
1               5                   10                  15

Glu Glu Asp Lys Glu Asn Ala Leu Ser Leu Leu Asp Lys Ile Tyr Thr
            20                  25                  30

Ser Pro Leu Cys
        35

<210> SEQ ID NO 131
<211> LENGTH: 35
<212> TYPE: PRT
<213> ORGANISM: Artificial Sequence
<220> FEATURE:
<223> OTHER INFORMATION: Fel d 1 chain 2 derived hypoallergenic molecule

<400> SEQUENCE: 131

Val Lys Met Ala Ile Thr Cys Pro Ile Phe Tyr Asp Val Phe Phe Ala
1               5                   10                  15

Val Ala Asn Gly Asn Glu Leu Leu Leu Asp Leu Ser Leu Thr Lys Val
            20                  25                  30

Asn Ala Cys
        35

<210> SEQ ID NO 132
<211> LENGTH: 30
<212> TYPE: PRT
<213> ORGANISM: Artificial Sequence
<220> FEATURE:
<223> OTHER INFORMATION: Fel d 1 chain 2 derived hypoallergenic molecule

<400> SEQUENCE: 132

Thr Glu Pro Glu Arg Thr Ala Met Lys Lys Ile Gln Asp Cys Tyr Val
1               5                   10                  15

Glu Asn Gly Leu Ile Ser Arg Val Leu Asp Gly Leu Val Cys
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: Fel d 1 chain 2 derived hypoallergenic molecule

<400> SEQUENCE: 133
```

```
Cys Met Thr Thr Ile Ser Ser Lys Asp Cys Met Gly Glu Ala Val
1               5                   10                  15

Gln Asn Thr Val Glu Asp Leu Lys Leu Asn Thr Leu Gly Arg
            20                  25                  30
```

<210> SEQ ID NO 134
<211> LENGTH: 32
<212> TYPE: PRT
<213> ORGANISM: Artificial Sequence
<220> FEATURE:
<223> OTHER INFORMATION: Phl p 5 derived hypoallergenic molecule

<400> SEQUENCE: 134

```
Cys Gly Ala Ala Ser Asn Lys Ala Phe Ala Glu Gly Leu Ser Gly Glu
1               5                   10                  15

Pro Lys Gly Ala Ala Glu Ser Ser Lys Ala Ala Leu Thr Ser Lys
            20                  25                  30
```

<210> SEQ ID NO 135
<211> LENGTH: 34
<212> TYPE: PRT
<213> ORGANISM: Artificial Sequence
<220> FEATURE:
<223> OTHER INFORMATION: Phl p 5 derived hypoallergenic molecule

<400> SEQUENCE: 135

```
Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Glu Ala Ala Pro Ala Gly
            20                  25                  30

Lys Cys
```

<210> SEQ ID NO 136
<211> LENGTH: 32
<212> TYPE: PRT
<213> ORGANISM: Artificial Sequence
<220> FEATURE:
<223> OTHER INFORMATION: Phl p 5 derived hypoallergenic molecule

<400> SEQUENCE: 136

```
Ala Tyr Lys Leu Ala Tyr Lys Thr Ala Glu Gly Ala Thr Pro Glu Ala
1               5                   10                  15

Lys Tyr Asp Ala Tyr Val Ala Thr Leu Ser Glu Ala Leu Arg Ile Cys
            20                  25                  30
```

<210> SEQ ID NO 137
<211> LENGTH: 31
<212> TYPE: PRT
<213> ORGANISM: Artificial Sequence
<220> FEATURE:
<223> OTHER INFORMATION: Phl p 5 derived hypoallergenic molecule

<400> SEQUENCE: 137

```
Cys Glu Ala Ala Phe Asn Asp Ala Ile Lys Ala Ser Thr Gly Gly Ala
1               5                   10                  15

Tyr Glu Ser Tyr Lys Phe Ile Pro Ala Leu Glu Ala Ala Val Lys
            20                  25                  30
```

<210> SEQ ID NO 138
<211> LENGTH: 33
<212> TYPE: PRT
<213> ORGANISM: Artificial Sequence
<220> FEATURE:

<223> OTHER INFORMATION: Phl p 5 derived hypoallergenic molecule

<400> SEQUENCE: 138

Thr Val Ala Thr Ala Pro Glu Val Lys Tyr Thr Val Phe Glu Thr Ala
1               5                   10                  15

Leu Lys Lys Ala Ile Thr Ala Met Ser Glu Ala Gln Lys Ala Ala Lys
            20                  25                  30

Cys

<210> SEQ ID NO 139
<211> LENGTH: 38
<212> TYPE: PRT
<213> ORGANISM: Artificial Sequence
<220> FEATURE:
<223> OTHER INFORMATION: Phl p 5 derived hypoallergenic molecule

<400> SEQUENCE: 139

Cys Ala Glu Glu Val Lys Val Ile Pro Ala Gly Glu Leu Gln Val Ile
1               5                   10                  15

Glu Lys Val Asp Ala Ala Phe Lys Val Ala Ala Thr Ala Ala Asn Ala
            20                  25                  30

Ala Pro Ala Asn Asp Lys
            35

<210> SEQ ID NO 140
<211> LENGTH: 70
<212> TYPE: PRT
<213> ORGANISM: Artificial Sequence
<220> FEATURE:
<223> OTHER INFORMATION: Clone 30 Dermatophagoides pteronyssinus
      allergen

<400> SEQUENCE: 140

Met Ala Asn Asp Asn Asp Asp Pro Thr Thr Thr Val His Pro Thr
1               5                   10                  15

Thr Thr Glu Gln Pro Asp Asp Lys Phe Glu Cys Pro Ser Arg Phe Gly
            20                  25                  30

Tyr Phe Ala Asp Pro Lys Asp Pro His Lys Pro Tyr Ile Cys Ser Asn
        35                  40                  45

Trp Glu Ala Val His Lys Asp Cys Pro Gly Asn Thr Arg Trp Asn Glu
    50                  55                  60

Asp Glu Glu Thr Cys Thr
65                  70

<210> SEQ ID NO 141
<211> LENGTH: 37
<212> TYPE: PRT
<213> ORGANISM: Artificial Sequence
<220> FEATURE:
<223> OTHER INFORMATION: Phl p 5 derived peptide

<400> SEQUENCE: 141

Cys Phe Val Ala Thr Phe Gly Ala Ala Ser Asn Lys Ala Phe Ala Glu
1               5                   10                  15

Gly Leu Ser Gly Glu Pro Lys Gly Ala Ala Glu Ser Ser Ser Lys Ala
            20                  25                  30

Ala Leu Thr Ser Lys
            35

<210> SEQ ID NO 142
<211> LENGTH: 29

```
<212> TYPE: PRT
<213> ORGANISM: Artificial Sequence
<220> FEATURE:
<223> OTHER INFORMATION: Phl p 5 derived peptide

<400> SEQUENCE: 142

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Glu Ala Cys
            20                  25

<210> SEQ ID NO 143
<211> LENGTH: 41
<212> TYPE: PRT
<213> ORGANISM: Artificial Sequence
<220> FEATURE:
<223> OTHER INFORMATION: Der p 1 Fragment

<400> SEQUENCE: 143

Thr Asn Ala Cys Ser Ile Asn Gly Asn Ala Pro Ala Glu Ile Asp Leu
1               5                   10                  15

Arg Gln Met Arg Thr Val Thr Pro Ile Arg Met Gln Gly Gly Cys Gly
            20                  25                  30

Ser Cys Trp Ala Phe Ser Gly Val Ala
            35                  40

<210> SEQ ID NO 144
<211> LENGTH: 43
<212> TYPE: PRT
<213> ORGANISM: Artificial Sequence
<220> FEATURE:
<223> OTHER INFORMATION: Der p 1 Fragment

<400> SEQUENCE: 144

Ala Thr Glu Ser Ala Tyr Leu Ala Tyr Arg Asn Gln Ser Leu Asp Leu
1               5                   10                  15

Ala Glu Gln Glu Leu Val Asp Cys Ala Ser Gln His Gly Cys His Gly
            20                  25                  30

Asp Thr Ile Pro Arg Gly Ile Glu Tyr Ile Gln
            35                  40

<210> SEQ ID NO 145
<211> LENGTH: 30
<212> TYPE: PRT
<213> ORGANISM: Artificial Sequence
<220> FEATURE:
<223> OTHER INFORMATION: Der p 1 Fragment

<400> SEQUENCE: 145

Met Gln Gly Gly Cys Gly Ser Cys Trp Ala Phe Ser Gly Val Ala Ala
1               5                   10                  15

Thr Glu Ser Ala Tyr Leu Ala Tyr Arg Asn Gln Ser Leu Asp
            20                  25                  30

<210> SEQ ID NO 146
<211> LENGTH: 29
<212> TYPE: PRT
<213> ORGANISM: Artificial Sequence
<220> FEATURE:
<223> OTHER INFORMATION: Der p 23 Fragment

<400> SEQUENCE: 146

Gly Tyr Phe Ala Asp Pro Lys Asp Pro His Lys Phe Tyr Ile Cys Ser
1               5                   10                  15
```

Asn Trp Glu Ala Val His Lys Asp Cys Pro Gly Asn Thr
            20                  25

<210> SEQ ID NO 147
<211> LENGTH: 29
<212> TYPE: PRT
<213> ORGANISM: Artificial Sequence
<220> FEATURE:
<223> OTHER INFORMATION: Der p 23 Fragment

<400> SEQUENCE: 147

Lys Phe Tyr Ile Cys Ser Asn Trp Glu Ala Val His Lys Asp Cys Pro
1               5                   10                  15

Gly Asn Thr Arg Trp Asn Glu Asp Glu Glu Thr Cys Thr
            20                  25

<210> SEQ ID NO 148
<211> LENGTH: 39
<212> TYPE: PRT
<213> ORGANISM: Artificial Sequence
<220> FEATURE:
<223> OTHER INFORMATION: Der p 23 Fragment

<400> SEQUENCE: 148

Gly Tyr Phe Ala Asp Pro Lys Asp Pro His Lys Phe Tyr Ile Ser Ser
1               5                   10                  15

Asn Trp Glu Ala Val His Lys Asp Ser Pro Gly Asn Thr Arg Trp Asn
            20                  25                  30

Glu Asp Glu Glu Thr Ser Thr
        35

<210> SEQ ID NO 149
<211> LENGTH: 317
<212> TYPE: PRT
<213> ORGANISM: Artificial Sequence
<220> FEATURE:
<223> OTHER INFORMATION: Synthetic Peptide

<400> SEQUENCE: 149

His Gly Ser Glu Pro Cys Ile Ile His Arg Gly Lys Pro Phe Gln Leu
1               5                   10                  15

Glu Ala Val Phe Glu Ala Asn Gln Asn Ser Lys Thr Ala Lys His Gly
            20                  25                  30

Ser Glu Pro Cys Ile Ile His Arg Gly Lys Pro Phe Gln Leu Glu Ala
        35                  40                  45

Val Phe Glu Ala Asn Gln Asn Ser Lys Thr Ala Lys Gly Gly Trp Ser
    50                  55                  60

Ser Lys Pro Arg Lys Gly Met Gly Thr Asn Leu Ser Val Pro Asn Pro
65                  70                  75                  80

Leu Gly Phe Phe Pro Asp His Gln Leu Asp Pro Ala Phe Gly Ala Asn
                85                  90                  95

Ser Asn Asn Pro Asp Trp Asp Phe Asn Pro Ile Lys Asp His Trp Pro
            100                 105                 110

Ala Ala Asn Gln Val Gly Val Gly Ala Phe Gly Pro Gly Leu Thr Pro
        115                 120                 125

Pro His Gly Gly Ile Leu Gly Trp Ser Pro Gln Ala Gln Gly Ile Leu
    130                 135                 140

Thr Thr Val Ser Thr Ile Pro Pro Pro Ala Ser Thr Asn Arg Gln Ser
145                 150                 155                 160

```
Gly Arg Gln Pro Thr Pro Ile Ser Pro Pro Leu Arg Asp Ser His Pro
            165                 170                 175

Gln Ala Met Gln Trp Asn Ser Thr Ala Phe His Gln Ala Leu Gln Asp
        180                 185                 190

Pro Arg Val Arg Gly Leu Tyr Phe Pro Ala Gly Gly Ser Ser Ser Gly
            195                 200                 205

Thr Val Asn Pro Ala Pro Asn Ile Ala Ser His Ile Ser Ser Ile Ser
210                 215                 220

Ala Arg Thr Gly Asp Pro Val Thr Asn Glu Val Asp Val Pro Gly Ile
225                 230                 235                 240

Asp Pro Asn Ala Cys His Tyr Met Lys Cys Pro Leu Val Lys Gly Gln
                245                 250                 255

Gln Tyr Asp Ile Lys Tyr Thr Trp Ile Val Pro Lys Ile Ala Pro Lys
            260                 265                 270

Ser Glu Asn Glu Val Asp Val Pro Gly Ile Asp Pro Asn Ala Cys His
            275                 280                 285

Tyr Met Lys Cys Pro Leu Val Lys Gly Gln Gln Tyr Asp Ile Lys Tyr
        290                 295                 300

Thr Trp Ile Val Pro Lys Ile Ala Pro Lys Ser Glu Asn
305                 310                 315

<210> SEQ ID NO 150
<211> LENGTH: 389
<212> TYPE: PRT
<213> ORGANISM: Artificial Sequence
<220> FEATURE:
<223> OTHER INFORMATION: Synthetic Peptide

<400> SEQUENCE: 150

His Gly Ser Glu Pro Cys Ile Ile His Arg Gly Lys Pro Phe Gln Leu
1               5                   10                  15

Glu Ala Val Phe Glu Ala Asn Gln Asn Ser Lys Thr Ala Lys His Gly
            20                  25                  30

Ser Glu Pro Cys Ile Ile His Arg Gly Lys Pro Phe Gln Leu Glu Ala
        35                  40                  45

Val Phe Glu Ala Asn Gln Asn Ser Lys Thr Ala Lys His Gly Ser Glu
    50                  55                  60

Pro Cys Ile Ile His Arg Gly Lys Pro Phe Gln Leu Glu Ala Val Phe
65                  70                  75                  80

Glu Ala Asn Gln Asn Ser Lys Thr Ala Lys Gly Gly Trp Ser Ser Lys
                85                  90                  95

Pro Arg Lys Gly Met Gly Thr Asn Leu Ser Val Pro Asn Pro Leu Gly
            100                 105                 110

Phe Phe Pro Asp His Gln Leu Asp Pro Ala Phe Gly Ala Asn Ser Asn
        115                 120                 125

Asn Pro Asp Trp Asp Phe Asn Pro Ile Lys Asp His Trp Pro Ala Ala
    130                 135                 140

Asn Gln Val Gly Val Gly Ala Phe Gly Pro Gly Leu Thr Pro Pro His
145                 150                 155                 160

Gly Gly Ile Leu Gly Trp Ser Pro Gln Ala Gln Gly Ile Leu Thr Thr
                165                 170                 175

Val Ser Thr Ile Pro Pro Pro Ala Ser Thr Asn Arg Gln Ser Gly Arg
            180                 185                 190

Gln Pro Thr Pro Ile Ser Pro Pro Leu Arg Asp Ser His Pro Gln Ala
        195                 200                 205
```

Met Gln Trp Asn Ser Thr Ala Phe His Gln Ala Leu Gln Asp Pro Arg
210                 215                 220

Val Arg Gly Leu Tyr Phe Pro Ala Gly Ser Ser Gly Thr Val
225                 230                 235                 240

Asn Pro Ala Pro Asn Ile Ala Ser His Ile Ser Ser Ile Ser Ala Arg
            245                 250                 255

Thr Gly Asp Pro Val Thr Asn Glu Val Asp Val Pro Gly Ile Asp Pro
                260                 265                 270

Asn Ala Cys His Tyr Met Lys Cys Pro Leu Val Lys Gly Gln Gln Tyr
            275                 280                 285

Asp Ile Lys Tyr Thr Trp Ile Val Pro Lys Ile Ala Pro Lys Ser Glu
290                 295                 300

Asn Glu Val Asp Val Pro Gly Ile Asp Pro Asn Ala Cys His Tyr Met
305                 310                 315                 320

Lys Cys Pro Leu Val Lys Gly Gln Gln Tyr Asp Ile Lys Tyr Thr Trp
                325                 330                 335

Ile Val Pro Lys Ile Ala Pro Lys Ser Glu Asn Glu Val Asp Val Pro
            340                 345                 350

Gly Ile Asp Pro Asn Ala Cys His Tyr Met Lys Cys Pro Leu Val Lys
                355                 360                 365

Gly Gln Gln Tyr Asp Ile Lys Tyr Thr Trp Ile Val Pro Lys Ile Ala
370                 375                 380

Pro Lys Ser Glu Asn
385

<210> SEQ ID NO 151
<211> LENGTH: 289
<212> TYPE: PRT
<213> ORGANISM: Artificial Sequence
<220> FEATURE:
<223> OTHER INFORMATION: Synthetic Peptide

<400> SEQUENCE: 151

Gly Tyr Phe Ala Asp Pro Lys Asp Pro His Lys Phe Tyr Ile Cys Ser
1               5                   10                  15

Asn Trp Glu Ala Val His Lys Asp Cys Pro Gly Asn Thr Gly Tyr Phe
            20                  25                  30

Ala Asp Pro Lys Asp Pro His Lys Phe Tyr Ile Cys Ser Asn Trp Glu
        35                  40                  45

Ala Val His Lys Asp Cys Pro Gly Asn Thr Gly Gly Trp Ser Ser Lys
    50                  55                  60

Pro Arg Lys Gly Met Gly Thr Asn Leu Ser Val Pro Asn Pro Leu Gly
65                  70                  75                  80

Phe Phe Pro Asp His Gln Leu Asp Pro Ala Phe Gly Ala Asn Ser Asn
                85                  90                  95

Asn Pro Asp Trp Asp Phe Asn Pro Ile Lys Asp His Trp Pro Ala Ala
            100                 105                 110

Asn Gln Val Gly Val Gly Ala Phe Gly Pro Gly Leu Thr Pro Pro His
        115                 120                 125

Gly Gly Ile Leu Gly Trp Ser Pro Gln Ala Gln Gly Ile Leu Thr Thr
130                 135                 140

Val Ser Thr Ile Pro Pro Ala Ser Thr Asn Arg Gln Ser Gly Arg
145                 150                 155                 160

Gln Pro Thr Pro Ile Ser Pro Pro Leu Arg Asp Ser His Pro Gln Ala
                165                 170                 175

```
Met Gln Trp Asn Ser Thr Ala Phe His Gln Ala Leu Gln Asp Pro Arg
            180                 185                 190

Val Arg Gly Leu Tyr Phe Pro Ala Gly Gly Ser Ser Gly Thr Val
        195                 200                 205

Asn Pro Ala Pro Asn Ile Ala Ser His Ile Ser Ser Ile Ser Ala Arg
210                 215                 220

Thr Gly Asp Pro Val Thr Asn Lys Phe Tyr Ile Cys Ser Asn Trp Glu
225                 230                 235                 240

Ala Val His Lys Asp Cys Pro Gly Asn Thr Arg Trp Asn Glu Asp Glu
            245                 250                 255

Glu Thr Cys Thr Lys Phe Tyr Ile Cys Ser Asn Trp Glu Ala Val His
        260                 265                 270

Lys Asp Cys Pro Gly Asn Thr Arg Trp Asn Glu Asp Glu Thr Cys
            275                 280                 285

Thr
```

<210> SEQ ID NO 152
<211> LENGTH: 329
<212> TYPE: PRT
<213> ORGANISM: Artificial Sequence
<220> FEATURE:
<223> OTHER INFORMATION: Synthetic Peptide

<400> SEQUENCE: 152

```
Gly Tyr Phe Ala Asp Pro Lys Asp Pro His Lys Phe Tyr Ile Ser Ser
1               5                   10                  15

Asn Trp Glu Ala Val His Lys Asp Ser Pro Gly Asn Thr Arg Trp Asn
            20                  25                  30

Glu Asp Glu Glu Thr Ser Thr Gly Tyr Phe Ala Asp Pro Lys Asp Pro
        35                  40                  45

His Lys Phe Tyr Ile Ser Ser Asn Trp Glu Ala Val His Lys Asp Ser
    50                  55                  60

Pro Gly Asn Thr Arg Trp Asn Glu Asp Glu Glu Thr Ser Thr Gly Gly
65                  70                  75                  80

Trp Ser Ser Lys Pro Arg Lys Gly Met Gly Thr Asn Leu Ser Val Pro
                85                  90                  95

Asn Pro Leu Gly Phe Phe Pro Asp His Gln Leu Asp Pro Ala Phe Gly
            100                 105                 110

Ala Asn Ser Asn Asn Pro Asp Trp Asp Phe Asn Pro Ile Lys Asp His
        115                 120                 125

Trp Pro Ala Ala Asn Gln Val Gly Val Gly Ala Phe Gly Pro Gly Leu
    130                 135                 140

Thr Pro Pro His Gly Gly Ile Leu Gly Trp Ser Pro Gln Ala Gln Gly
145                 150                 155                 160

Ile Leu Thr Thr Val Ser Thr Ile Pro Pro Pro Ala Ser Thr Asn Arg
                165                 170                 175

Gln Ser Gly Arg Gln Pro Thr Pro Ile Ser Pro Pro Leu Arg Asp Ser
            180                 185                 190

His Pro Gln Ala Met Gln Trp Asn Ser Thr Ala Phe His Gln Ala Leu
        195                 200                 205

Gln Asp Pro Arg Val Arg Gly Leu Tyr Phe Pro Ala Gly Gly Ser Ser
    210                 215                 220

Ser Gly Thr Val Asn Pro Ala Pro Asn Ile Ala Ser His Ile Ser Ser
225                 230                 235                 240

Ile Ser Ala Arg Thr Gly Asp Pro Val Thr Asn Gly Tyr Phe Ala Asp
```

-continued

```
                245                 250                 255
Pro Lys Asp Pro His Lys Phe Tyr Ile Ser Ser Asn Trp Glu Ala Val
            260                 265                 270

His Lys Asp Ser Pro Gly Asn Thr Arg Trp Asn Glu Asp Glu Glu Thr
        275                 280                 285

Ser Thr Gly Tyr Phe Ala Asp Pro Lys Asp Pro His Lys Phe Tyr Ile
    290                 295                 300

Ser Ser Asn Trp Glu Ala Val His Lys Asp Ser Pro Gly Asn Thr Arg
305                 310                 315                 320

Trp Asn Glu Asp Glu Glu Thr Ser Thr
                325
```

PEPTIDE CARRIER FUSION PROTEINS AS ALLERGY VACCINES

This application is a 35 U.S.C. §371 national stage patent application of international patent application PCT/EP12/61040, filed on Jun. 11, 2012, the text of which is incorporated by reference, and claims priority to European patent application 11169365.1, filed on Jun. 9, 2011, the text of which is also incorporated by reference.

The present invention relates to novel polypeptides and uses thereof.

Type I allergy is an IgE-mediated hypersensitivity disease affecting almost 25% of the population. It is based on the recognition of harmless airborne, insect, venom, food allergen and contact allergen antigens derived from per se harmless antigen sources such as pollen, insects, mold and animal proteins by specific immunoglobulin E. The crosslinking of effector cell-bound IgE antibodies leads to a release of inflammatory mediators (e.g., histamine, leucotrienes) and thus to the immediate symptoms of allergy (e.g., rhinoconjunctivitis, asthma, dermatitis, anaphylaxis). T-cell activation via IgE-dependent as well as IgE-independent mechanisms contributes to chronic allergic inflammation.

The probably only causative form of allergy treatment is allergen-specific immunotherapy, which is based on the repeated administration of increasing amounts of allergen extracts for most sources. Numerous clinical studies have documented the clinical efficacy of injection immunotherapy and there is evidence for several immunological mechanisms underlying this treatment. Due to the difficulty to prepare high quality allergen extracts for certain allergen sources and the fact that the administration of allergens to patients can cause severe side effects, allergen-specific immunotherapy can only be recommended for certain patients groups and disease manifestations. It is especially difficult to treat patients with co-sensitizations to several different allergen sources and patients suffering from severe disease manifestations such as allergic asthma. Allergic asthma is one of the most vigorous manifestations of allergy, because it severely affects the quality of daily life, causes a high rate of hospitality admissions and can manifest itself in serious, life-threatening forms requiring intensive care of the patient.

Allergen extracts prepared from natural allergen-sources are crude in nature, and it is impossible to influence the quality and amounts of individual allergens in such preparations by technical means. They also contain numerous undefined non-allergenic components, and several recent studies indicate the poor quality of such extracts and document their great heterogeneity.

In the last decade great progress has been made in the field of molecular allergen characterization using recombinant DNA technology. A large number of the most important disease-eliciting allergens has been characterized down to the molecular level, and recombinant allergens mimicking the epitope complexity of natural allergen extracts have been produced. Moreover, several research groups have used the knowledge regarding allergen structures to develop defined new allergy vaccines. Genetic engineering, synthetic peptide chemistry and conjugation of allergens with immunostimulatory DNA sequences have been used to reduce the allergenic activity of the new vaccines and thus the rate of therapy-induced side effects. First promising clinical studies were conducted with such allergen derivatives. Interestingly, it turned out that although IgE-reactivity of genetically engineered recombinant allergens and allergen-derived synthetic T-cell epitope-containing peptides could be strongly reduced or even abolished, these derivatives still could induce systemic side effects appearing several hours after injection. For example, it was reported that T-cell epitope peptides of the major cat allergen, Fel d 1, induced asthma and bronchial hyper reactivity several hours after intracutaneous injection, and there is strong evidence that this effect is T-cell mediated and MHC-restricted.

These results indicate that the removal of IgE-reactivity diminishes IgE-mediated side effects since no immediate reactions were recorded in the course of these immunotherapy studies. However, the allergen-specific T-cell epitopes which have been preserved in the recombinant allergen derivatives as well as in the peptide mixtures are responsible for the late side effects (e.g. very problematic or atopic dermatitis, chronic T-cell-mediated allergic skin manifestation). The side effects caused in the case of recombinant allergen-derivatives were relatively mild and in the case of the T-cell peptide vaccines may be overcome by adequate dosing. Both of the two new approaches therefore seem very promising for immunotherapy of allergic rhinoconjunctivitis but may have limitations when it comes to the treatment of severe forms of allergic asthma, where the induction of late side effects in the lung may be very problematic.

In order to administer and consequently to provoke an efficient immune response against peptides, polypeptides and proteins, adjuvants and/or carriers are regularly used. Complete Freund's adjuvant (CFA), for instance, is one of the most potent adjuvants available. There exists a need for vaccine compositions able to induce strong immune responses against peptides and polypeptides derived from allergens and of course of other antigens with or without the use of complete Freund's adjuvant. Further, while BSA has been used successfully as a carrier in animal models it may not be appropriate for use in human vaccine compositions because of the risk of adverse reactions such as the risk of transmitting prion disease (variant Creutzfeldt-Jakob disease). A further challenge to the development of an effective vaccine against allergens is the need for an immune response able to rapidly decrease allergens in an individual or animal. Therefore, high concentrations of allergen-specific antibodies in the blood, which are mainly of the IgG subtype, are needed. In mucosal surfaces IgA antibodies are also important.

Cholera toxin, a known carrier protein in the art, is also used regularly as an adjuvant. However, cholera toxin increases total and specific IgE antibody levels and leads to IgE-associated inflammatory reactions.

Due to the side effects provoked by most carrier proteins used for vaccination, there exists a need for carrier systems which are able to stimulate immune responses against allergens or other antigens, without using toxic adjuvants, without using poorly tolerated carrier proteins and, in certain situations, without stimulation of potentially pathologic immune responses. Novel carrier systems meeting these specifications can be used towards the formation of novel conjugates and compositions suitable for the treatment or prevention of diseases like allergic diseases.

In Bohle B. et al. (J. Immunol. 172 (11) (2004): 6642-6648) a recombinant fusion protein comprising an S-layer protein moiety and Bet v 1 moiety is described. This molecule comprises the native Bet v 1 allergen including Bet v 1-specific T cell epitopes.

WO 2004/004761 relates to virus like particles which are fused to an immunogen and which may be used for immunisation.

In WO 2004/003143 the use of fusion proteins comprising a virus like particle and an allergenic molecule as immunogen for vaccination is disclosed.

In WO 2007/140505 and Edlmayr et al. (J. Immunol. 182 (10) (2009) 6298-6306) the use of fusion proteins comprising various carrier molecules fused to allergen-derived peptides are described to induce allergen-specific IgG antibodies but these constructs do not exhibit an immunomodulatory effect which may be considered advantageous for allergic patients such as the induction of IL-10 or Th1 immunity. FIG. 4 of Edlmayr et al shows that KLH-fused peptides induce the Th2 cytokine IL-5 and VP1 fusion proteins do not induce IL-10 or IFN-gamma.

In Niespodziana et al (J. Allergy Clin. Immunol. 127 (6) (2011) 1562-1570) the use of fusion proteins each comprising Hepatitis B-derived PreS and two peptides derived from the major cat allergen Fel d 1 are described to induce allergen-specific IgG antibodies. However, no regimen suitable for vaccination of humans has been described and the peptides contained allergen-specific T cell epitopes.

It is an object of the present invention to provide medicaments and carriers which overcome the aforementioned drawbacks and allow an allergen vaccination with reduced side effects.

Therefore, the present invention relates to a polypeptide comprising at least three peptide fragments consisting of 10 to 50 consecutive amino acid residues of at least one wild-type allergen fused to the N- and C-terminus of a surface polypeptide of a virus of the hepadnaviridae family or at least one fragment of said surface polypeptide or comprising a surface polypeptide of a virus of the hepadnaviridae family or at least one fragment thereof fused N- and/or C-terminally to at least three peptides derived from at least one wild-type allergen.

In order to provoke an enhanced immune response against a molecule, in particular against an allergenic or hypoallergenic molecule according to the present invention, at least three peptide fragments derived from at least one wild-type allergen are fused (by genetic engineering) to a surface polypeptide of a virus of the hepadnaviridae family, preferably of a Hepatitis B virus, more preferably of a Hepatitis B PreS polypeptide, or at least one fragment thereof. It turned surprisingly out that in contrast to conventionally and regularly employed carrier proteins like KLH (Keyhole limpet hemocyanin) a surface polypeptide of a virus of the hepadnaviridae family, preferably of a Hepatitis B virus, more preferably of a Hepatitis B PreS polypeptide, or fragments thereof lead to an enhanced formation of antibodies directed to those peptides which are bound thereto.

Moreover, it turned out that allergen specific IgG antibodies induced by immunization with more than three properly selected allergen derived peptide fragments fused to the Hepatitis B PreS polypeptide are better focused to the IgE epitopes of the allergen while immunization with the wild-type allergen leads to IgG which are directed to all parts of the allergen—also those which are not IgE reactive. In an experiment normalized for IgG titers this leads to a better blocking capacity of PreS/peptide induced IgG compared to wild-type allergen induced (FIG. 12).

Also very surprisingly, it turned out that in cultures of human PBMCs fusion proteins of allergen derived peptide fragments to the Hepatitis B PreS polypeptide strongly induced the cytokines IL-10 and IFN-gamma, which have been attributed as positive indicators for a successful allergy immunotherapy. In contrast, induction of IL-10 and IFN-gamma was significantly lower with wild-type allergen, allergen derived peptide fragments alone or PreS alone (FIG. 10).

"Fused to the N- and C-terminus", as used herein, means that at least one peptide is fused to the N-terminus of a surface polypeptide of a virus of the hepadnaviridae family or at least one fragment of said surface polypeptide and at least one peptide is fused to the C-terminus of a surface polypeptide of a virus of the hepadnaviridae family or at least one fragment of said surface polypeptide. In a most simplest embodiment of the present invention a surface polypeptide of a virus of the hepadnaviridae family or at least one fragment of said surface polypeptide may comprise at the N-terminus one peptide and on the C-terminus two peptides or vice versa.

The polypeptide of the present invention preferably comprises at least four, more preferably at least five, even more preferably at least six, peptide fragments, preferably B cell binding peptides, derived from an allergen, whereby four peptides are most preferred.

According to a particularly preferred embodiment of the present invention the carrier protein is the Hepatitis B PreS polypeptide with the following amino acid sequence (SEQ ID No. 21):

```
GGWSSKPRKGMGTNLSVPNPLGFFPDHQLDPAFGANSNNPDWDFNPI

KDHWPAANQVGVGAFGPGLTPPHGGILGWSPQAQGILTTVSTIPPPA

STNRQSGRQPTPISPPLRDSHPQAMQWNSTAFHQALQDPRVRGLYFP

AGGSSSGTVNPAPNIASHISSISARTGDPVTN
```

It is also possible to use fragments Hepatitis B PreS1 or Hepatitis B PreS2 of the Hepatitis B PreS polypeptide. A fragment of the Hepatitis B PreS polypeptide preferably comprises or consists of at least 30, preferably at least 40, more preferably at least 50, consecutive amino acid residues of SEQ ID No. 21.

"Hypoallergenic" as used herein, refers to molecules with reduced or no allergenic potential (i.e. IgE reactivity determined with IgE binding assays known in the art). Such molecules have a decreased capacity to provoke allergic reactions in an individual compared to the wild-type protein from which these molecules are derived.

The at least three, preferably at least four, more preferably at least five, even more preferably at least six, peptide fragments fused to the N- and C-terminus of a surface polypeptide of a virus of the hepadnaviridae family or at least one fragment of said surface polypeptide comprise or consist of 10 to 50 consecutive amino acids, more preferably 15 to 50 consecutive amino acids, in particular 20-50 consecutive amino acids, of at least one wild-type allergen and exhibit preferably reduced IgE reactivity compared to the wild-type allergen from which the peptide fragments are derived from. These peptide fragments are preferably designed to exclude allergen-specific T-cell epitopes which may cause T-cell-mediated side effects. T-cell epitopes and molecules exhibiting reduced T-cell response may be determined and identified by methods known by the person skilled in the art (e.g., Bercovici N. et al. Clin Diagn Lab Immunol. (2000) 7:859-864).

The at least three peptide fragments comprising or consisting of 10 to 50 consecutive amino acids, more preferably 15 to 50 consecutive amino acids, in particular 20-50 consecutive amino acids, of at least one wild-type allergen can be derived from one and the same allergen. If two or more fragments are derived from the same allergen these two or more fragments are not adjacently located in the wild type allergen and/or have an order in the polypeptide of the present invention which does not correspond to the order in the wild type allergen.

The term "peptide fragment" as used herein means a part/fragment of a hypoallergenic polypeptide or fusion protein of the invention which is derived from the primary structure of a wild-type allergen and comprise or consist of 10 to 50 consecutive amino acids, more preferably 15 to 50 consecutive amino acids, in particular 20-50 consecutive amino acids, of this wild-type allergen.

The terms "derived from an allergen" and "derived from at least one wild-type allergen", as used herein, mean that the peptide fragments according to the present invention are obtained directly from an allergen by fragmentation or truncation. The amino acid sequence of these peptide fragments is preferably at least 80% identical, more preferably at least 90% identical, most preferably at least 95% identical, in particular 100% identical, to the amino sequence stretch of the wild-type allergen, from which the peptide fragments are derived from. However, the peptides which are not 100% identical to the wild-type allergen fragments should be able to bind with at least 60%, preferably at least 70%, more preferably at least 80%, most preferably at least 90%, strength to an antibody or to antibodies, preferably to IgG antibodies, which are directed to said wild-type allergen fragments. "At least one wild-type allergen" means that the polypeptide of the present invention may comprise B-cell binding peptides of more than one, preferably two, more preferably three, different wild-type allergens (i.e. sources) (e.g. one peptide is derived from Bet v 1, one from Amb a 1 and one from Phl p 1 or two peptides are derived from Bet v 1 and one from Amb a 1).

The degree of identity of a first amino acid sequence to a second amino acid can be determined by a direct comparison between both amino acid sequences using certain algorithms. Such algorithms are, for instance, incorporated in various computer programs (e.g. "BLAST 2 SEQUENCES (blastp)" (Tatusova et al. (1999) FEMS Microbiol. Lett. 174:247-25; Corpet F, Nucl. Acids Res. (1988) 16:10881-10890).

The polypeptides of the present invention may be obtained by recombinant methods or chemical synthesis. Alternatively, it is, of course, also possible to obtain the molecules by enzymatic or chemical cleavage of the wild-type allergen or a polypeptide/protein harbouring the molecule of interest.

It was now surprisingly found that peptide carrier fusion proteins with improved properties can be obtained by employing surface proteins from viruses of the hepadnaviridae class, more specifically the human hepatitis B virus. One up to 20, preferably 3 or 4 up to 20, more preferably 3 or 4 up to 15, even more preferably 3 or 4 up to 10 (i.e. 3, 4, 5, 6, 7, 8, 9, 10), peptide fragments, preferably hypoallergenic peptide fragments, can be fused to the C-terminus and the N-terminus of a surface polypeptide of a virus of the hepadnaviridae family or at least one fragment of said surface polypeptide. A preferred embodiment of the current invention are therefore fusion proteins composed of at least 3 up to 6 hypoallergenic peptide fragments with a carrier protein derived from the surface antigens of human hepatitis B virus. According to a particularly preferred embodiment of the present invention such fusion proteins use the preS protein as carrier. A most preferred embodiment of this invention are fusion proteins where 4 hypoallergenic peptide fragments are fused to the preS carrier protein or a fragment thereof. The (hypoallergenic) peptide fragments can be the same or different and can derived from one or several allergenic proteins and the locus of the peptides within the fusion protein is the C-terminus and the N-terminus of the carrier protein. One up to three (hypoallergenic) peptide fragments can be fused to each of the C-terminus and the N-terminus in such a way that the sum of the (hypoallergenic) peptide fragments will be, for instance, three or four to six. The terms "fused" or "fusion protein", refer to a preferred embodiment of the invention, meaning that the non-allergenic carrier protein and the (hypoallergenic) peptide fragments at the carrier's C- and N-terminus are expressed and prepared as one singular recombinant polypeptide chain A most highly preferred embodiment of the current invention are fusion proteins of the hepatitis B virus preS protein, which carry (hypoallergenic) peptide fragments derived from a specific allergen, such that one or two, preferably two, peptide fragments each are fused to the C-terminus and the N-terminus of the carrier. For illustration, the preferred polypeptides of the current invention may have the general molecular structure represented by the following generic structures:

Structure 1 General construction principle of preferred embodiments

| Peptide A | Peptide B | Pre S | Peptide C | Peptide D |

Structure 2 General construction principle of preferred embodiments

| Peptide A | Peptide B | Pre S | Peptide C |

Structure 3 General construction principle of preferred embodiments

| Peptide B | Pre S | Peptide C | Peptide D |

It is understood that peptides A, B, C and D can be the same or different and may be derived from the same allergen for each individual fusion protein or will be derived from different allergens.

The (hypoallergenic) peptides to be fused to the N- and C-terminus of the surface polypeptide of a virus of the hepadnaviridae family or at least one fragment of said surface polypeptide, preferably the preS protein or a fragment thereof, are preferably selected from the group consisting of major birch pollen allergens, in particular Bet v 1 and Bet v 4, major timothy grass pollen allergens, in particular Phl p 1, Phl p 2, Phl p 5, Phl p 6 and Phl p 7, major house dust mite allergens, in particular Der p 1, Der p 2, Der p 5, Der p 7, Der p 21 and Der p 23, major cat allergen Fel d 1, the major ragweed allergen Amb a 1, the major Japanese cedar allergens Cry j 1 and Cry j 2, major bee allergens, major wasp allergens, profilins, especially Phl p 7, Phl p 12.

Other suited allergens to be used according to the present invention can be derived from the following table 2 without being restricted to said table.

TABLE 2

Sources of hypoallergenic peptides

| Species Name | Allergen Name | Biochem. ID or Obsolete name | MW | cDNA (C) or protein (P) | Reference, Acc. No. |
|---|---|---|---|---|---|
| Ambrosia artemisiifolia short ragweed | Amb a 1 | antigen E | 8 | C | 8, 20 |
| | Amb a 2 | antigen K | 38 | C | 8, 21 |
| | Amb a 3 | Ra3 | 11 | C | 22 |
| | Amb a 5 | Ra5 | 5 | C | 11, 23 |

TABLE 2-continued

Sources of hypoallergenic peptides

| Species Name | Allergen Name | Biochem. ID or Obsolete name | MW | cDNA (C) or protein (P) | Reference, Acc. No. |
|---|---|---|---|---|---|
| | Amb a 6 | Ra6 | 10 | C | 24, 25 |
| | Amb a 7 | Ra7 | 12 | P | 26 |
| *Ambrosia trifida* giant ragweed | Amb t 5 | Ra5G | 4.4 | C | 9, 10, 27 |
| *Artemisia vulgaris* mugwort | Art v 1 | | 27-29 | C | 28 |
| | Art v 2 | | 35 | P | 28A |
| | Art v 3 | lipid transfer protein | 12 | P | 53 |
| | Art v 4 | profilin | 14 | C | 29 |
| *Helianthus annuus* sunflower | Hel a 1 | | 34 | | 29A |
| | Hel a 2 | profilin | 15.7 | C | Y15210 |
| *Mercurialis annua* Caryophyllales | Mer a 1 | profilin | 14-15 | C | Y13271 |
| *Chenopodium album* lamb's-quarters, pigweed, white goosefoot | Che a 1 | | 17 | C | 29B, AY049012 |
| | Che a 2 | profilin | 14 | C | AY082337 |
| | Che a 3 | polcalcin | 10 | C | AY082338 |
| *Salsola kali* Russian-thistle Rosales | Sal k 1 | | 43 | P | 29C |
| *Humulus japonicus* Japanese hop | Hum j 4w | | | C | AY335187 |
| *Parietaria judaica* | Par j 1 | lipid transfer protein 1 | 15 | C | see list of isoallergens |
| | Par j 2 | lipid transfer protein 2 | | C | see list of isoallergens |
| | Par j 3 | profilin | | C | see list of isoallergens |
| *Parietaria officinalis* B. Grasses Poales | Par o 1 | lipid transfer protein | 15 | | 29D |
| *Cynodon dactylon* Bermuda grass | Cyn d 1 | | 32 | C | 30, S83343 |
| | Cyn d 7 | | | C | 31, X91256 |
| | Cyn d 12 | profilin | 14 | C | 31a, Y08390 |
| | Cyn d 15 | | 9 | C | AF517686 |
| | Cyn d 22w | enolase | data pending | | |
| | Cyn d 23 | Cyn d 14 | 9 | C | AF517685 |
| | Cyn d 24 | Pathogenesis- related p. | 21 | P | pending |
| *Dactylis glomerata* orchard grass | Dac g 1 | AgDg1 | 32 | P | 32 |
| | Dac g 2 | | 11 | C | 33, S45354 |
| | Dac g 3 | | | C | 33A, U25343 |
| | Dac g 5 | | 31 | P | 34 |
| *Festuca pratensis* meadow fescue | Fes p 4w | | 60 | | — |
| *Holcus lanatus* velvet grass | Hol l 1 | | | C | Z27084 |
| *Lolium perenne* rye grass | Lol p 1 | group I | 27 | C | 35, 36 |
| | Lol p 2 | group II | 11 | P | 37, 37A, X73363 |
| | Lol p 3 | group III | 11 | P | 38 |
| | Lol p 5 | Lol p IX, Lol p Ib | 31/35 | C | 34, 39 |
| | Lol p 11 | hom: trypsin inhibitor | 16 | C | 39A |
| *Phalaris aquatica* canary grass | Pha a 1 | | | C | 40, S80654 |
| *Phleum pratense* timothy | Phl p 1 | | 27 | C | X78813 |
| | Phl p 2 | | | C | X75925, 41 |
| | Phl p 4 | | | P | 41A |
| | Phl p 5 | Ag25 | 32 | C | 42 |
| | Phl p 6 | | | C | Z27082, 43 |
| | Phl p 11 | trypsin inhibitor hom. | 20 | C | AF521563, 43A |
| | Phl p 12 | profilin | | C | X77583, 44 |
| | Phl p 13 | polygalacturonase | 55-60 | C | AJ238848 |
| *Poa pratensis* Kentucky blue grass | Poa p 1 | group I | 33 | P | 46 |
| | Poa p 5 | | 31/34 | C | 34, 47 |
| *Sorghum halepense* Johnson grass C. Trees Arecales | Sor h 1 | | | C | 48 |
| *Phoenix dactylifera* date palm Fagales | Pho d 2 | profilin | 14.3 | C | Asturias p.c. |
| *Alnus glutinosa* alder | Aln g 1 | | 17 | C | S50892 |
| *Betula verrucosa* birch | Bet v 1 | | 17 | C | see list of isoallergens |
| | Bet v 2 | profilin | 15 | C | M65179 |
| | Bet v 3 | | | C | X79267 |
| | Bet v 4 | | 8 | C | X87153, S54819 |

TABLE 2-continued

Sources of hypoallergenic peptides

| Species Name | Allergen Name | Biochem. ID or Obsolete name | MW | cDNA (C) or protein (P) | Reference, Acc. No. |
|---|---|---|---|---|---|
| | Bet v 6 | h: isoflavone reductase | 33.5 | C | see list of isoallergens |
| | Bet v 7 | cyclophilin | 18 | P | P81531 |
| *Carpinus betulus* hornbeam | Car b 1 | | 17 | C | see list of isoallergens |
| *Castanea sativa* chestnut | Cas s 1 | | 22 | P | 52 |
| | Cas s 5 | chitinase | | | |
| | Cas s 8 | lipid transfer protein | 9.7 | P | 53 |
| *Corylus avellana* hazel | Cor a 1 | | 17 | C | see list of isoallergens |
| | Cor a 2 | profilin | 14 | C | |
| | Cor a 8 | lipid transfer protein | 9 | C | |
| | Cor a 9 | 11S globulin-like protein | 40/? | C | Beyer p.c. |
| | Cor a 10 | luminal binding prot. | 70 | C | AJ295617 |
| | Cor a 11 | 7S vicilin-like prot. | 48 | C | AF441864 |
| *Quercus alba* White oak Lamiales Oleaceae | Que a 1 | | 17 | P | 54 |
| *Fraxinus excelsior* ash | Fra e 1 | | 20 | P | 58A, AF526295 |
| *Ligustrum vulgare* privet | Lig v 1 | | 20 | P | 58A |
| *Olea europea* olive | Ole e 1 | | 16 | C | 59, 60 |
| | Ole e 2 | profilin | 15-18 | C | 60A |
| | Ole e 3 | | 9.2 | | 60B |
| | Ole e 4 | | 32 | P | P80741 |
| | Ole e 5 | superoxide dismutase | 16 | P | P80740 |
| | Ole e 6 | | 10 | C | 60C, U86342 |
| | Ole e 7 | | ? | P | 60D, P81430 |
| | Ole e 8 | Ca2+-binding protein | 21 | C | 60E, AF078679 |
| | Ole e 9 | beta-1,3-glucanase | 46 | C | AF249675 |
| | Ole e 10 | glycosyl hydrolase hom. | 11 | C | 60F, AY082335 |
| *Syringa vulgaris* lilac | Syr v 1 | | 20 | P | 58A |
| Plantaginaceae *Plantago lanceolata* English plantain Pinales | Pla l 1 | | 18 | P | P842242 |
| *Cryptomeria japonica* sugi | Cry j 1 | | 41-45 | C | 55, 56 |
| | Cry j 2 | | | C | 57, D29772 |
| *Cupressus arisonica* cypress | Cup a 1 | | 43 | C | A1243570 |
| *Cupressus sempervirens* common cypress | Cup s 1 | | 43 | C | see list of isoallergens |
| | Cup s 3w | | 34 | C | ref pending |
| *Juniperus ashei* mountain cedar | Jun a 1 | | 43 | P | P81294 |
| | Jun a 2 | | | C | 57A, AJ404653 |
| | Jun a 3 | | 30 | P | 57B, P81295 |
| *Juniperus oxycedrus* prickly juniper | Jun o 4 | hom: calmodulin | 29 | C | 57C, AF031471 |
| *Juniperus sabinoides* mountain cedar | Jun s 1 | | 50 | P | 58 |
| *Juniperus virginiana* eastern red cedar | Jun v 1 | | 43 | P | P81825, 58B |
| Platanaceae *Platanus acerifolia* London plane tree D. Mites | Pla a 1 | | 18 | P | P82817 |
| | Pla a 2 | | 43 | P | P82967 |
| | Pla a 3 | lipid transfer protein | 10 | P | Iris p.c. |
| *Acarus siro* mite | Aca s 13 | arthropod fatty acid binding prot. | 14* | C | AJ006774 |
| *Blomia tropicalis* mite | Blo t 1 | cysteine protease | 39 | C | AF277840 |
| | Blo t 3 | trypsin | 24* | C | Cheong p.c. |
| | Blo t 4 | alpha amylase | 56 | C | Cheong p.c. |
| | Blo t 5 | | | C | U59102 |
| | Blo t 6 | chymotrypsin | 25 | C | Cheong p.c. |
| | Blo t 10 | tropomyosin | 33 | C | 61 |
| | Blo t 11 | paramyosin | 110 | C | AF525465, 61A |
| | Blo t 12 | Bt11a | | C | U27479 |
| | Blo t 13 | Bt6, fatty acid bind prot. | | C | U58106 |
| | Blo t 19 | anti-microbial pep. hom. | 7.2 | C | Cheong p.c. |
| *Dermatophagoides farinae* American house dust mite | Der f 1 | cysteine protease | 25 | C | 69 |
| | Der f 2 | | 14 | C | 70, 70A, see list of isoallergens |
| | Der f 3 | trypsin | 30 | C | 63 |
| | Der f 7 | | 24-31 | C | SW: Q26456, 71 |
| | Der f 10 | tropomyosin | | C | 72 |

TABLE 2-continued

Sources of hypoallergenic peptides

| Species Name | Allergen Name | Biochem. ID or Obsolete name | MW | cDNA (C) or protein (P) | Reference, Acc. No. |
|---|---|---|---|---|---|
| | Der f 11 | paramyosin | 98 | C | 72A |
| | Der f 14 | mag3, apolipophorin | | C | D17686 |
| | Der f 15 | 98k chitinase | 98 | C | AF178772 |
| | Der f 16 | gelsolin/villin | 53 | C | 71A |
| | Der f 17 | Ca binding EF protein | 53 | C | 71A |
| | Der f 18w | 60k chitinase | 60 | C | Weber p.c. |
| *Dermatophagoides microceras* house dust mite | Der m 1 | cysteine protease | 25 | P | 68 |
| *Dermatophagoides pteronyssinus* European house dust mite | Der p 1 | antigen P1, cysteine protease | 25 | C | 62, see list of isoallergens |
| | Der p 2 | | 14 | C | 62A-C, see list of isoallergens |
| | Der p 3 | trypsin | 28/30 | C | 63 |
| | Der p 4 | amylase | 60 | P | 64 |
| | Der p 5 | | 14 | C | 65 |
| | Der p 6 | chymotrypsin | 25 | P | 66 |
| | Der p 7 | | 22/28 | C | 67 |
| | Der p 8 | glutathione transferase | | C | 67A |
| | Der p 9 | collagenolytic serine pro. | | P | 67B |
| | Der p 10 | tropomyosin | 36 | C | Y14906 |
| | Der p 14 | apolipophorin like prot. | | C | Epton p.c. |
| *Euroglyphus maynei* mite | Eur m 2 | | | C | see list of isoallergens |
| | Eur m 14 | apolipophorin | 177 | C | AF149827 |
| *Glycyphagus domesticus* storage mite | Gly d 2 | | | C | 72B, see isoallergen list |
| *Lepidoglyphus destructor* storage mite | Lep d 2 | | 15 | C | 73, 74, 74A, see isoallergen list |
| | Lep d 1 | | | | |
| | Lep d 5 | | | C | 75, AJ250278 |
| | Lep d 7 | | | C | 75, AJ271058 |
| | Lep d 10 | tropomyosin | | C | 75A, AJ250096 |
| | Lep d 13 | | | C | 75, AJ250279 |
| *Tyrophagus putrescentiae* storage mite | Tyr p 2 | | | C | 75B, Y12690 |
| E. Animals | | | | | |
| *Bos domesticus* domestic cattle (see also foods) | Bos d 2 | Ag3, lipocalin | 20 | C | 76, see isoallergen list |
| | Bos d 3 | Ca-binding S100 hom. | 11 | C | L39834 |
| | Bos d 4 | alpha-lactalbumin | 14.2 | C | M18780 |
| | Bos d 5 | beta-lactoglobulin | 18.3 | C | X14712 |
| | Bos d 6 | serum albumin | 67 | C | M73993 |
| | Bos d 7 | immunoglobulin | 160 | | 77 |
| | Bos d 8 | caseins | 20-30 | | 77 |
| *Canis familiaris* (*Canis domesticus*) dog | Can f 1 | | 25 | C | 78, 79 |
| | Can f 2 | | 27 | C | 78, 79 |
| | Can f 3 | albumin | | C | S72946 |
| | Can f 4 | | 18 | P | A59491 |
| *Equus caballus* domestic horse | Equ c 1 | lipocalin | 25 | C | U70823 |
| | Equ c 2 | lipocalin | 18.5 | P | 79A, 79B |
| | Equ c 3 | Ag3 - albumin | 67 | C | 79C, X74045 |
| | Equ c 4 | | 17 | P | 79D |
| | Equ c 5 | AgX | 17 | P | Goubran Botros p.c. |
| *Felis domesticus* cat (saliva) | Fel d 1 | cat-1 | 38 | C | 15 |
| | Fel d 2 | albumin | | C | 79E, X84842 |
| | Fel d 3 | cystatin | 11 | C | 79F, AF238996 |
| | Fel d 4 | lipocalin | 22 | C | AY497902 |
| | Fel d 5w | immunoglobulin A | 400 | | Adedoyin p.c. |
| | Fel d 6w | immunoglobulin M | 800-1000 | | Adedoyin p.c. |
| | Fel d 7w | immunoglobulin G | 150 | | Adedoyin p.c. |
| *Cavia porcellus* guinea pig | Cav p 1 | lipocalin homologue | 20 | P | SW: P83507, 80 |
| | Cav p 2 | | 17 | P | SW: P83508 |
| *Mus musculus* mouse (urine) | Mus m 1 | MUP | 19 | C | 81, 81A |
| *Rattus norvegius* rat (urine) | Rat n 1 | | 17 | C | 82, 83 |
| F. Fungi (moulds) | | | | | |
| 1. Ascomycota | | | | | |
| 1.1 Dothideales | | | | | |
| *Alternaria alternata* | Alt a 1 | | 28 | C | U82633 |
| | Alt a 2 | | 25 | C | 83A, U62442 |
| | Alt a 3 | heat shock prot. | 70 | C | U87807, U87808 |
| | Alt a 4 | prot. disulfideisomerase | 57 | C | X84217 |
| | Alt a 6 a | cid ribosomal prot. P2 | 11 | C | X78222, U87806 |
| | Alt a 7 | YCP4 protein | 22 | C | X78225 |
| | Alt a 10 | aldehyde dehydrogenase | 53 | C | X78227, P42041 |
| | Alt a 11 | enolase | 45 | C | U82437 |
| | Alt a 12 | acid ribosomal prot. P1 | 11 | C | X84216 |

TABLE 2-continued

Sources of hypoallergenic peptides

| Species Name | Allergen Name | Biochem. ID or Obsolete name | MW | cDNA (C) or protein (P) | Reference, Acc. No. |
|---|---|---|---|---|---|
| *Cladosporium herbarum* | Cla h 1 | | 13 | | 83B, 83C |
| | Cla h 2 | | 23 | | 83B, 83C |
| | Cla h 3 | aldehyde dehydrogenase | 53 | C | X78228 |
| | Cla h 4 | acid ribosomal prot. P2 | 11 | C | X78223 |
| | Cla h 5 | YCP4 protein | 22 | C | X78224 |
| | Cla h 6 | enolase | 46 | C | X78226 |
| | Cla h 12 | acid ribosomal prot. P1 | 11 | C | X85180 |
| 1.2 Eurotiales | | | | | |
| *Aspergillus flavus* | Asp fl 13 | alkaline serine protease | 34 | | 84 |
| *Aspergillus fumigatus* | Asp f 1 | | 18 | C | M83781, S39330 |
| | Asp f 2 | | 37 | C | U56938 |
| | Asp f 3 | peroxisomal protein | 19 | C | U20722 |
| | Asp f 4 | | 30 | C | AJ001732 |
| | Asp f 5 | metalloprotease | 40 | C | Z30424 |
| | Asp f 6 | Mn superoxide dismut. | 26.5 | C | U53561 |
| | Asp f 7 | | 12 | C | AJ223315 |
| | Asp f 8 | ribosomal prot. P2 | 11 | C | AJ224333 |
| | Asp f 9 | | 34 | C | AJ223327 |
| | Asp f 10 | aspartic protease | 34 | C | X85092 |
| | Asp f 11 | peptidyl-prolyl isomerase | 24 | | 84A |
| | Asp f 12 | heat shock prot. P90 90 | | C | 85 |
| | Asp f 13 | alkaline serine protease | 34 | | 84B |
| | Asp f 15 | | 16 | C | AJ002026 |
| | Asp f 16 | | 43 | C | g3643813 |
| | Asp f 17 | | | C | AJ224865 |
| | Asp f 18 | vacuolar serine protease | 34 | | 84C |
| | Asp f 22w | enolase | 46 | C | AF284645 |
| | Asp f 23 | L3 ribosomal protein | 44 | C | 85A, AF464911 |
| *Aspergillus niger* | Asp n 14 | beta-xylosidase | 105 | C | AF108944 |
| | Asp n 18 | vacuolar serine protease | 34 | C | 84B |
| | Asp n 25 | 3-phytase B | 66-100 | C | 85B, P34754 |
| | Asp n ? | | 85 | C | Z84377 |
| *Aspergillus oryzae* | Asp o 13 | alkaline serine protease | 34 | C | X17561 |
| | Asp o 21 | TAKA-amylase A | 53 | C | D00434, M33218 |
| *Penicillium brevicompactum* | Pen b 13 | alkaline serine protease | 33 | | 86A |
| *Penicillium chrysogenum* (formerly *P. notatum*) | Pen ch 13 | alkaline serine protease | 34 | | 87 |
| | Pen ch 18 | vacuolar serine protease | 32 | | 87 |
| | Pen ch 20 | N-acetyl glucosaminidase | 68 | | 87A |
| *Penicillium citrinum* | Pen c 3 | peroxisomal mem. prot. | 18 | | 86B |
| | Pen c 13 | alkaline serine protease | 33 | | 86A |
| | Pen c 19 | heat shock prot. P70 | 70 | C | U64207 |
| | Pen c 22w | enolase | 46 | C | AF254643 |
| | Pen c 24 | elongation factor 1 beta | | C | AY363911 |
| *Penicillium oxalicum* | Pen o 18 | vacuolar serine protease | 34 | | 87B |
| 1.3 Hypocreales | | | | | |
| *Fusarium culmorum* | Fus c 1 | ribosomal prot. P2 | 11* | C | AY077706 |
| | Fus c 2 | thioredoxin-like prot. | 13* | C | AY077707 |
| 1.4 Onygenales | | | | | |
| *Trichophyton rubrum* | Tri r 2 | | | C | 88 |
| *Trichophyton tonsurans* | Tri r 4 | serine protease | | C | 88 |
| | Tri t 1 | | 30 | P | 88A |
| | Tri t 4 | serine protease | 83 | C | 88 |
| 1.5 Saccharomycetales | | | | | |
| *Candida albicans* | Cand a 1 | | 40 | C | 89 |
| | Cand a 3 | peroxisomal protein | 29 | C | AY136739 |
| *Candida boidinii* | Cand b 2 | | 20 | C | J04984, J04985 |
| 2. Basidiomycotina | | | | | |
| 2.1 Hymenomycetes | | | | | |
| *Psilocybe cubensis* | Psi c 1 | | | | |
| | Psi c 2 | cyclophilin | 16 | | 89A |
| *Coprinus comatus* shaggy cap | Cop c 1 | leucine zipper protein | 11 | C | AJ132235 |
| | Cop c 2 | | | | AJ242791 |
| | Cop c 3 | | | | AJ242792 |
| | Cop c 5 | | | | AJ242793 |
| | Cop c 7 | | | | AJ242794 |
| 2.2 Urediniomycetes | | | | | |
| *Rhodotorula mucilaginosa* | Rho m 1 | enolase | 47 | C | 89B |
| | Rho m 2 | vacuolar serine protease | 31 | C | AY547285 |

TABLE 2-continued

Sources of hypoallergenic peptides

| Species Name | Allergen Name | Biochem. ID or Obsolete name | MW | cDNA (C) or protein (P) | Reference, Acc. No. |
|---|---|---|---|---|---|
| 2.3 Ustilaginomycetes | | | | | |
| *Malassezia furfur* | Mala f 2 | MF1, peroxisomal membrane protein | 21 | C | AB011804, 90 |
| | Mala f 3 | MF2, peroxisomal membrane protein | 20 | C | AB011805, 90 |
| | Mala f 4 | mitochondrial malate dehydrogenase | 35 | C | AF084828, 90A |
| *Malassezia sympodialis* | Mala s 1 | | | C | X96486, 91 |
| | Mala s 5 | | 18* | C | AJ011955 |
| | Mala s 6 | | 17* | C | AJ011956 |
| | Mala s 7 | | | C | AJ011957, 91A |
| | Mala s 8 | | 19* | C | AJ011958, 91A |
| | Mala s 9 | | 37* | C | AJ011959, 91A |
| | Mala s 10 | heat shock prot. 70 | 86 | C | AJ428052 |
| | Mala s 11 | Mn superoxide dismut. | 23 | C | AJ548421 |
| 3. Deuteromycotina | | | | | |
| 3.1 Tuberculariales | | | | | |
| *Epicoccum purpurascens* (formerly *E. nigrum*) | Epi p 1 | serine protease | 30 | P | SW: P83340, 91B |
| G. Insects | | | | | |
| *Aedes aegyptii* | Aed a 1 | apyrase | 68 | C | L12389 |
| mosquito | Aed a 2 | | 37 | C | M33157 |
| *Apis mellifera* | Api m 1 | phospholipase A2 | 16 | C | 92 |
| honey bee | Api m 2 | hyaluronidase | 44 | C | 93 |
| | Api m 4 | melittin | 3 | C | 94 |
| | Api m 6 | | 7-8 | P | Kettner p.c. |
| | Api m 7 | CUB serine protease | 39 | C | AY127579 |
| *Bombus pennsylvanicus* | Bom p 1 | phospholipase | 16 | P | 95 |
| bumble bee | Bom p 4 | protease | | P | 95 |
| *Blattella germanica* | Bla g 1 | Bd90k | | C | |
| German cockroach | Bla g 2 | aspartic protease | 36 | C | 96 |
| | Bla g 4 | calycin | 21 | C | 97 |
| | Bla g 5 | glutathione transferase | 22 | C | 98 |
| | Bla g 6 | troponin C | 27 | C | 98 |
| *Periplaneta americana* | Per a 1 | Cr-PII | | C | |
| American cockroach | Per a 3 | Cr-PI | 72-78 | C | 98A |
| | Per a 7 | tropomyosin | 37 | C | Y14854 |
| *Chironomus kiiensis* midge | Chi k 10 | tropomyosin | 32.5* | C | AJ012184 |
| *Chironomus thummi thummi* | Chi t 1-9 | hemoglobin | 16 | C | 99 |
| midge | Chi t 1.01 | component III | 16 | C | P02229 |
| | Chi t 1.02 | component IV | 16 | C | P02230 |
| | Chi t 2.0101 | component I | 16 | C | P02221 |
| | Chi t 2.0102 | component IA | 16 | C | P02221 |
| | Chi t 3 | component II-beta | 16 | C | P02222 |
| | Chi t 4 | component IIIA | 16 | C | P02231 |
| | Chi t 5 | component VI | 16 | C | P02224 |
| | Chi t 6.01 | component VIIA | 16 | C | P02226 |
| | Chi t 6.02 | component IX | 16 | C | P02223 |
| | Chi t 7 | component VIIB | 16 | C | P02225 |
| | Chi t 8 | component VIII | 16 | C | P02227 |
| | Chi t 9 | component X | 16 | C | P02228 |
| *Ctenocephalides felis felis* | Cte f 1 | | | | |
| cat flea | Cte f 2 | M1b | 27 | C | AF231352 |
| | Cte f 3 | | 25 | C | |
| *Thaumetopoea pityocampa* pine processionary moth | Tha p 1 | | 15 | P | PIR: A59396, 99A |
| *Lepisma saccharina* silverfish | Lep s 1 | tropomyosin | 36 | C | AJ309202 |
| *Dolichovespula maculata* | Dol m 1 | phospholipase A1 | 35 | C | 100 |
| white face hornet | Dol m 2 | hyaluronidase | 44 | C | 101 |
| | Dol m 5 | antigen 5 | 23 | C | 102, 103 |
| *Dolichovespula arenaria* yellow hornet | Dol a 5 | antigen 5 | 23 | C | 104 |
| *Polistes annularies* | Pol a 1 | phospholipase A1 | 35 | P | 105 |
| wasp | Pol a 2 | hyaluronidase | 44 | P | 105 |
| | Pol a 5 | antigen 5 | 23 | C | 104 |
| *Polistes dominulus* | Pol d 1 | | | | Hoffman p.c. |
| Mediterranean paper wasp | Pol d 4 | serine protease | 32-34 | C | Hoffman p.c. |
| | Pol d 5 | | | | P81656 |
| *Polistes exclamans* | Pol e 1 | phospholipase A1 | 34 | P | 107 |
| wasp | Pol e 5 | antigen 5 | 23 | C | 104 |

TABLE 2-continued

Sources of hypoallergenic peptides

| Species Name | Allergen Name | Biochem. ID or Obsolete name | MW | cDNA (C) or protein (P) | Reference, Acc. No. |
|---|---|---|---|---|---|
| *Polistes fuscatus* wasp | Pol f 5 | antigen 5 | 23 | C | 106 |
| *Polistes gallicus* wasp | Pol g 5 | antigen 5 | 24 | C | P83377 |
| *Polistes metricus* wasp | Pol m 5 | antigen 5 | 23 | C | 106 |
| *Vespa crabo* European hornet | Vesp c 1 | phospholipase | 34 | P | 107 |
| | Vesp c 5 | antigen 5 | 23 | C | 106 |
| *Vespa mandarina* giant asian hornet | Vesp m 1 | | | | Hoffman p.c. |
| | Vesp m 5 | | | | P81657 |
| *Vespula flavopilosa* yellowjacket | Ves f 5 | antigen 5 | 23 | C | 106 |
| *Vespula germanica* yellowjacket | Ves g 5 | antigen 5 | 23 | C | 106 |
| *Vespula maculifrons* yellowjacket | Ves m 1 | phospholipase A1 | 33.5 | C | 108 |
| | Ves m 2 | hyaluronidase | 44 | P | 109 |
| | Ves m 5 | antigen 5 | 23 | C | 104 |
| *Vespula pennsylvanica* yellowjacket | Ves p 5 | antigen 5 | 23 | C | 106 |
| *Vespula squamosa* yellowjacket | Ves s 5 | antigen 5 | 23 | C | 106 |
| *Vespula vidua* wasp | Ves vi 5 | antigen 5 | 23 | C | 106 |
| *Vespula vulgaris* yellowjacket | Ves v 1 | phospholipase A1 | 35 | C | 105A |
| | Ves v 2 | hyaluronidase | 44 | P | 105A |
| | Ves v 5 | antigen 5 | 23 | C | 104 |
| *Myrmecia pilosula* Australian jumper ant | Myr p 1 | | | C | X70256 |
| | Myr p 2 | | | C | S81785 |
| *Solenopsis geminata* tropical fire ant | Sol g 2 | | | | Hoffman p.c. |
| | Sol g 4 | | | | Hoffman p.c. |
| *Solenopsis invicta* fire ant | Sol i 2 | | 13 | C | 110, 111 |
| | Sol i 3 | | 24 | C | 110 |
| | Sol i 4 | | 13 | C | 110 |
| *Solenopsis saevissima* Brazilian fire ant | Sol s 2 | | | | Hoffman p.c. |
| *Triatoma protracta* California kissing bug | Tria p 1 | Procalin | 20 | C | AF179004, 111A. |
| H. Foods | | | | | |
| *Gadus callarias* cod | Gad c 1 | allergen M | 12 | C | 112, 113 |
| *Salmo salar* Atlantic salmon | Sal s 1 | parvalbumin | 12 | C | X97824 |
| *Bos domesticus* domestic cattle (milk) see also animals | Bos d 4 | alpha-lactalbumin | 14.2 | C | M18780 |
| | Bos d 5 | beta-lactoglobulin | 18.3 | C | X14712 |
| | Bos d 6 | serum albumin | 67 | C | M73993 |
| | Bos d 7 | immunoglobulin | 160 | | 77 |
| | Bos d 8 | caseins | 20-30 | | 77 |
| *Cyprinus carpio* (Common carp) | Cyp c 1 | parvalbumin | 12 | C | 129 |
| *Gallus domesticus* chicken | Gal d 1 | ovomucoid | 28 | C | 114, 115 |
| | Gal d 2 | ovalbumin | 44 | C | 114, 115 |
| | Gal d 3 | Ag22, conalbumin | 78 | C | 114, 115 |
| | Gal d 4 | lysozyme | 14 | C | 114, 115 |
| | Gal d 5 | serum albumin | 69 | C | X60688 |
| *Metapenaeus ensis* shrimp | Met e 1 | tropomyosin | | C | U08008 |
| *Penaeus aztecus* shrimp | Pen a 1 | tropomyosin | 36 | P | 116 |
| *Penaeus indicus* shrimp | Pen i 1 | tropomyosin | 34 | C | 116A |
| *Penaeus monodon* black tiger shrimp | Pen m 1 | tropomyosin | 38 | C | |
| | Pen m 2 | arginine kinase | 40 | C | AF479772, 117 |
| *Todarodes pacificus* squid | Tod p 1 | tropomyosin | 38 | P | 117A |
| *Helix aspersa* brown garden snail | Hel as 1 | tropomyosin | 36 | C | Y14855, 117B |
| *Haliotis midae* abalone | Hal m 1 | | 49 | | 117C |
| *Rana esculenta* edible frog | Ran e 1 | parvalbumin alpha | 11.9* | C | AJ315959 |
| | Ran e 2 | parvalbumin beta | 11.7* | C | AJ414730 |
| *Brassica juncea* oriental mustard | Bra j 1 | 2S albumin | 14 | C | 118 |
| *Brassica napus* rapeseed | Bra n 1 | 2S albumin | 15 | P | 118A, P80208 |

TABLE 2-continued

Sources of hypoallergenic peptides

| Species Name | Allergen Name | Biochem. ID or Obsolete name | MW | cDNA (C) or protein (P) | Reference, Acc. No. |
|---|---|---|---|---|---|
| *Brassica rapa* turnip | Bra r 2 | hom: prohevein | 25 | | P81729 |
| *Hordeum vulgare* barley | Hor v 15 | BMAI-1 | 15 | C | 119 |
| | Hor v 16 | alpha-amylase | | | |
| | Hor v 17 | beta-amylase | | | |
| | Hor v 21 | gamma-3 hordein | 34 | C | 119A, SW: P80198 |
| *Secale cereale* rye | Sec c 20 | secalin | | | see isoall. list |
| *Triticum aestivum* wheat | Tri a 18 | agglutinin | | | |
| | Tri a 19 | omega-5 gliadin | 65 | P | PIR: A59156 |
| *Zea mays* maise, corn | Zea m 14 | lipid transfer prot. | 9 | P | P19656 |
| *Oryza sativa* rice | Ory s 1 | | | C | 119B, U31771 |
| *Apium graveolens* celery | Api g 1 | hom: Bet v 1 | 16* | C | Z48967 |
| | Api g 4 | profilin | | | AF129423 |
| | Api g 5 | | 55/58 | P | P81943 |
| *Daucus carota* carrot | Dau c 1 | hom: Bet v 1 | 16 | C | 117D, see isoallergen list |
| | Dau c 4 | profilin | | C | AF456482 |
| *Corylus avellana* hazelnut | Cor a 1.04 | hom: Bet v 1 | 17 | C | see list of isoallergens |
| | Cor a 2 | profilin | 14 | C | AF327622 |
| | Cor a 8 | lipid transfer protein | 9 | C | AF329829 |
| *Malus domestica* apple | Mal d 1 | hom: Bet v 1 | | C | see list of isoallergens |
| | Mal d 2 | hom: thaumatin | | C | AJ243427 |
| | Mal d 3 | lipid transfer protein | 9 | C | Pastorello p.c. |
| | Mal d 4 | profilin | 14.4* | C | see list of isoallergens |
| *Pyrus communis* pear | Pyr c 1 | hom: Bet v 1 | 18 | C | AF05730 |
| | Pyr c 4 | profilin | 14 | C | AF129424 |
| | Pyr c 5 | hom: isoflavone reductas | 33.5 | C | AF071477 |
| *Persea americana* avocado | Pers a 1 | endochitinase | 32 | C | Z78202 |
| *Prunus armeniaca* apricot | Pru ar 1 | hom: Bet v 1 | | C | U93165 |
| | Pru ar 3 | lipid transfer protein | 9 | P | |
| *Prunus avium* sweet cherry | Pru av 1 | hom: Bet v 1 | | C | U66076 |
| | Pru av 2 | hom: thaumatin | | C | U32440 |
| | Pru av 3 | lipid transfer protein | 10 | C | AF221501 |
| | Pru av 4 | profilin | 15 | C | AF129425 |
| *Prunus domestica* European plum | Pru d 3 | lipid transfer protein | 9 | P | 119C |
| *Prunus persica* peach | Pru p 3 | lipid transfer protein | 10 | P | P81402 |
| | Pru p 4 | profilin | 14 | C | see isoallergen list |
| *Asparagus officinalis* Asparagus | Aspa o 1 | lipid transfer protein | 9 | P | 119D |
| *Crocus sativus* saffron crocus | Cro s 1 | | 21 | | Varasteh A-R p.c. |
| *Lactuca sativa* lettuce | Lac s 1 | lipid transfer protein | 9 | | Vieths p.c. |
| *Vitis vinifera* grape | Vit v 1 | lipid transfer protein | 9 | P | P80274 |
| *Musa × paradisiaca* banana | Mus xp 1 | profilin | 15 | C | AF377948 |
| *Ananas comosus* pineapple | Ana c 1 | profilin | 15 | C | AF377949 |
| | Ana c 2 | bromelain | 22.8* | C | 119E-G, D14059 |
| *Citrus limon* lemon | Cit l 3 | lipid transfer protein | 9 | P | Torrejon p.c. |
| *Citrus sinensis* sweet orange | Cit s 1 | germin-like protein | 23 | P | Torrejon p.c. |
| | Cit s 2 | profilin | 14 | P | Torrejon p.c. |
| | Cit s 3 | lipid transfer protein | 9 | P | Torrejon p.c. |
| *Litchi chinensis* litchi | Lit c 1 | profilin | 15 | C | AY049013 |
| *Sinapis alba* yellow mustard | Sin a 1 | 2S albumin | 14 | C | 120 |
| *Glycine max* soybean | Gly m 1 | HPS | 7 | P | 120A |
| | Gly m 2 | | 8 | P | A57106 |
| | Gly m 3 | profilin | 14 | C | see list of isoallergens |
| | Gly m 4 | (SAM22) PR-10 prot. | 17 | C | X60043, 120B |
| *Vigna radiata* mung bean | Vig r 1 | PR-10 protein | 15 | C | AY792956 |
| *Arachis hypogaea* peanut | Ara h 1 | vicilin | 63.5 | C | L34402 |
| | Ara h 2 | conglutin | 17 | C | L77197 |
| | Ara h 3 | glycinin | 60 | C | AF093541 |
| | Ara h 4 | glycinin | 37 | C | AF086821 |
| | Ara h 5 | profilin | 15 | C | AF059616 |
| | Ara h 6 | hom: conglutin | 15 | C | AF092846 |

TABLE 2-continued

Sources of hypoallergenic peptides

| Species Name | Allergen Name | Biochem. ID or Obsolete name | MW | cDNA (C) or protein (P) | Reference, Acc. No. |
|---|---|---|---|---|---|
| | Ara h 7 | hom: conglutin | 15 | C | AF091737 |
| | Ara h 8 | PR-10 protein | 17 | C | AY328088 |
| *Lens culinaris* | Len c 1 | vicilin | 47 | C | see list of isoallergens |
| lentil | Len c 2 | seed biotinylated prot. | 66 | P | 120C |
| *Pisum savitum* | Pis s 1 | vicilin | 44 | C | see list of isoallergens |
| pea | Pis s 2 | convicilin | 63 | C | pending |
| *Actinidia chinensis* | Act c 1 | cysteine protease | 30 | P | P00785 |
| kiwi | Act c 2 | thaumatin-like protein | 24 | P | SW: P81370, 121 |
| *Capsicum annuum* | Cap a 1w | osmotin-like protein | 23 | C | AJ297410 |
| bell pepper | Cap a 2 | profilin | 14 | C | AJ417552 |
| *Lycopersicon esculentum* | Lyc e 1 | profilin | 14 | C | AJ417553 |
| tomato | Lyc e 2 | b-fructofuranosidase | 50 | C | see isoallergen list |
| | Lyc e 3 | lipid transfer prot. | 6 | C | U81996 |
| *Solanum tuberosum* | Sola t 1 | patatin | 43 | P | P15476 |
| potato | Sola t 2 | cathepsin D inhibitor | 21 | P | P16348 |
| | Sola t 3 | cysteine protease inhibitor | 21 | P | P20347 |
| | Sola t 4 | aspartic protease inhibitor | 16 + 4 | P | P30941 |
| *Bertholletia excelsa* | Ber e 1 | 2S albumin | 9 | C | P04403, M17146 |
| Brazil nut | Ber e 2 | 11S globulin seed storage protein | 29 | C | AY221641 |
| *Juglans nigra* | Jug n 1 | 2S albumin | 19* | C | AY102930 |
| black walnut | Jug n 2 | vicilin-like prot. | 56* | C | AY102931 |
| *Juglans regia* | Jug r 1 | 2S albumin | | C | U66866 |
| English walnut | Jug r 2 | vicilin | 44 | C | AF066055 |
| | Jug r 3 | lipid transfer protein | 9 | P | Pastorello |
| *Anacardium occidentale* | Ana o 1 | vicilin-like protein | 50 | C | see isoallergen list |
| Cashew | Ana o 2 | legumin-like protein | 55 | C | AF453947 |
| | Ana o 3 | 2S albumin | 14 | C | AY081853 |
| *Ricinus communis* | Ric c 1 | 2S albumin | | C | P01089 |
| Castor bean | | | | | |
| *Sesamum indicum* | Ses i 1 | 2S albumin | 9 | C | 121A, AF240005 |
| sesame | Ses i 2 | 2S albumin | 7 | C | AF091841 |
| | Ses i 3 | 7S vicilin-like globulin | 45 | C | AF240006 |
| | Ses i 4 | oleosin | 17 | C | AAG23840 |
| | Ses i 5 | oleosin | 15 | C | AAD42942 |
| *Cucumis melo* | Cuc m 1 | serine protease | 66 | C | D32206 |
| muskmelon | Cuc m 2 | profilin | 14 | C | AY271295 |
| | Cuc m 3 | pathogenesis-rel p. PR-1 | 16* | P | P83834 |
| I. Others | | | | | |
| *Anisakis simplex* | Ani s 1 | | 24 | P | 121B, A59069 |
| nematode | Ani s 2 | paramyosin | 97 | C | AF173004 |
| | Ani s 3 | tropomyosin | 41 | C | 121C, Y19221 |
| | Ani s 4 | | 9 | P | P83885 |
| *Argas reflexus* | Arg r 1 | | 17 | C | AJ697694 |
| piigeon tick | | | | | |
| *Ascaris suum* | Asc s 1 | | 10 | P | 122 |
| worm | | | | | |
| *Carica papaya* | Car p 3w | papain | 23.4* | C | 122A, M15203 |
| papaya | | | | | |
| *Dendronephthya nipponica* | Den n 1 | | 53 | P | 122B |
| soft coral | | | | | |
| *Hevea brasiliensis* | Hev b 1 | elongation factor | 58 | P | 123, 124 |
| rubber (latex) | Hev b 2 | 1,3-glucanase | 34/36 | C | 125 |
| | Hev b 3 | | 24 | P | 126, 127 |
| | Hev b 4 | component of microhelix complex | 100-115 | P | 128 |
| | Hev b 5 | | 16 | C | U42640 |
| | Hev b 6.01 | hevein precursor | 20 | C | M36986, p02877 |
| | Hev b 6.02 | hevein | 5 | C | M36986, p02877 |
| | Hev b 6.03 | C-terminal fragment | 14 | C | M36986, p02877 |
| | Hev b 7.01 | hom: patatin from B-serum | 42 | C | U80598 |
| | Hev b 7.02 | hom: patatin from C-serum | 44 | C | AJ223038 |
| | Hev b 8 | profilin | 14 | C | see list of isoallergens |
| | Hev b 9 | enolase | 51 | C | AJ132580 |
| | Hev b 10 | Mn superoxide dismut. | 26 | C | see list of isoallergens |
| | Hev b 11 | class 1 chitinase | | C | see list of isoallergens |
| | Hev b 12 | lipid transfer protein | 9.3 | C | AY057860 |
| | Hev b 13 | esterase | 42 | P | P83269 |
| *Homo sapiens* | Hom s 1 | | 73* | C | Y14314 |
| human autoallergens | Hom s 2 | | 10.3* | C | X80909 |
| | Hom s 3 | | 20.1* | C | X89985 |
| | Hom s 4 | | 36* | C | Y17711 |
| | Hom s 5 | | 42.6* | C | P02538 |
| *Triplochiton scleroxylon* | Trip s 1 | class 1 chitinase | 38.5 | P | Kespohl p.c. |
| obeche | | | | | |

REFERENCES

1 Marsh, D. G., and L. R. Freidhoff. 1992. ALBE, an allergen database. IUIS, Baltimore, Md., Edition 1.0.
2 Marsh, D. G. et al. 1986. Allergen nomenclature. Bull WHO 64:767-770.
3 King, T. P. et al. 1964. Biochemistry 3:458-468.
4 Lowenstein, H. 1980. Allergy 35:188-191.
5 Aukrust, L. 1980. Allergy 35:206-207.
6 Demerec, M. et al. 1966. Genetics 54:61-75.
7 Bodmer, J. G. et al. 1991. Immunogenetics 33:301-309.
8 Griffith, I. J. et al. 1991. Int. Arch. Allergy Appl. Immunol. 96:296-304.
9 Roebber, M. et al. 1985. J. Immunol. 134:3062-3069.
10 Metzler, W. J. et al. 1992. Biochemistry 31:5117-5127.
11 Metzler, W. J. et al. 1992. Biochemistry 31:8697-8705.
12 Goodfriend, L. et al. 1979. Fed. Proc. 38:1415.
13 Ekramoddoullah, A. K. M. et al. 1982. Mol. Immunol. 19:1527-1534.
14 Ansari, A. A. et al. 1987. J. Allergy Clin. Immunol. 80:229-235.
15 Morgenstern, J. P. et al. 1991. Proc. Natl. Acad. Sci. USA 88:9690-9694.
16 Griffith, I. J. et al. 1992. Gene 113:263-268.
17 Weber, A. et al. 1986. Biochem. Physiol. 83B:321-324.
18 Weber, A. et al. 1987. Allergy 42:464-470.
19 Stanworth, D. R. et al. 1990. Bulletin WHO 68:109-111.
20 Ralhar, T. et al. 1991. J. Biol. Chem. 266: 1229-1236.
21 Rogers, B. L. et al. 1991. J. Immunol. 147:2547-2552.
22 Klapper, D. G. et al. 1980. Biochemistry 19:5729-5734.
23 Ghosh, B. et al. 1993. J. Immunol. 150:5391-5399.
24 Roebber, M. et al. 1983. J. Immunol. 131:706-711.
25 Lubahn, B., and D. G. Klapper. 1993. J. Allergy Clin. Immunol. 91:338.
26 Roebber, M., and D. G. Marsh. 1991. J. Allergy Clin. Immunol. 87:324.
27 Goodfriend L. et al. Mol Immunol 22: 899-906, 1985.
28 Himly M. et al. FASEB J 17: 106-108, 2003.
28A Nilsen, B. M. et al. 1991. J. Biol. Chem. 266:2660-2668.
29 Wopfner N. et al. Biol Chem 383: 1779-1789, 2002.
29A Jimenez A. et al. 1994. Int Arch Allergy Immunol 105: 297-307.
29B Barderas R. et al. Int Arch Allergy Immunol 127: 47-54, 2002.
29C Carnes J. et al. Allergy 56, Supplement 68: 274, 2001.
29D Giuliani A. et al. Allergy 42: 434-440, 1987.
30 Smith, P. M. et al. 1996. J. Allergy Clin. Immunol. 98:331-343.
31 Suphioglu, C. et al. 1997. FEBS Lett. 402:167-172.
31a Asturias J. A. et al. 1997. Clin Exp Allergy 27:1307-1313.
32 Mecheri, S. et al. 1985. Allergy Appl. Immunol. 78:283-289.
33 Roberts, A. M. et al. 1993. Allergy 48:615-623.
33a Guerin-Marchand, C. et al. 1996. Mol. Immunol. 33:797-806.
34 Klysner, S. et al. 1992. Clin. Exp. Allergy 22: 491-497.
35 Perez, M. et al. 1990. J. Biol. Chem. 265:16210-16215.
36 Griffith, I. J. et al. 1991. FEBS Letters 279:210-215.
37 Ansari, A. A. et al. 1989. J. Biol. Chem. 264:11181-11185.
37a Sidoli, A. et al. 1993. J. Biol. Chem. 268:21819-21825.
38 Ansari, A. A. et al. 1989. Biochemistry 28:8665-8670.
39 Singh, M. B. et al. 1991. Proc. Natl. Acad. Sci. 88:1384-1388.
39a van Ree R. et al. 1995. J Allergy Clin Immunol 95:970-978.
40 Suphioglu, C. and Singh, M. B. 1995. Clin. Exp. Allergy 25:853-865.
41 Dolecek, C. et al. 1993. FEBS Lett. 335:299-304.
41A Fischer S. et al. 1996. J Allergy Clin Immunol 98:189-198.
42 Matthiesen, F., and H. Lowenstein. 1991. Clin. Exp. Allergy 21:297-307.
43 Petersen, A. et al. 1995. Int. Arch. Allergy Immunol. 108: 55-59.
43A Marknell DeWitt A. et al. Clin Exp Allergy 32: 1329-1340, 2002.
44 Valenta, R. et al. 1994. Biochem. Biophys. Res. Commun. 199:106-118.
46 Esch, R. E., and D. G. Klapper. 1989. Mol. Immunol. 26:557-561.
47 Olsen, E. et al. 1991. J. Immunol. 147:205-211.
48 Avjioglu, A. et al. 1993. J. Allergy Clin. Immunol. 91:340.
52 Kos T. et al. 1993. Biochem Biophys Res Commun 196: 1086-92.
53 Diaz-Perales A. et al. 2000. Clin Exp Allergy 30:1403-1410.
54 Ipsen, H., and O. C. Hansen. 1991. Mol. Immunol. 28: 1279-1288.
55 Taniai, M. et al. 1988. FEBS Lett. 239:329-332.
56 Griffith, I. J. et al. 1993. J. Allergy Clin. Immunol. 91:339.
57 Sakaguchi, M. et al. Allergy 45: 309-312, 1990.
57A Yokoyama M. et al. Biochem Biophys Res Commun 275: 195-202, 2000.
57B Midoro-Horiuti T. et al. J Immunol 164: 2188-2192, 2000.
57C Tinghino R. et al. J. Allergy Clin. Immunol. 101: 772-777, 1998.
58 Gross G N et al. Scand J Immunol 8: 437-441, 1978.
58A Obispo T M et al. Clin Exp Allergy 23: 311-316, 1993.
58B Midoro-Horiuti T. et al. Clin Exp Allergy 31: 771-778, 2001.
59 Lombardero M. et al. Clin. Exp. Allergy 24: 765-770, 1994.
60 Villalba, M. et al. Eur. J. Biochem. 216: 863-869, 1993.
60A Asturias J A et al. J Allergy Clin Immunol 100: 365-372, 1997.
60B Batanero E. et al. Eur J Biochem 241: 772-778, 1996.
60C Batanero E. et al. FEBS Lett. 410: 293-296, 1997.
60D Tejera M L et al. J Allergy Clin Immunol 104: 797-802, 1999.
60E Ledesma A. et al. FEBS Lett 466: 192-196, 2000.
60F Barral P. et al. J Immunol 172: 3644-3651, 2004.
61 Yi F C et al. Clin Exp Allergy 32: 1203-1210, 2002.
61A Ramos J D et al. Int Arch Allergy Immunol 126: 286-293, 2001.
62 Chua, K. Y. et al. J. Exp. Med. 167: 175-182, 1988.
62A Chua, K. Y. et al. Int. Arch. Allergy Appl. Immunol. 91: 118-123, 1990.
62B Smith A M et al. Int Arch Allergy Immunol 124: 61-63, 2001.
62C Smith A M et al. J Allergy Clin Immunol 107: 977-984, 2001.
63 Smith W A, Thomas W R. Int Arch Allergy Immunol 109: 133-140, 1996.
64 Lake, F. R. et al. J. Allergy Clin. Immunol. 87: 1035-1042, 1991.
65 Tovey, E. R. et al. J. Exp. Med. 170: 1457-1462, 1989.
66 Yasueda, H., T. Shida, T. Ando, S. Sugiyama, and H. Yamakawa. 1991. Allergenic and proteolytic properties of fourth allergens from Dermatophagoides mites. In: "Dust Mite Allergens and Asthma. Report of the 2nd international workshop" A. Todt, Ed., UCB Institute of Allergy, Brussels, Belgium, pp. 63-64.
67 Shen, H.-D. et al. Clin. Exp. Allergy 23: 934-940, 1993.

67A O'Neil G M et al. Biochim Biophys Acta, 1219: 521-528, 1994.
67B King C. et al. J Allergy Clin Immunol 98: 739-747, 1996.
68 Lind P. et al. J. Immunol. 140: 4256-4262, 1988.
69 Dilworth, R. J. et al. Clin. Exp. Allergy 21: 25-32, 1991.
70 Nishiyama, C. et al. Int. Arch. Allergy Immunol. 101: 159-166, 1993.
70A Trudinger, M. et al. Clin. Exp. Allergy 21: 33-38, 1991.
71 Shen H D et al. Clin Exp Allergy 25: 1000-1006, 1995.
71A Tategaki A. et al. ACI International suppl. 1: 74-76, 2000.
72 Aki T. et al. J Allergy Clin Immunol 96: 74-83, 1995.
72A Tsai L. et al. Clin Exp Allergy 29: 1606-1613, 1999.
72B Gafvelin G. et al. J Allergy Clin Immunol 107: 511-518, 2001.
73 van Hage-Hamsten. et al. J. Allergy Clin. Immunol. 91:353, 1993.
74 Varela J. et al. Eur J Biochem 225: 93-98, 1994.
74A Schmidt M. et al. FEBS Lett 370: 11-14, 1995.
75 Eriksson T L J et al. Eur. J. Biochem. 268: 287-294, 2001.
75A Saarne T. et al. Int Arch Allergy Immunol 130: 258-265, 2003.
75B Eriksson T L et al. Eur. J. Biochem. 251 (1-2), 443-447, 1998.
76 Rautiainen J, Rytkonen M, Pelkonen J, Pentikainen J, Perola O, Virtanen T, Zeiler T, Mantyjarvi R. BDA20, a major bovine dander allergen characterised at the sequence level is Bos d 2. Submitted.
77 Gjesing B, Lowenstein H. Ann Allergy 53:602, 1984.
78 de Groot, H. et al. J. Allergy Clin. Immunol. 87:1056-1065, 1991.
79 Konieczny, A. Personal communication; Immunologic Pharmaceutical Corp.
79A Bulone, V. Eur J Biochem 253: 202-211, 1998.
79B Swiss-Prot acc. P81216, P81217.
79C Dandeu J. P. et al. (1993). J. Chromatogr. 621:23-31.
79D Goubran Botros H. et al. 1998. J. Chromatogr. B 710: 57-65.
79E Hilger C. et al. Allergy 52: 179-187; and Hilger C. et al. Gene 169:295-296, 1996.
79F Ichikawa K. et al. Clin Exp Allergy, In Press 2001.
80 Fahlbusch B. et al. Allergy 57: 417-422, 2002.
81 McDonald, B. et al. 1988. J. Allergy Clin. Immunol. 83:251.
81A Clarke, A. J. et al. 1984. EMBO J. 3:1045-1052.
82 Longbottom, J. L. 1983. Characterisation of allergens from the urines of experimental animals. McMillan Press, London, pp. 525-529.
83 Laperche, Y. et al. 1983. Cell 32:453-460.
83A Bush R K et al. 1999. J Allergy Clin Immunol 104:665-671.
83B Aukrust L, Borch S M. 1979. Int Arch Allergy Appl Immunol 60:68-79.
83C Sward-Nordmo M. et al. 1988. Int Arch Allergy Appl Immunol 85:288-294.
84 Shen, et al. J. Allergy Clin. Immunol. 103:S157, 1999.
84A Crameri R. Epidemiology and molecular basis of the involvement of Aspergillus fumigatus in allergic diseases. Contrib. Microbiol. Vol. 2, Karger, Basel (in press).
84B Shen, et al. (manuscript submitted), 1999
84C Shen H D et al. Vacuolar serine proteinase: A major allergen of Aspergillus fumigatus. 10th International Congress of Immunology, Abstract, 1998.
85 Kumar A. et al. 1993. J. Allergy Clin. Immunol. 91:1024-1030.
85A Saxena S. et al. 2003. Clin Exp Immunol 134:86-91.
85B Baur X. et al. Allergy 57: 943-945, 2002.
86A Shen H D et al. 1996. Clin Exp Allergy 26:444-451.
86B Shen, et al. Abstract; The XVIII Congress of the European Academy of Allergology and Clinical Immunology, Brussels, Belgium, 3-7 Jul. 1999.
87 Shen H D et al. Clin Exp Allergy 29: 642-651, 1999.
87A Shen H D et al. Clin Exp Allergy 25: 350-356, 1995.
87B Shen H D et al. J Lab Clin Med 137: 115-124, 2001.
88 Woodfolk J A et al. 1998. J Biol Chem 273:29489-96.
88A Deuell, B. et al. 1991. J. Immunol. 147:96-101.
89 Shen, H. D. et al. 1991. Clin. Exp. Allergy 21:675-681.
89A Horner W E et al. 1995. Int Arch Allergy Immunol 107:298-300.
89B Chang C Y et al. J Biomed Sci 9: 645-655, 2002.
90 Yasueda H. et al. Biochem Biophys Res Commun 248: 240-244, 1998. NB:strain TIMM2782 (Teikyo University Institute for Medical Mycology) equal to strain CBS1878 (Central Bureau von Schimmelkulturen).
90A Onishi Y. et al. Eur J Biochem 261: 148-154, 1999. NB: strain TIMM2782 (Teikyo University Institute for Medical Mycology) equal to strain CBS1878 (Central Bureau von Schimmelkulturen).
91 Schmidt M. et al. Eur J Biochem 246:181-185, 1997. NB: strain ATCC no. 42132 (American Type Culture Collection).
91A Rasool O. et al. Eur J Biochem 267: 4355-4361, 2000. NB: strain ATCC no. 42132 (American Type Culture Collection).
91B NB: strain 4625 (Indian Agricultural Research Institute, PUSA; New Delhi, India).
92 Kuchler, K. et al. 1989. Eur. J. Biochem. 184:249-254.
93 Gmachl, M., and G. Kreil. 1993. Proc. Natl. Acad. Sci. USA 90:3569-3573.
93A Hoffman D R. 1977. J. Allergy Clin. Immunol. 59:364-366.
94 Habermann, E. 1972. Science 177:314-322.
95 Hoffman D R, Jacobson R S. 1996. J. Allergy Clin. Immunol. 97:812-821.
95A Hoffman D R, El-Choufani A E, Smith M M, de Groot H. 2001. Occupational allergy to bumblebee venom: Allergens of Bombus terrestris. J Allergy Clin Immunol In press.
95B Helm R. et al. 1996. J Allerg Clin Immunol 98:172-180.
95C Pomes A. et al. 1998. J Biol Chem 273:30801-30807.
96 Arruda L K et al. J Biol Chem 270:19563-19568, 1995.
97 Arruda L K et al. J Biol Chem 270:31196-31201, 1995.
98 Arruda L K et al. Int Arch Allergy Immunol 107:295-297, 1995.
98A Wu C H et al. 1998. J Allergy Clin Immunol 101:832-840.
98B Melen E. et al. 1999. J Allergy Clin Immunol 103:859-64.
98C Wu C H et al. J Biol Chem 271:17937-17943, 1996.
98D Wu C H et al. Molecular Immunol 34:1-8, 1997.
98E Santos A B R et al. 1999. J Allergy Clin Immunol 104: 329-337.
98F Asturias J A et al. 1999. J Immunol 162:4342-4348.
99 Mazur, G. et al. 1990. Monog. Allergy 28:121-137.
99A Moneo I. et al. Allergy 58: 34-37, 2003.
100 Soldatova, L. et al. 1993. FEBS Letters 320:145-149.
101 Lu, G. et al. 1994. J. Allergy Clin. Immunol. 93:224.
102 Fang, K. S. F. et al. 1988. Proc. Natl. Acad. Sci., USA 85:895-899.
103 King, T. P. et al. 1990. Prot. Seq. Data Anal. 3:263-266.
104 Lu, G. et al. 1993. J. Immunol. 150: 2823-2830.
105 King, T. P. and Lu, G. 1997. Unpublished data.
105A King T P et al. 1996. J. Allergy Clin. Immunol. 98:588-600.
106 Hoffman, D. R. 1993. J. Allergy Clin. Immunol. 92:707-716.

107 Hoffman D R. 1992. Unpublished data.
108 Hoffman D R. J. Allergy Clin. Immunol. 91:187, 1993.
109 Jacobson R S et al. J. Allergy Clin. Immunol. 89:292, 1992.
110 Hoffman D R. J. Allergy Clin. Immunol 91: 71-78, 1993.
111 Schmidt M. et al. FEBS Letters 319: 138-140, 1993.
111A Paddock C D et al. J Immunol 167: 2694-2699, 2001.
112 Elsayed S, Bennich H. Scand J Immunol 3: 683-686, 1974.
113 Elsayed S. et al. Immunochemistry 9: 647-661, 1972.
114 Hoffman, D. R. 1983. J. Allergy Clin. Immunol. 71: 481-486.
115 Langeland, T. 1983. Allergy 38:493-500.
116 Daul C B, Slattery M, Morgan J E, Lehrer S B. 1993. Common crustacea allergens: identification of B cell epitopes with the shrimp specific monoclonal antibodies. In: "Molecular Biology and Immunology of Allergens" (D. Kraft and A. Sehon, eds.). CRC Press, Boca Raton. pp. 291-293.
116A Shanti K N et al. J. Immunol. 151: 5354-5363, 1993.
117 Yu C J et al. J Immunol 170: 445-453, 2003.
117A Miyazawa M et al. J. Allergy Clin. Immunol. 98: 948-953, 1996.
117B Asturias J A et al. Int Arch Allergy Immunol 128: 90-96, 2002.
117C Lopata A L et al. J. Allergy Clin. Immunol. 100: 642-648, 1997.
117D Hoffmann-Sommergruber K. et al. Clin. Exp. Allergy 29: 840-847, 1999.
118 Monsalve R I et al. Biochem. J. 293: 625-632 1993.
118A. Monsalve R I et al. 1997. Clin Exp Allergy 27:833-841.
119 Mena, M. et al. Plant Molec. Biol. 20: 451-458, 1992.
119A Palosuo K. et al. J. Allergy Clin. Immunol. 108: 634-638, 2001.
119B Xu H. et al. Gene 164: 255-259, 1995.
119C Pastorello E A et al. J. Allergy Clin. Immunol. 94: 699-707, 1994.
119D Diaz-Perales A. et al. J Allergy Clin Immunol 110: 790-796, 2002.
119E Galleguillos F, Rodriguez J C. Clin Allergy 8: 21-24, 1978.
119F Baur X. Clin Allergy 9: 451-457, 1979.
119G Gailhofer G. et al. Clin Allergy 18: 445-450, 1988.
120 Menendez-Arias, L. et al. 1988. Eur. J. Biochem. 177: 159-166.
120A Gonzalez R. et al. Lancet 346:48-49, 1995.
120B Kleine-Tebbe J. et al. J Allergy Clin Immunol 110: 797-804, 2002.
120C Sanchez-Monge R. et al. J. Allergy Clin. Immunol. 106: 955-961, 2000.
121 Gavrovic-Jankulovic M. et al. J Allergy Clin Immun of 110: 805-810, 2002.
121A Pastorello E A et al. J. Chromatogr. B Biomed. Sci. Appl. 756: 85-93, 2001.
121B Moneo I. et al. J. Allergy Clin. Immunol. 106: 177-182, 2000.
121C Asturias J A et al. 2000. Allergy 55:898-890.
122 Christie, J. F. et al. 1990. Immunology 69:596-602.
122A Baur X. et al. Clin Allergy 12: 9-17, 1982.
122B Onisuka R. et al. Int Arch Allergy Immunol 125: 135-143, 2001.
123 Czuppon A B et al. J Allergy Clin Immunol 92:690-697, 1993.
124 Attanayaka D P S T G et al. 1991. Plant Mol Biol 16:1079-1081.
125 Chye M L, Cheung K Y. 1995. Plant Mol Biol 26:397-402.
126 Alenius H. et al. 1993. Int Arch Allergy Immunol 102: 61-66.
127 Yeang H Y, Cheong K F, Sunderasan E, Hamzah S, Chew N P, Hamid S, Hamilton R G, Cardosa M J. 1996. The 14.6 kD (REF, Hev b 1) and 24 kD (Hev b 3) rubber particle proteins are recognised by IgE from Spina Bifida patients with Latex allergy. J Allerg Clin Immunol in press.
128 Sunderasan E. et al. 1995. J nat Rubb Res 10:82-99.
129 Swoboda I. et al. 2002. J Immunol. 168:4576-84.
130 Vrtala et al., 2007. J Immunol. 179:1731-1739.
131 Valenta and Niederberger, 2007. J Allergy Clin Immunol. 119(4):826-830.

According to a particularly preferred embodiment of the present invention at least one, preferably at least two, more preferably at least three, in particular all, of the at least three peptides derived from the at least one wild-type allergen is a B cell binding peptide.

"B cell binding peptides" to be used for allergy vaccination according to the invention are derived from or close to the IgE binding sites of allergens but per se show no or minimal IgE reactivity compared to the wild-type allergen (Focke M et al. Clinical & Experimental Allergy 40 (2010):385-397). Requirements for their production and selection are the knowledge of the primary sequence of the allergen and regarding the IgE binding sites. Upon immunization, B cell binding peptides fused to a suitable immunogenic carrier, are capable of inducing the production of allergen-specific IgG which can block IgE binding to the allergen. Whether the IgG induced with the fusion protein can recognize the allergen can be determined, for instance, by testing the IgG for reactivity with the complete allergen. Suitable methods include ELISA, dot blot or Western blot assays. Those peptides are preferred which induce IgG that blocks patients IgE binding to the allergen.

The present invention shows that the use of suitable B cell binding peptides in particular when three or more are fused to a suitable carrier according to the present invention allows the induction of IgG responses which are better focused to the IgE epitopes than those induced by immunization even with a complete allergen. Furthermore, the invention shows that the combination of the appropriate peptides and their number with a suitable carrier can direct the allergen-specific immune response towards a favorable anti-allergic immune response (characterized by the induction of preferentially allergen-specific IgG and not IgE responses and tolerogenic (IL-10) and Th1 (Interferon gamma) cytokine responses.

Moreover, it surprisingly turned out that—despite the fact that they lack allergen-specific T-cell epitopes—polypeptides according to the invention containing 3 or more B cell binding peptides fused to an immunogenic carrier are able reduce allergen-specific T-cell reactions. This is shown by the fact that the presence of allergen-specific IgG induced by therapeutic vaccination with the hypoallergenic polypeptides of the present invention reduces allergen-specific T-cell activation caused by IgE facilitated antigen presentation in PBMCs from vaccinated human allergic individuals. (FIG. 16).

According to a preferred embodiment of the present invention at least one of said at least three peptides exhibits no or reduced IgE-binding capacity compared to the wild-type allergen.

According to another preferred embodiment of the present invention at least one, preferably at least two, more preferably at least three, of said at least three B-cell binding peptides exhibits no or substantially no T-cell reactivity.

The presence of allergen-specific T cell epitopes may give rise to unwanted T cell mediated side effects. Therefore it is particularly preferred to use peptides exhibiting no or substantially no T-cell reactivity in order to obtain the polypeptides of the present invention.

However, also allergen fragments comprising at least one T-cell epitope may be used in the polypeptide according to the present invention.

"Exhibiting reduced IgE-binding capacity", as used herein, means that the molecules according to the present invention show significantly reduced IgE-binding capacity or activity (at least 50% less, preferably at least 70% less, more preferably at least 80% less, even more preferably at least 90% less, most preferably at least 95% less, binding capacity compared to the wild-type allergen) or even lack IgE-binding at all.

IgE-binding activity/capacity of molecules like peptides and proteins can be determined by, for example, an enzyme linked immunosorbent assay (ELISA) using, for example, sera obtained from a subject, (i.e., an allergic subject) that has been previously exposed to the wild-type allergen. Briefly, a peptide to be tested is coated onto wells of a microtiter plate. After washing and blocking the wells, an antibody solution consisting of the plasma of an allergic subject, who has been exposed to the peptide being tested or the protein from which it was derived, is incubated in the wells. A labelled secondary antibody is added to the wells and incubated. The amount of IgE-binding is then quantified and compared to the amount of IgE bound by a purified wild-type allergen.

Alternatively, the binding activity of a peptide can be determined by Western blot analysis. For example, a peptide to be tested is run on a polyacrylamide gel using SDS-PAGE. The peptide is then transferred to nitrocellulose and subsequently incubated with serum from an allergic subject. After incubation with the labelled secondary antibody, the amount of IgE bound is determined and quantified.

Another assay which can be used to determine IgE-binding activity of a peptide is a competition ELISA assay. Briefly, an IgE-antibody pool is generated by combining plasma from allergic subjects who have been shown by direct ELISA to be IgE-reactive with wild-type allergen. This pool is used in ELISA competition assays to compare IgE-binding to wild-type allergen to the peptide tested. IgE-binding for the wild-type allergen and the peptide being tested is determined and quantified.

A "T-cell epitope" means a protein, peptide or polypeptide (e.g., allergen) or fragment thereof, for which a T-cell has an antigen specific binding site, the result of binding to said binding site activates the T-cell. The term "exhibiting reduced T-cell reactivity", as used herein, refers to molecules which exhibit a T-cell reactivity which is significantly reduced compared to the stimulation induced by the wild-type allergen from which the hypoallergenic molecule is derived using equimolar amounts in standard assays known in the art (reduced T-cell reactivity means at least 30%, preferably at least 50%, more preferably at least 70%, most preferably at least 90%, less stimulation of hypoallergenic molecules compared to the wildtype allergen at equimolar amounts). In a particular preferred embodiment of this invention, the molecules may "lack" T-cell epitopes and thus molecule shows reduced T-cell reactivity in the individual(s) to be treated (i.e., who is to receive an epitope-presenting valency platform molecule). It is likely that, for example, an allergen-derived molecule may lack a T-cell epitope(s) with respect to an individual, or a group of individuals, while possessing a T-cell epitope(s) with respect to other individual(s). Methods for detecting the presence of a T-cell epitope are known in the art and include assays which detect T-cell proliferation (such as thymidine incorporation). Immunogens that fail to induce statistically significant incorporation of thymidine above background (i.e., generally p less than 0.05 using standard statistically methods) are generally considered to lack T-cell epitopes, although it will be appreciated that the quantitative amount of thymidine incorporation may vary, depending on the immunogen being tested (see, e.g., Zhen L. et al. (Infect Immun. (2003) 71:3920-3926)). Generally, a stimulation index below about 2-3, more preferably less than about 1, indicates lack of T-cell reactivity and epitopes. The presence of T-cell epitopes can also be determined by measuring secretion of T-cell-derived lymphokines according to standard methods. The stimulation index (SI) may be calculated by dividing the proliferation rate (Thymidine uptake) of stimulated cells through the proliferation rate of unstimulated cells in medium alone. SI=1 means no stimulation, and SI>1 indicates stimulation of cells. Location and content of T-cell epitopes, if present, can be determined empirically.

The cytokine secretion may be determined in addition to the stimulation of T cells. For example, IFN-gamma and IL-10 as biomarkers for increased activity of regulatory T cells have been recognized as cytokines accompanying a successful allergy immunotherapy.

The peptide fragments of the present invention are preferably composed or consist of amino acids 151 to 177, 87 to 117, 1 to 30, 43 to 70 or 212 to 241 of Phl p 1, amino acids 1 to 33, 8 to 39, 34 to 65 or 66 to 96 of Phl p 2, amino acids 93 to 128, 98 to 128, 26 to 53, 26 to 58, 132 to 162, 217 to 246, 252 to 283 or 176 to 212 of Phl p 5, amino acids 23 to 54, 56 to 90, 73 to 114 or 95 to 127 of Phl p 6, amino acids 1 to 34 or 35 to 70 of chain 1 of Fel d 1, amino acids 1 to 34, 35 to 63 or 64 to 92 of chain 2 of Fel d 1, amino acids 30 to 59, 50 to 79, 75 to 104, 30 to 74 or 60 to 104 of Bet v 1, amino acids 1 to 30, 52 to 84 or 188 to 222 of Der p 1, amino acids 1 to 33, 21 to 51, 42 to 73, 62 to 103 or 98 to 129 of Der p 2, amino acids 1 to 30, 20 to 50, 50 to 80, 90 to 125, 125 to 155 or 165 to 198 of Der p 7, amino acids 1-35, 36-70, 71-110, 111-145, 140-170, 175-205, 210-250 or 250-284 of Der p 10, amino acids 1 to 35, 35 to 72, 70 to 100 or 90 to 122 of Der p 21, amino acids 1 to 32, 15 to 48 or 32 to 70, 32 to 60, 52 to 84, 32 to 70 (Cys→Ser) of Der p 23, amino acids 19 to 58, 59 to 95, 91 to 120 or 121 to 157 of Alt a 1, amino acids 31 to 60, 45 to 80, 60 to 96 or 97 to 133 of Par j 2, amino acids 1 to 40, 36 to 66, 63 to 99, 86 to 120 or 107 to 145 of Ole e 1, amino acids 25 to 58, 99 to 133, 154 to 183, 277 to 307, 334 to 363, 373 to 402, 544 to 573, 579 to 608, 58 to 99, 125 to 165, 183 to 224, 224 to 261, 252 to 289, 303 to 340, 416 to 457, 460 to 500 or 501 to 542 of Fel d 2, amino acids 19 to 58, 52 to 91, 82 to 119, 106 to 144 or 139 to 180 of Can f 2, amino acids 19 to 56, 51 to 90, 78 to 118, 106 to 145 or 135-174 of Can f 1, amino acids 27 to 70, 70 to 100 or 92 to 132 of Art v 1, amino acids 31 to 70, 80 to 120, 125 to 155, 160 to 200, 225 to 263, 264 to 300 305 to 350 or 356 to 396 of Amb a 1, amino acids 1 to 34, 35 to 74, 74 to 115, 125 to 165, 174 to 213, 241 to 280, 294 to 333, 361 to 400 or 401 to 438 of Alt a 6, amino acids 1 to 40, 41 to 80, 81 to 120, 121 to 160 of Alt a 2 or fragments or sequence variations thereof.

The specific amino acid sequences of the above identified allergen-derived molecules are (peptides in the following table having an N- and/or C-terminal cysteine residue (C) being used in the polypeptide of the present invention may lack said cysteine residue):

| Peptide | Position | Sequence | SEQ ID No. |
|---|---|---|---|
| Pep Alt a 1.1 | 19-58 | APLESRQDTASCPVTTEGDYVWKISEFYGRKPEGTYYNSL | 23 |
| Pep Alt a 1.2 | 59-95 | GFNIKATNGGTLDFTCSAQADKLEDHKWYSCGENSFM | 24 |
| Pep Alt a 1.3 | 91-120 | ENSFMDFSFDSDRSGLLLKQKVSDDITYVA | 25 |
| Pep Alt a 1.4 | 121-157 | TATLPNYCRAGGNGPKDFVCQGVADAYITLVTLPKSS | 26 |
| Pep Alt a 2.1 | 1-40 | MHSSNNFFKDNIFRSLSKEDPDYSRNIEGQVIRLHWDWAQ | 27 |
| Pep Alt a 2.2 | 41-80 | LLMLSAKRMKVAFKLDIEKDQRVWDRCTADDLKGRNGFKR | 28 |
| Pep Alt a 2.3 | 81-120 | CLQFTLYRPRDLLSLLNEAFFSAFRENRETIINTDLEYAA | 29 |
| Pep Alt a 2.4 | 121-160 | KSISMARLEDLWKEYQKIFPSIQVITSAFRSIEPELTVYT | 30 |
| Pep Alt a 2.5 | 161-190 | CLKKIEASFELIEENGDPKITSEIQLLKAS | 31 |
| Pep Alt a 6.1 | 1-34 | MTITKIHARSVYDSRGNPTVEVDIVTETGLHRAI | 32 |
| Pep Alt a 6.2 | 35-74 | VTETGLHRAIVPSGASTGSHEACELRDGDKSKWGGKGVTK | 33 |
| Pep Alt a 6.3 | 74-115 | APALIKEKLDVKDQSAVDAFLNKLDGTTNKTNLGANAILGVS | 34 |
| Pep Alt a 6.4 | 125-165 | EKGVPLYAHISDLAGTKKPYVLPVPFQNVLNGGSHAGGRLA | 35 |
| Pep Alt a 6.5 | 174-213 | CEAPTFSEAMRQGAEVYQKLKALAKKTYGQSAGNVGDEGG | 36 |
| Pep Alt a 6.6 | 241-280 | IKIAMDVASSEFYKADEKKYDLDFKNPDSDKSKWLTYEQL | 37 |
| Pep Alt a 6.7 | 294-333 | VSIEDPFAEDDWEAWSYFFKTYDGQIVGDDLTVTNPEFIK | 38 |
| Pep Alt a 6.8 | 361-400 | AKDAFGAGWGVMVSHRSGETEDVTIADIVVGLRSGQIKTG | 39 |
| Pep Alt a 6.9 | 401-438 | APARSERLAKLNQILRIEEELGDNAVYAGNNFRTAVNL | 40 |
| Pep Amb a 1.1 | 31-70 | EILPVNETRRLTTSGAYNIIDGCWRGKADWAENRKALADC | 41 |
| Pep Amb a 1.2 | 80-120 | GGKDGDIYTVTSELDDDVANPKEGTLRFGAAQNRPLWIIFE | 42 |
| Pep Amb a 1.3 | 125-155 | IRLDKEMVVNSDKTIDGRGAKVEIINAGFTL | 43 |
| Pep Amb a 1.4 | 160-200 | NVIIHNINMHDVKVNPGGLIKSNDGPAAPRAGSDGDAISIS | 44 |
| Pep Amb a 1.5 | 225-263 | GTTRLTVSNSLFTQHQFVLLFGAGDENIEDRGMLATVAF | 45 |
| Pep Amb a 1.6 | 264-300 | NTFTDNVDQRMPRCRHGFFQVVNNNYDKWGSYAIGGS | 46 |
| Pep Amb a 1.7 | 305-350 | ILSQGNRFCAPDERSKKNVLGRHGEAAAESMKWNWRTNKDVLENGA | 47 |
| Pep Amb a 1.8 | 356-396 | GVDPVLTPEQSAGMIPAEPGESALSLTSSAGVLSCQPGAPC | 48 |
| Pep Art v 1.1 | 27-70 | SKLCEKTSKTYSGKCDNKKCDKKCIEWEKAQHGACHKREAGKES | 49 |
| Pep Art v 1.2 | 70-100 | SCFCYFDCSKSPPGATPAPPGAAPPPAAGGS | 50 |
| Pep Art v 1.3 | 92-132 | APPPAAGGSPSPPADGGSPPPPADGGSPPVDGGSPPPPSTH | 51 |
| Can f 1 Pep 1 | 19-56 | QDTPALGKDTAVSGKWYLKAMTADQEVPEKPDSVTPM | 52 |

-continued

| Peptide | Position | Sequence | SEQ ID No. |
|---|---|---|---|
| Can f 1 Pep 2 | 51-90 | DSVTPMILKAQKGGNLEAKITMLTNGQCQNITVVLHKTSE | 53 |
| Can f 1 Pep 3 | 78-118 | CQNITVVLHKTSEPGKYTAYEGQRVVFIQPSPVRDHYILYC | 54 |
| Can f 1 Pep 4 | 106-145 | QPSPVRDHYILYCEGELHGRQIRMAKLLGRDPEQSQEALE | 55 |
| Can f 1 Pep 5 | 135-174 | RDPEQSQEALEDFREFSRAKGLNQEILELAQSETCSPGGQ | 56 |
| Can f 2 Pep 1 | 19-58 | QEGNHEEPQGGLEELSGRWHSVALASNKSDLIKPWGHFRV | 57 |
| Can f 2 Pep 2 | 52-91 | PWGHFRVFIHSMSAKDGNLHGDILIPQDGQCEKVSLTAFK | 58 |
| Can f 2 Pep 3 | 82-119 | CEKVSLTAFKTATSNKFDLEYWGHNDLYLAEVDPKSYL | 59 |
| Can f 2 Pep 4 | 106-144 | NDLYLAEVDPKSYLILYMINQYNDDTSLVAHLMVRDLSR | 60 |
| Can f 2 Pep 5 | 139-180 | VRDLSRQQDFLPAFESVCEDIGLHKDQIVVLSDDDRCQGSRD | 61 |
| Fel d 2 Pep 1 | 25-58 | EAHQSEIAHRFNDLGEEHFRGLVLVAFSQYLQQC | 62 |
| Fel d 2 Pep 2 | 99-133 | CTVASLRDKYGEMADCCEKKEPERNECFLQHKDDN | 63 |
| Fel d 2 Pep 3 | 154-183 | NEQRFLGKYLYEIARRHPYFYAPELLYYAE | 64 |
| Fel d 2 Pep 4 | 277-307 | CADDRADLAKYICENQDSISTKLKECCGKPV | 65 |
| Fel d 2 Pep 5 | 334-363 | VEDKEVCKNYQEAKDVFLGTFLYEYSRRHP | 66 |
| Fel d 2 Pep 6 | 373-402 | LAKEYEATLEKCCATDDPPACYAHVFDEFK | 67 |
| Fel d 2 Pep 7 | 544-573 | EKQIKKQSALVELLKHKPKATEEQLKTVMG | 68 |
| Fel d 2 Pep 8 | 579-608 | VDKCCAAEDKEACFAEEGPKLVAAAQAALA | 69 |
| Fel d 2 Pep 9 | 58-99 | CPFEDHVKLVNEVTEFAKGCVADQSAANCEKSLHELLGDKLC | 70 |
| Fel d 2 Pep 10 | 125-165 | CFLQHKDDNPGFGQLVTPEADAMCTAFHENEQRFLGKYLYE | 71 |
| Fel d 2 Pep 11 | 183-224 | EEYKGVFTECCEAADKAACLTPKVDALREKVLASSAKERLKC | 72 |
| Fel d 2 Pep 12 | 224-261 | CASLQKFGERAFKAWSVARLSQKFPKAEFAEISKLVTD | 73 |
| Fel d 2 Pep 13 | 252-289 | FAEISKLVTDLAKIHKECCHGDLLECADDRADLAKYIC | 74 |
| Fel d 2 Pep 14 | 303-340 | CGKPVLEKSHCISEVERDELPADLPPLAVDFVEDKEVC | 75 |
| Fel d 2 Pep 15 | 416-457 | CELFEKLGEYGFQNALLVRYTKKVPQVSTPTLVEVSRSLGKV | 76 |
| Fel d 2 Pep 16 | 460-500 | CTHPEAERLSCAEDYLSVVLNRLCVLHEKTPVSERVTKC | 77 |
| Fel d 2 Pep 17 | 501-542 | CTESLVNRRPCFSALQVDETYVPKEFSAETFTFHADLCTLPE | 78 |
| Pep Ole e 1.1 | 1-40 | EDIPQPPVSQFHIQGQVYCDTCRAGFITELSEFIPGASLR | 79 |
| Pep Ole e 1.2 | 36-66 | GASLRLQCKDKENGDVTFTEVGYTRAEGLYS | 80 |
| Pep Ole e 1.3 | 63-99 | GLYSMLVERDHKNEFCEITLISSGRKDCNEIPTEGWA | 81 |
| Pep Ole e 1.4 | 86-120 | GRKDCNEIPTEGWAKPSLKFKLNTVNGTTRTVNPL | 82 |
| Pep Ole e 1.5 | 107-145 | LNTVNGTTRTVNPLGFFKKEALPKCAQVYNKLGMYPPNM | 83 |

-continued

| Peptide | Position | Sequence | SEQ ID No. |
|---|---|---|---|
| Pep Par j 2.1 | 31-60 | GEEACGKVVQDIMPCLHFVKGEEKEPSKEC | 84 |
| Pep Par j 2.2 | 45-80 | CLHFVKGEEKEPSKECCSGTKKLSEEVKTTEQKREA | 85 |
| Pep Par j 2.3 | 60-96 | CCSGTKKLSEEVKTTEQKREACKCIVRATKGISGIKN | 86 |
| Pep Par j 2.4 | 97-133 | ELVAEVPKKCDIKTTLPPITADFDCSKIQSTIFRGYY | 87 |
| Der p 1 Pep 1 | 1-30 | TNACSINGNAPAEIDLRQMRTVTPIRMQGG | 88 |
| Der p 1 Pep 2 | 52-84 | NQSLDLAEQELVDCASQHGCHGDTIPRGIEYIQ | 89 |
| Der p 1 Pep 3 | 85-115 | HNGVVQESYYRYVAREQSCRRPNAQRFGISN | 90 |
| Der p 1 Pep 4 | 99-135 | REQSCRRPNAQRFGISNYCQIYPPNVNKIREALAQTH | 91 |
| Der p 1 Pep 5 | 145-175 | KDLDAFRHYDGRTIIQRDNGYQPNYHAVNIV | 92 |
| Der p 1 Pep 6 | 155-187 | GRTIIQRDNGYQPNYHAVNIVGYSNAQGVDYWI | 93 |
| Der p 1 Pep 7 | 175-208 | VGYSNAQGVDYWIVRNSWDTNWGDNGYGYFAANI | 94 |
| Der p 1 Pep 8 | 188-222 | VRNSWDTNWGDNGYGYFAANIDLMMIEEYPYVVIL | 95 |
| Der p 1 Pep 1.2 | 1-41 | TNACSINGNAPAEIDLRQMRTVTPIRMQGGCGSCWAFSGVA | 143 |
| Der p 1 Pep 2.2 | 42-82 | ATESAYLAYRNQSLDLAEQELVDCASQHGCHGDTIPRGIEYIQ | 144 |
| Der p 1 Pep 9 | 27-57 | MQGGCGSCWAFSGVAATESAYLAYRNQSLD | 145 |
| Der p 2 Pep 1 | 1-33 | DQVDVKDCANHEIKKVLVPGCHGSEPCIIHRGK | 96 |
| Der p 2 Pep 2 | 21-51 | CHGSEPCIIHRGKPFQLEAVFEANQNSKTAK | 97 |
| Der p 2 Pep 3 | 42-73 | EANQNSKTAKIEIKASIEGLEVDVPGIDPNAC | 98 |
| Der p 2 Pep 4 | 62-103 | EVDVPGIDPNACHYMKCPLVKGQQYDIKYTWIVPKIAPKSEN | 99 |
| Der p 2 Pep 5 | 98-129 | APKSENVVVTVKVMGDNGVLACAIATHAKIRD | 100 |
| Der p 5 Pep 1 | 1-35 | MEDKKHDYQNEFDFLLMERIHEQIKKGELALFYLQ | 101 |
| Der p 5 Pep 2 | 25-60 | KKGELALFYLQEQINHFEEKPTKEMKDKIVAEMDTI | 102 |
| Der p 5 Pep 3 | 65-95 | DGVRGVLDRLMQRKDLDIFEQYNLEMAKKSG | 103 |
| Der p 5 Pep 4 | 78-114 | DLDIFEQYNLEMAKKSGDILERDLKKEEARVKKIEV | 104 |
| Der p 7 Pep 1 | 1-30 | DPIHYDKITEEINKAVDEAVAAIEKSETFD | 105 |
| Der p 7 Pep 2 | 20-50 | VAAIEKSETFDPMKVPDHSDKFERHIGIIDL | 106 |
| Der p 7 Pep 3 | 50-80 | LKGELDMRNIQVRGLKQMKRVGDANVKSEDG | 107 |
| Der p 7 Pep 4 | 90-125 | VHDDVVSMEYDLAYKLGDLHPNTHVISDIQDFVVEL | 108 |
| Der p 7 Pep 5 | 125-155 | LSLEVSEEGNMTLTSFEVRQFANVVNHIGGL | 109 |
| Der p 7 Pep 6 | 165-198 | LSDVLTAIFQDTVRAEMTKVLAPAFKKELERNNQ | 110 |
| Der p 10 Pep 1 | 1-35 | MEAIKKKMQAMKLEKDNAIDRAEIAEQKARDANLR | 111 |
| Der p 10 Pep 2 | 36-70 | AEKSEEEVRALQKKIQQIENELDQVQEQLSAANTK | 112 |
| Der p 10 Pep 3 | 71-110 | LEEKEKALQTAEGDVAALNRRIQLIEEDLERSEERLKIAT | 113 |
| Der p 10 Pep 4 | 111-145 | AKLEEASQSADESERMRKMLEHRSITDEERMEGLE | 114 |
| Der p 10 Pep 5 | 140-170 | RMEGLENQLKEARMMAEDADRKYDEVARKLA | 115 |
| Der p 10 Pep 6 | 175-205 | DLERAEERAETGESKIVELEEELRVVGNNLK | 116 |

-continued

| Peptide | Position | Sequence | SEQ ID No. |
|---|---|---|---|
| Der p 10 Pep 7 | 210-250 | SEEKAQQREEAHEQQIRIMTTKLKEAEARAEFAERSVQKLQ | 117 |
| Der p 10 Pep 8 | 250-284 | QKEVDRLEDELVHEKEKYKSISDELDQTFAELTGY | 118 |
| Der p 21 Pep 1 | 1-35 | MFIVGDKKEDEWRMAFDRLMMEELETKIDQVEKGL | 119 |
| Der p 21 Pep 2 | 35-72 | LHLSEQYKELEKTKSKELKEQILRELTIGENFMKGAL | 120 |
| Der p 21 Pep 3 | 70-100 | GALKFFEMEAKRTDLNMFERYNYEFALESIK | 121 |
| Der p 21 Pep 4 | 90-122 | YNYEFALESIKLLIKKLDELAKKVKAVNPDEYY | 122 |
| Der p 23 Pep 1 | 1-32 | MANDNDDDPTTTVHPTTTEQPDDKFECPSRFG | 123 |
| Der p 23 Pep 2 | 15-48 | PTTTEQPDDKFECPSRFGYFADPKDPHKFYICSN | 124 |
| Der p 23 Pep 3 | 32-70 | GYFADPKDPHKFYICSNWEAVHKDCPGNTRWNEDEETCT | 125 |
| Der p 23 Pep 4 | 32-60 | GYFADPKDPHKFYICSNWEAVHKDCPGNT | 146 |
| Der p 23 Pep 5 | 42-70 | KFYICSNWEAVHKDCPGNTRWNEDEETCT | 147 |
| Der p 23 Pep 6 | 32-70* (Cys ->Ser) | GYFADPKDPHKFYISSNWEAVHKDSPGNTRWNEDEEST | 148 |
| Bet v 1 Pep 1 | 30-59 | LFPKVAPQAISSVENIEGNGGPGTIKKISF | 126 |
| Bet v 1 Pep 2 | 50-79 | GPGTIKKISFPEGFPFKYVKDRVDEVDHTN | 127 |
| Bet v 1 Pep 3 | 75-104 | VDHTNFKYNYSVIEGGPIGDTLEKISNEIK | 128 |
| Bet v 1 Pep A | 30-74 | LFPKVAPQAISSVENIEGNGGPGTIKKISFPEGFPFKYVKDRVDE | 143 |
| Bet v 1 Pep B | 60-104 | PEGFPFKYVKDRVDEVDHTNFKYNYSVIEGGPIGDTLEKISNEIKI | 144 |
| Fel d 1 chain 1 Pep 1 | 1-34 | EICPAVKRDVDLFLTGTPDEYVEQVAQYKALPVVC | 129 |
| Fel d 1 chain 1 Pep 2 | 35-70 | LENARILKNCVDAKMTEEDKENALSLLDKIYTSPLC | 130 |
| Fel d 1 chain 2 Pep 1 | 1-34 | VKMAITCPIFYDVFFAVANGNELLLDLSLTKVNAC | 131 |
| Fel d 1 chain 2 Pep 2 | 35-63 | TEPERTAMKKIQDCYVENGLISRVLDGLVC | 132 |
| Fel d 1 chain 2 Pep 3 | 64-92 | CMTTISSSKDCMGEAVQNTVEDLKLNTLGR | 133 |
| Phl p 5 Pep 1 | 98-128 | CGAASNKAFAEGLSGEPKGAAESSSKAALTSK | 134 |
| Phl p 5 Pep 2 | 26-58 | ADLGYGPATPAAPAAGYTPATPAAPAEAAPAGKC | 135 |
| Phl p 5 Pep 3 | 132-162 | AYKLAYKTAEGATPEAKYDAYVATLSEALRIC | 136 |
| Phl p 5 Pep 4 | 217-246 | CEAAFNDAIKASTGGAYESYKFIPALEAAVK | 137 |
| Phl p 5 Pep 5 | 252-283 | TVATAPEVKYTVFETALKKAITAMSEAQKAAKC | 138 |
| Phl p 5 Pep 6 | 176-212 | CAEEVKVIPAGELQVIEKVDAAFKVAATAANAAPANDK | 139 |
| Phl p 5 Pep 1a | 93-128 | CFVATFGAASNKAFAEGLSGEPKGAAESSSKAALTSK | 141 |
| Phl p 5 Pep 2b | 26-53 | ADLGYGPATPAAPAAGYTPATPAAPAEAC | 142 |
| Phl p 5 Pep 7 | 59-91 | ATTEEQKLIEKINAGFKAALAAAAGVQPADKYR | 22 |
| Phl p 1 Pep 1 | 151-171 | HVEKGSNPNYLALLVKYVNGDGDVVAVC | 1 |

-continued

| Peptide | Position | Sequence | SEQ ID No. |
|---|---|---|---|
| Phl p 1 Pep 2 | 87-117 | EPVVVHITDDNEEPIAPYHFDLSGHAFGAMAC | 2 |
| Phl p 1 Pep 3 | 1-30 | IPKVPPGPNITATYGDKWLDAKSTWYGKPTGC | 3 |
| Phl p 1 Pep 4 | 43-70 | GYKDVDKPPFSGMTGCGNTPIFKSGRGC | 4 |
| Phl p 1 Pep 5 | 212-241 | CVRYTTEGGTKTEAEDVIPEGWKADTSYESK | 5 |
| Phl p 2 Pep 1 | 1-33 | VPKVTFTVEKGSNEKHLAVLVKYEGDTMAEVELC | 6 |
| Phl p 2 Pep 2 | 28-39 | CVEKGSNEKHLAVLVKYEGDTMAEVELREHGSD | 7 |
| Phl p 2 Pep 3 | 34-65 | REHGSDEWVAMTKGEGGVWTFDSEEPLQGPFNC | 8 |
| Phl p 2 Pep 4 | 66-96 | CFRFLTEKGMKNVFDDVVPEKYTIGATYAPEE | 9 |
| Phl p 6 Pep 1 | 23-54 | GKATTEEQKLIEDVNASFRAAMATTANVPPAD | 10 |
| Phl p 6 Pep 2 | 56-90 | YKTFEAAFTVSSKRNLADAVSKAPQLVPKLDEVYN | 11 |
| Phl p 6 Pep 3 | 95-127 | AADHAAPEDKYEAFVLHFSEALRIIAGTPEVHA | 12 |
| Phl p 6 Pep 4 | 73-114 | DAVSKAPQLVPKLDEVYNAAYNAADHAAPEDKY | 13 |

*)Cysteins exchanged with serins (marked in bold)

The terms "fragments thereof" and "sequence variations thereof" refer to peptides which are deduced from the allergen-derived molecules disclosed herein and show biochemical properties (e.g. the capacity to prevent IgE binding to the allergen from which those molecules are derived from) which are comparable or identical to said allergen-derived molecules. The fragments of the present invention comprise at least 5, preferably at least 7, more preferably at least 10, successive and/or a maximum of 95%, preferably a maximum of 90%, more preferably a maximum of 80% amino acid residues of the allergen-derived molecule. The term "sequence variation" includes modifications of the peptides such as fragmentation (see above), amino acid substitutions (in particular cysteine or methionine residues may be exchanged with serine, alanine or other natural or non-natural amino acids or amino acid derivatives), deletions or additions. "Sequence variation" refers also to said allergen-derived molecules of the above table, wherein at least 1, preferably at least 2, more preferably at least 3, even more preferably at least 4 (5, 6, 7, 8, 9, 10, 15, 20) amino acid residues are added to the C- and/or N-terminus.

It is noted that the allergen referred to herein as "clone 30 allergen" is an allergen derived from the house dust mite Dermatophagoides pteronyssinus and consists of the following sequence: MANDNDDDPTTTVHPTTTEQPDDK-FECPSRFGYFADPKDPHKFYICSN-WEAVHKDCPGNTRWNEDEETCT (SEQ ID No. 140; see also WO 2007/124524). In the meantime, the allergen name Der p 23 has been assigned to clone 30 allergen. This means that Der p 23 and clone 30 allergen are synonyms.

According to the present invention also peptides are encompassed which are at least 80% identical, preferably 90% identical, to the amino sequences disclosed above.

According to a preferred embodiment of the present invention the surface polypeptide of the virus of the hepadnaviridae family or at least one fragment thereof comprises at least two B-cell binding peptide fragments derived from at least one wild-type allergen fused to its N-terminus and at least two B-cell binding peptide fragments derived from at least one wild-type allergen fused to its C-terminus.

In a particularly preferred embodiment of the present invention at least two of said at least three B-cell binding peptides are identical.

The polypeptide of the present invention can be used as vaccine in the treatment or prevention of an allergy in a human or animal.

The polypeptide is preferably administered to an individual in the amount of 0.01 microgram per kg body weight to 5 mg/kg body weight, pref-erably 0.1 microgram per kg body weight to 10 microgram per kg body weight.

According to a particularly preferred embodiment of the present invention the polypeptides of the present invention are administered to an individual in an amount of at least 10 μg, preferably at least 20 μg, per polypeptide. The maximum amount of polypeptides to be administered can be varied but is preferably below 100 μg, more preferably below 50 μg, even more preferably 40 μg or less, per polypeptide.

The amount of polypeptides that may be combined with excipients to produce a single dosage form will vary depending upon the host treated and the particular mode of administration. The dose of the vaccine may vary according to factors such as the disease state, age, sex and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances. For instance, the polypeptides and vaccine of the present invention may be administered to an individual at intervals of several days, one or two weeks or even months depending always on the level of allergen-specific IgG induction.

In a preferred embodiment of the present invention the polypeptide/vaccine is applied between 2 and 10, preferably between 2 and 7, even more preferably up to 5 and most preferably up to 3 times. In a particularly preferred embodiment the time interval between the subsequent vaccinations is chosen to be between 2 weeks and 5 years, preferably between 1 month and up to 3 years, more preferably between 2 months and 1.5 years. The repeated administration of the peptide/vaccine of the present invention may maximize the final effect of a therapeutic vaccination.

According to a particularly preferred embodiment of the present invention three or more B-cell binding peptides selected from the group consisting of SEQ ID No. 1, SEQ ID No. 2, SEQ ID No. 5, SEQ ID No. 9, SEQ ID No. 137, SEQ ID No. 139, SEQ ID No. 142 and SEQ ID No. 10 are bound N- and C-terminally to a surface polypeptide of the virus of the hepadnaviridae family, preferably the hepatitis PreS polypeptide or fragments thereof.

The polypeptides of the present invention comprising the at least three B-cell binding peptides derived from at least one wild-type allergen are preferably selected from the group consisting of SEQ ID No. 14, SEQ ID No. 15, SEQ ID No. 16, SEQ ID No. 17, SEQ ID No. 18 and SEQ ID No. 19.

Another aspect of the present invention relates to a nucleic acid molecule encoding a polypeptide according to the present invention.

Another aspect of the present invention relates to a vector comprising a nucleic acid molecule according to the present invention.

Said vector is preferably an expression vector.

The vector harbouring the nucleic acid molecule of the present invention may be used for cloning purposes or for the production of expression vectors. Said vector can be a plasmid, cosmid, virus, bacteriophage or any other vector commonly used in genetic engineering, and can include, in addition to the nucleic acid molecule of the invention, eukaryotic or prokaryotic elements for the control of the expression, such as regulatory sequences for the initiation and the termination of the transcription and/or translation, enhancers, promoters, signal sequences and the like.

According to a preferred embodiment of the present invention the vector is a bacterial, fungal, insect, viral or mammalian vector.

The vector of the present invention may preferably be employed for cloning and expression purposes in various hosts like bacteria, yeasts, filamentous fungi, mammalian cells, insect cells, plant cells or any other prokaryotic or eukaryotic cells. Therefore, said vector comprises besides a nucleic acid encoding for a hypoallergenic molecule or fusion protein according to the present invention host specific regulatory sequences.

Another aspect of the present invention relates to a host comprising a nucleic acid molecule or a vector according to the present invention.

The nucleic acid molecule and the vector according to the present invention may be introduced into a suitable host. Said molecule may be incorporated into the genome of the host. The vector may exist extrachromosomally in the cytoplasm or incorporated into the chromosome of the host.

Yet another aspect of the present invention relates to an antibody directed against a hypoallergenic molecule, hypoallergenic fusion protein or a fusion protein according to the present invention.

Another aspect of the present invention relates to a vaccine formulation comprising at least one, preferably at least two, more preferably at least three, even more preferably at least 4, polypeptide according to the present invention.

In a particularly preferred embodiment of the present invention the vaccine comprises at least one, preferably at least two, preferably at least three, preferably at least four, preferably at least 5, polypeptides having an amino acid sequence selected from the group consisting of SEQ ID No. 14, SEQ ID No. 15, SEQ ID No. 16, SEQ ID No. 17, SEQ ID No. 18, SEQ ID No. 19, SEQ ID No. 20, SEQ ID No. 149, SEQ ID No. 150, SEQ ID No. 151 and SEQ ID No. 152.

Depending on the composition such a vaccine can be used in the treatment and/or prevention of grass pollen allergies, birch pollen allergies, house dust mite allergies or a combination of those allergies in individuals suffering from such allergies or being at risk to suffer therefrom.

The term "preventing", as used herein, covers measures not only to prevent the occurrence of disease, such as risk factor reduction, but also to arrest its progress and reduce its consequences once established. "Preventing" means also to prevent sensitization of an individual being at risk to get an allergy.

As used herein, the term "treatment" or grammatical equivalents encompasses the improvement and/or reversal of the symptoms of disease (e.g., allergy). A compound which causes an improvement in any parameter associated with disease when used in the screening methods of the instant invention may thereby be identified as a therapeutic compound. The term "treatment" refers to both therapeutic treatment and prophylactic or preventative measures.

According to one of the most preferred embodiment of the present invention the vaccine comprises polypeptides having amino acid sequence SEQ ID No. 14, SEQ ID No. 15, SEQ ID No. 16 and SEQ ID No. 17.

According to another preferred embodiment of the present invention the vaccine comprises polypeptides having amino acid sequence SEQ ID No. 18 and/or SEQ ID No. 19.

According to a particularly preferred embodiment of the present invention the vaccine comprises polypeptides of the present invention which comprise allergen fragments derived from house dust mite allergens. Particularly preferred are amino acid residues 1 to 33, 21 to 51, 42 to 73, 62 to 103 or 98 to 129 of Der p 2, amino acid residues 1 to 30, 20 to 50, 50 to 80, 90 to 125, 125 to 155 or 165 to 198 of Der p 7, amino acid residues 1 to 35, 35 to 72, 70 to 100 or 90 to 122 of Der p 21, amino acids 1 to 32, 15 to 48 or 32 to 70, 32 to 60, 52 to 84, 32 to 70 (Cys→Ser) of Der p 23, amino acid residues 1 to 30, 1 to 41, 27 to 57, 42 to 82, 52 to 84, 85 to 115, 99 to 135, 145 to 175, 155 to 187, 175 to 208 or 188 to 222 of Der p 1. Most preferably, the vaccine comprises at least one of the polypeptides SEQ ID No. 149 to 152 (shown in FIG. 18A-D).

In a particularly preferred embodiment the polypeptide/vaccine of the present invention is administered 4 times per treatment year over a total treatment period of 1 to 5 years, preferably over 2 to 3 years. Of said 4 yearly administrations 3 are applied within a period of 6 to 12, preferably 8, weeks having intervals of 3 to 6 weeks, preferably 4 weeks, between administration 1 and 2 and another 3 to 6 weeks, preferably 4 weeks, between administration 2 and 3. The fourth administration is applied 3 to 7 months after the third administration. If the total treatment period exceeds 1 year, the same dosing regimen is applied in the following treatment years.

For the treatment of seasonal allergies (e.g. pollen allergies such as grass pollen allergy or birch pollen allergy) administration 1, 2, and 3 are preferably scheduled before the respective season with allergen exposure (pollen season), and the fourth administration is scheduled after the season.

The vaccine formulation according to the present invention may be formulated as known in the art and necessarily adapted to the way of administration of said vaccine formulation.

Preferred ways of administration of the vaccine formulation (of the present invention) include all standard administration regimes described and suggested for vaccination in general and allergy immunotherapy specifically (orally, transdermally, intraveneously, intranasally, via mucosa, rectally, etc). However, it is particularly preferred to administer the molecules and proteins according to the present invention subcutaneously or intramusculary.

The vaccine formulation according to the present invention may only comprise a viral capsid protein or fragments thereof of a member of the genus of hepadnaviridae.

Said formulation preferably further comprises at least one adjuvant, pharmaceutical acceptable excipient and/or preservative.

In order to increase the immunogenicity of the hypoallergenic molecules according to the present invention, adjuvants, for instance, may be used in a medicament according to the present invention. An adjuvant according to the present invention is an auxiliary agent which, when administered together or in parallel with an antigen, increases its immunogenicity and/or influences the quality of the immune response. Hence, the adjuvant can, e.g., considerably influence the extent of the humoral or cellular immune response. Customary adjuvants are, e.g., aluminum compounds, lipid-containing compounds or inactivated mycobacteria.

Generally, adjuvants can be of different forms, provided that they are suitable for administration to human beings. Further examples of such adjuvants are oil emulsions of mineral or vegetal origin, mineral compounds such as aluminium phosphate or hydroxide, or calcium phosphate, bacterial products and derivatives, such as P40 (derived from the cell wall of *Corynebacterium granulosum*), monophosphoryl lipid A (MPL, derivative of LPS) and muramyl peptide derivatives and conjugates thereof (derivatives from mycobacterium components), alum, incomplete Freund's adjuvant, liposyn, saponin, squalene, etc. (see, e.g., Gupta R. K. et al. (Vaccine 11:293-306 (1993)) and Johnson A. G. (Clin. Microbiol. Rev. 7:277-289). The medicament of the present invention comprises most preferably alum as adjuvant.

Another preferred embodiment of the present invention is a combination of more than one fusion protein containing hypoallergenic peptides and the hepatitis B pre S protein. These combinations may be derived from peptides from a single allergen or from different allergens of the same allergen source or from several different allergen source.

A preferred embodiment of the present invention relates to a mixture of four fusion proteins containing hypoallergenic peptides from Phl p 1, Phl p 2, Phl p 5, and Phl p 6 and the hepatitis B virus preS protein.

Another preferred embodiment of the present invention relates to a fusion protein or a mixture of 2 fusion proteins containing hypoallergenic peptides from Bet v 1 and the hepatitis B virus PreS protein.

Yet another preferred embodiment of the present invention relates to a mixture of at least 2 fusion proteins containing hypoallergenic peptides from house dust mite allergens, most preferably selected from Der p 1, Der p 2, Der p 5, Der p 7, Der p 21 and Der p 23 and the hepatitis B virus PreS protein. Most preferably, the mixture contains 3 fusion proteins containing hypoallergenic peptides derived from Der p 1, Der p 2, and Der p 23. It is particularly preferred that the mixture comprises at least one, preferably at least two, more preferably at least three, of the polypeptides shown in SEQ ID No. 149 to 152 (see also FIG. 18A-D).

Generally, specific vaccine formulations according to the present invention can be prepared for the treatment or prevention of different allergies by combination of hypoallergenic polypeptides of the invention representing the clinically relevant allergens of an allergen source. Methods to determine the clinically relevant allergens of an allergen source are known in the art and have been described before (Valenta and Niederberger, 2007, J Allergy Clin Immunol, 119 (4): 826-830). In a preferred embodiment, the hypoallergenic polypeptides of said specific vaccine formulation are adsorbed to an adjuvant which can be used in human (e.g. aluminium hydroxide), and the mixture is administered 3-4 times per year for 1-3 years applying more than 10 μg of each polypeptide present in the vaccine formulation per dose.

According to another preferred embodiment of the present invention said formulations comprise 10 ng to 1 g, preferably 100 ng to 10 mg, especially 0.5 μg to 200 μg of said hypoallergenic molecule or antibody.

Another aspect of the present invention relates to the use of a hypoallergenic protein or an antibody according to the present invention for manufacturing a medicament for the treatment or prevention of a viral infection and/or an allergy in a human or animal.

Said medicament preferably further comprises at least one adjuvant, pharmaceutical acceptable excipient and/or preservative.

The medicament according to the present invention may be used for active (administration of the hypoallergenic protein and/or molecules of the invention) as well as for passive immunization (antibodies directed to the hypoallergenic protein and/or molecules of the invention).

According to a preferred embodiment of the present invention said medicament comprises 10 ng to 1 g, preferably 100 ng to 10 mg, especially 0.5 μg to 200 μg of said hypoallergenic molecule, nucleic acid molecule, vector, host or antibody.

The medicament is preferably administered to an individual in amount of 0.01 μg/kg body weight to 5 mg/kg body weight, preferably 0.1 μg/kg body weight to 10 μg/kg body weight.

In a particularly preferred embodiment, the medicament is administered in a dose containing an absolute amount of 5-200 μg, more preferably 10-80 μg, most preferably 20-40 μg of each included hypoallergenic polypeptide The particular dosage regimen, i.e., dose, timing and repetition, will depend on the particular individual and that individual's medical history. Empirical considerations, such as the half life, will generally contribute to determination of the dosage. Frequency of administration may be determined and adjusted over the course of therapy.

Most preferably, the dosing regimen for the medicament will consist of 4 yearly subcutaneous injections of one and the same dose over a total treatment period of 2 to 3 years. Of said 4 yearly subcutaneous injections 3 are applied within a period of 6 to 12, preferably 8, weeks having intervals of 3 to 6 weeks, preferably 4 weeks, between injection 1 and 2 and another 3 to 6 weeks, preferably 4 weeks, between injection 2 and 3. The fourth injection is applied 4 to 6 months after the third administration. The same dosing regimen is applied in the following treatment years.

For the treatment of seasonal allergies (e.g. pollen allergies such as grass pollen allergy or birch pollen allergy) administration 1, 2, and 3 are preferably scheduled before the respective season with allergen exposure (pollen season), and the fourth administration is scheduled after the season.

The individual to whom the medicament according to the present invention is administered is preferably an individual or animal which is having or is at risk of having an allergy.

Subjects having or at risk of having an allergy, allergic condition, allergic disorder or allergic disease include subjects with an existing allergic condition or a known or a suspected predisposition towards developing a symptom associated with or caused by an allergic condition. Thus, the subject can have an active chronic allergic condition, disorder or disease, an acute allergic episode, or a latent allergic condition, disorder or disease. Certain allergic conditions are associated with seasonal or geographical environmental factors. Thus, at risk subjects include those at risk from suffering from a condition based upon a prior personal or family history, and the season or physical location, but which the condition or a symptom associated with the condition may not presently manifest itself in the subject.

The administration of the medicament according to the present invention, which comprises at least one hypoallergenic molecule as described herein, to an individual may prevent sensitization of said individual or may induce an appropriate immune response to allergens. If the medicament of the present invention is used to prevent sensitization, it should be administered to an individual prior to the first contact with said allergen. Therefore, it is preferred to administer the medicament according to the present invention to neonates and children. It turned out that also the administration of the medicament according to the present invention to pregnant individuals will induce the formation of antibodies directed against allergens in the unborn child. It is especially beneficial to use hypoallergenic molecules according to the present invention for such therapies, because due to the lack of allergen-specific T-cell epitopes side effects occurring in the course of allergen immunotherapy can significantly be reduced or even be completely avoided.

Another aspect of the present invention relates to the use of a viral capsid protein from a virus of the family of hepadnaviridae as a carrier in medicaments or vaccines.

One of the advantages of such a carrier is that not only the antigen fused or conjugated thereon may be exposed to the immune system, but also an immune response against the capsid protein of a hepadnavirus is induced. Consequently, such a vaccination may lead to the prevention and/or treatment of diseases caused by hepadnaviruses. The virus is preferably of the species of human hepatitis B virus.

Another aspect of the present invention relates to a hypoallergenic molecule derived from Phl p 5 (Genbank Nr. X7435) having a C- and/or N-terminal truncation and lacking substantially IgE-binding capacity.

Grass pollen is one of most potent outdoor seasonal sources of airborne allergens responsible for hay fever and allergic asthma.

More than 40% of allergic individuals display IgE-reactivity with grass pollen allergens, which are divided into more than 11 groups. More than 80% of the grass pollen allergic patients react with group 5 allergens.

Group 5 allergens are non-glycosylated, highly homologous proteins with a molecular mass range from 25-33 kD. Several group 5 allergens have been cloned and/or immunologically characterized.

The trial to reduce the allergenic activity by introducing pointmutations, mutations of several amino acids in row or deletions showed no effect (Schramm G, et al. J Immunol 1999; 162: 2406-1435). IgE-binding regions of Phl p 5 (Flicker S, et al. J Immunol 2000; 165: 3849-3859) have already been described and the three-dimensional structure has been solved (Maglio O, et al. 2002. Protein Eng. 15:635-642).

It turned out that in particular the Phl p 5 peptides according to the present invention, which are C- and/or N-terminally truncated and lack IgE-binding capacity, may be employed for the active vaccination of individuals.

According to a preferred embodiment of the present invention the truncated molecule substantially lacks T-cell epitopes and, thus lacks Phl p 5-specific T-cell reactivity.

As already outlined above, late side effects of allergen immunotherapy can be significantly reduced or even be avoided if the hypoallergenic molecules substantially lack allergen-specific T-cell epitopes.

Truncated Phl p 5 molecules lacking T-cell epitopes are composed of amino acids 93 to 128, 98 to 128, 26 to 53, 26 to 58 or 252 to 283 of Phl p 5 or fragments or sequence variations thereof.

In particular these truncated molecules substantially show low or no allergen-specific T-cell reactivity and are, nevertheless, able to provoke an appropriate immune response directed against the wild-type allergen.

According to another preferred embodiment of the present invention the hypoallergenic truncated Phl p 5 is composed of amino acids 132 to 162, 217 to 246 or 176 to 212 of Phl p 5 or sequence variations thereof.

These hypoallergenic molecules comprise one or more T-cell epitopes but lack IgE-binding capacity.

Another preferred embodiment of the present invention are truncated Phl p 1 molecules lacking T-cell epitopes, which are composed of amino acids 1 to 30, 43 to 70, 87 to 117, 151 to 171 or 214 to 241 of Phl p 1 or sequence variations thereof fused to a viral carrier protein, preferrable the Hep B pre S protein.

Another preferred embodiment of the present invention are truncated Phl p 2 molecules lacking T-cell epitopes, which are composed of amino acids 1 to 33, 8 to 39, 34 to 65 or 66 to 96 of Phl p 2 or sequence variations thereof fused to a viral carrier protein, preferably the Hep B pre S protein.

Another preferred embodiment of the present invention are truncated Phl p 6 molecules lacking T-cell epitopes, which are composed of amino acids 23 to 54, 56 to 90, 73 to 114 or 95 to 127 of Phl p 6 or sequence variants thereof fused to a viral carrier protein, preferably the Hep B pre S protein.

Another preferred embodiment of the present invention refers to truncated Bet v 1 molecules lacking T-cell epitopes, which are composed of amino acids 30 to 59, 50 to 79, 75 to 104, 30 to 74 or 60 to 104 of Bet v 1.

Another preferred embodiment of the present invention are combinations or mixtures of truncated *Phleum pratense* molecules lacking T-cell epitopes, fused to a viral carrier protein, preferably the Hep B pre S protein, as described above.

A preferred embodiment of the present invention are combinations or mixtures of truncated *Phleum pratense* molecules lacking T-cell epitopes, which are composed of one each such fusion protein from truncated Phl p 1, Phl p 2, Phl p 5, and Phl p 6, as described above.

Another aspect of the present invention relates to a hypoallergenic molecule derived from Fel d 1 (Genbank Nr. X62477 and X62478) having a C- and/or N-terminal truncation and lacking IgE-binding capacity.

Allergies to animals affect up to 40% of allergic patients. In the domestic environment, allergies to the most popular pets, cats and dogs, are particularly prevalent and connected with perennial symptoms. Animal allergens are present in dander, epithelium, saliva, serum or urine. Exposure to the allergens can occur either by direct skin contact or by inhalation of particles carrying the allergens. The major cat and dog allergens were shown to be present widespread and could even be detected in non-pet owning households and in public places, e.g., schools. This can be attributed to the high and increasing number of households keeping pets in industrialized countries (about 50%) and the high stability of the allergens, which are carried off and distributed.

Fel d 1 was identified as the major cat allergen, which is recognized by more than 90% of cat allergic patients. Fel d 1 represents a 38 kDa acidic glycoprotein of unknown biological function. It consists of two identical non-covalently linked heterodimers, which, again, are composed of two polypeptide chains antiparallely linked by three disulfide bonds. Chain 1 and chain 2 are encoded on different genes, each consisting of 3 exons. Recombinant Fel d 1 (rFel d 1), expressed as a chain 2- to chain 1 fusion protein, has been generated in *E. coli*. This recombinant Fel d 1 is able to completely mimic the immunological properties of the wild-type allergen.

Peptides derived from the major cat allergen Fel d 1, and lacking IgE-binding capacity are suitable, e.g., for immunotherapy and prophylactic allergy vaccination. The Fel d 1-derived synthetic peptides—like the Phl p 5 and allergen-derived peptides disclosed herein—are capable of inducing an IgG response, i.e., the production of so called "blocking antibodies" or "protective antibodies". These antibodies prevent IgE-binding to the allergen Fel d 1. A significant reduction in allergic symptoms may thus be achieved.

According to a preferred embodiment of the present invention the truncated molecule exhibits reduced T-cell reactivity.

In order to avoid or to significantly reduce late side effects the Fel d 1 derived hypoallergenic molecule exhibits reduced T-cell reactivity as defined in the present invention.

The truncated Fel d 1 is preferably composed of amino acids 1 to 34 or 35 to 70 of chain 1 of Fel d 1, amino acids 1 to 34, 35 to 63 or 64 to 92 of chain 2 of Fel d 1 or sequence variations thereof.

Another aspect of the present invention relates to hypoallergenic molecules being composed of or comprising amino acids 1 to 33, 21 to 51, 42 to 73, 62 to 103 or 98 to 129 of Der p 2, amino acids 1 to 30, 20 to 50, 50 to 80, 90 to 125, 125 to 155 or 165 to 198 of Der p 7, amino acids 1 to 35, 35 to 72, 70 to 100 or 90 to 122 of Der p 21, amino acids 1 to 32, 15 to 48 or 32 to 70, 32 to 60, 52 to 84, 32 to 70 (Cys→Ser) of Der p 23, amino acids 19 to 58, 59 to 95, 91 to 120 or 121 to 157 of Alt a 1, amino acids 31 to 60, 45 to 80, 60 to 96 or 97 to 133 of Par j 2, amino acids 1 to 40, 36 to 66, 63 to 99, 86 to 120 or 107 to 145 of Ole e 1, amino acids 25 to 58, 99 to 133, 154 to 183, 277 to 307, 334 to 363, 373 to 402, 544 to 573, 579 to 608, 58 to 99, 125 to 165, 183 to 224, 224 to 261, 252 to 289, 303 to 340, 416 to 457, 460 to 500 or 501 to 542 of Fel d 2, amino acids 19 to 58, 52 to 91, 82 to 119, 106 to 144 or 139 to 180 of Can f 2, amino acids 19 to 56, 51 to 90, 78 to 118, 106 to 145 or 135-174 of Can f 1, amino acids 27 to 70, 70 to 100 or 92 to 132 of Art v 1, amino acids 31 to 70, 80 to 120, 125 to 155, 160 to 200, 225 to 263, 264 to 300 305 to 350 or 356 to 396 of Amb a 1, amino acids 1 to 34, 35 to 74, 74 to 115, 125 to 165, 174 to 213, 241 to 280, 294 to 333, 361 to 400 or 401 to 438 of Alt a 6, amino acids 1 to 40, 41 to 80, 81 to 120, 121 to 160 of Alt a 2 or fragments or sequence variations thereof.

Methods for the production of fusion proteins are well known in the art and can be found in standard molecular biology references such as Sambrook et al. (Molecular Cloning, 2nd ed., Cold Spring Harbor Laboratory Press, 1989) and Ausubel et al. (Short Protocols in Molecular Biology, 3rd ed; Wiley and Sons, 1995). In general, a fusion protein is produced by first constructing a fusion gene which is inserted into a suitable expression vector, which is, in turn, used to transfect a suitable hosT-cell. In general, recombinant fusion constructs are produced by a series of restriction enzyme digestions and ligation reactions which result in the desired sequences being incorporated into a plasmid. If suitable restriction sites are not available, synthetic oligonucleotide adapters or linkers can be used as is known by those skilled in the art and described in the references cited above. The polynucleotide sequences encoding allergens and native proteins can be assembled prior to insertion into a suitable vector or the sequence encoding the allergen can be inserted adjacent to a sequence encoding a native sequence already present in a vector. Insertion of the sequence within the vector should be in frame so that the sequence can be transcribed into a protein.

It will be apparent to those of ordinary skill in the art that the precise restriction enzymes, linkers and/or adaptors required as well as the precise reaction conditions will vary with the sequences and cloning vectors used. The assembly of DNA constructs, however, is routine in the art and can be readily accomplished by a person skilled in the art.

It is a specific and unexpected advantage, that the fusion proteins derived from truncated hypoallergenic allergen molecules and the human hepatitis B pre S protein can be reproducibly expressed in standard expression systems and easily be manufactured produced in high yield with processes and reproducibly in standard expression systems known to a person skilled in the art, most particularly by using in an *Escherichia coli* as expression system. Such manufacturing process typically comprise the expression of the molecules according to the invention by the cultivation of cells in a bioreactor (e.g. in a fermenter, shake flask), followed by cell harvest (e.g. by filtration, centrifugation, etc.) and cell disruption (e.g. by high-pressure homogenization, sonication, freeze/thaw cycles, enzymatic or chemical cell lysis, etc.), purification of the molecules (e.g. by chromatography, filtration, precipitation, ultra/diafiltration, etc.) and final product formulation. In order to obtain a high yield of the molecules according to the invention, preferably high-cell density cultivation processes are employed, by application of fed-batch fermentation.

Another aspect of the present invention relates to a nucleic acid molecule coding for a hypoallergenic molecule and a fusion protein according to the present invention.

The nucleic acid molecule of the present invention may be employed, e.g., for producing said molecules recombinantly.

Said nucleic acid molecule may—according to another aspect of the present invention—be comprised in a vector.

This vector is preferably an expression vector.

The present invention is further illustrated by the following figures and examples, however, without being restricted thereto.

FIG. 2 A shows the primary sequence of fusion protein HBV_PhlP1_4xP5 (BM321, sequence ID Nr. 14)

FIG. 2 B shows the primary sequence of fusion protein HBV_Phlp2_4xP3 (BM322, sequence ID Nr. 15)

FIG. 2 C shows the primary sequence of fusion protein HBV_Phlp5_V2 (BM325, sequence ID Nr. 16)

FIG. 2 D shows the primary sequence of fusion protein HBV_Phlp6_4xP1 (B326, sequence ID Nr. 17)

FIG. 2 E shows the primary sequence of fusion protein HBV_Betv1_4PA (BM31a, sequence ID Nr. 18)

FIG. 2 F shows the primary sequence of fusion protein HBV_Betv1_2PA2PB (BM31, sequence ID Nr. 19)

FIG. 2 G shows the primary sequence of fusion protein HBV_Phlp5_V1 (sequence ID No. 20)

Figure 1A:
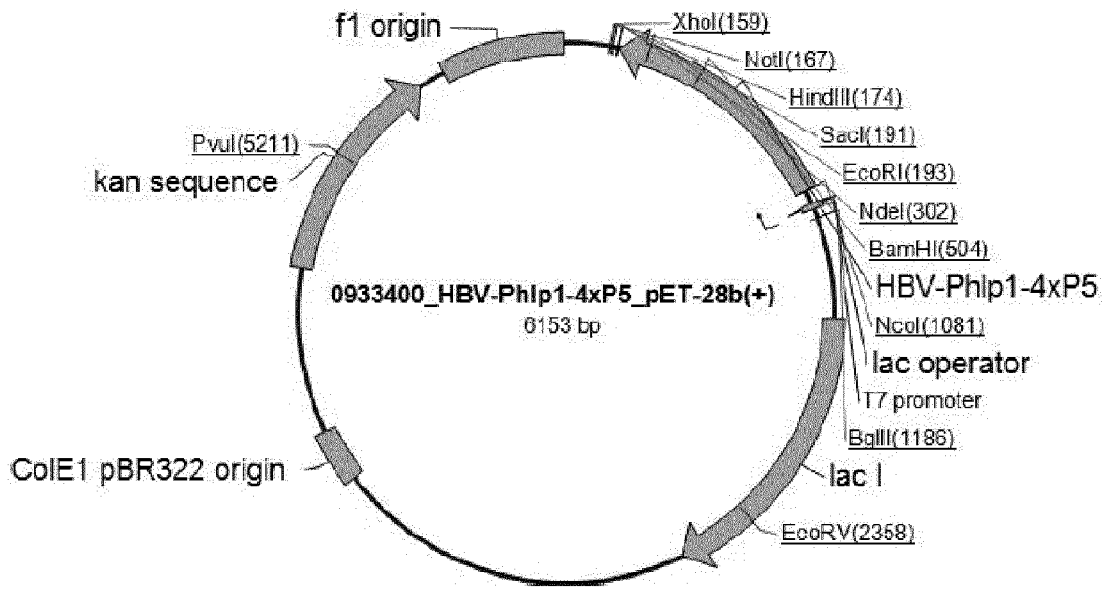
FIG. 1A shows a schematic overview of vector HBV_Phlp1_4xP5
Figure 1B:
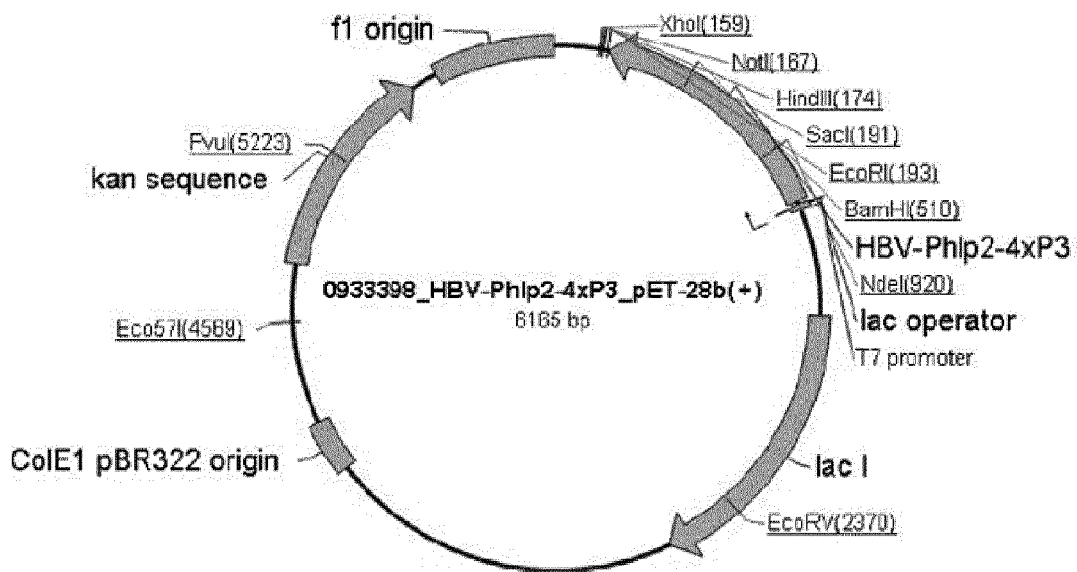
FIG. 1B shows a schematic overview of vector HBV_Phlp2_4xP3
Figure 1:
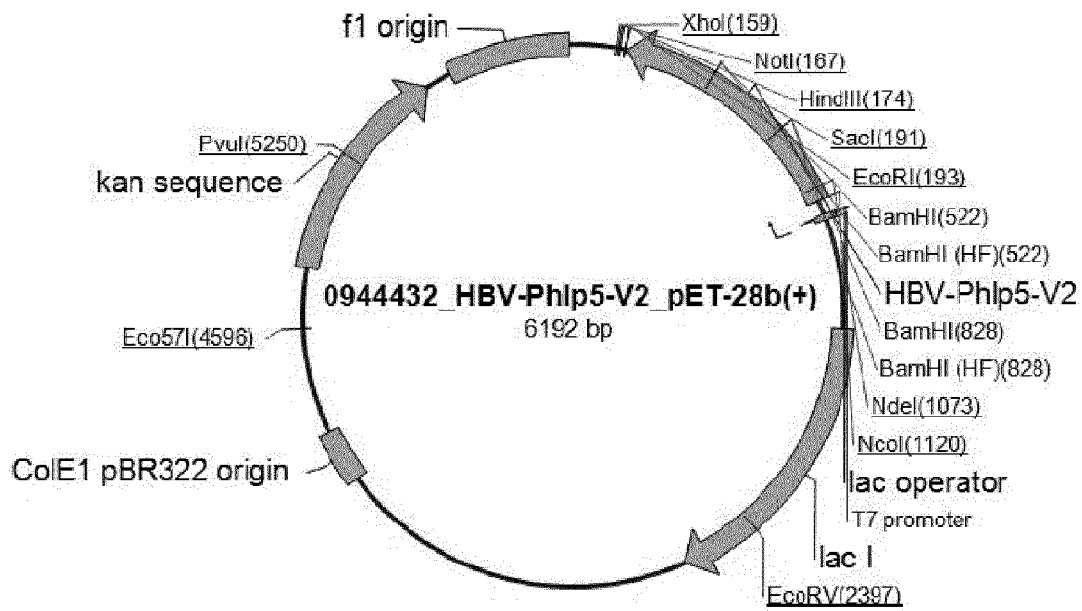
FIG. 1C shows a schematic overview of vector HBV_Phlp5_V2
FIG. 1D shows a schematic overview of vector HBV_Phlp6_4xP1
Figure 1:
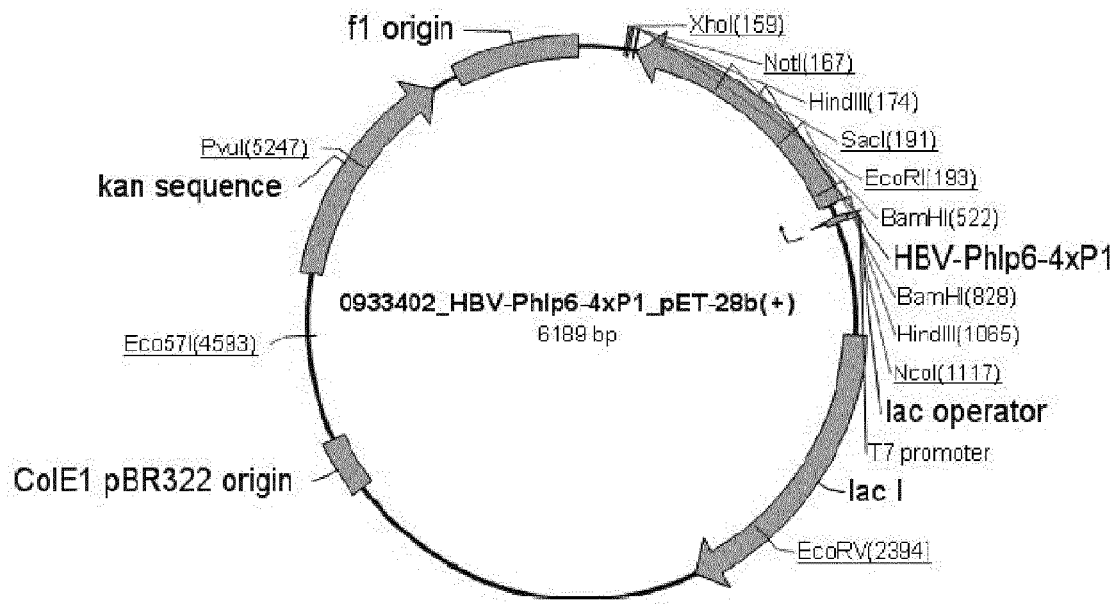
Figure 3:
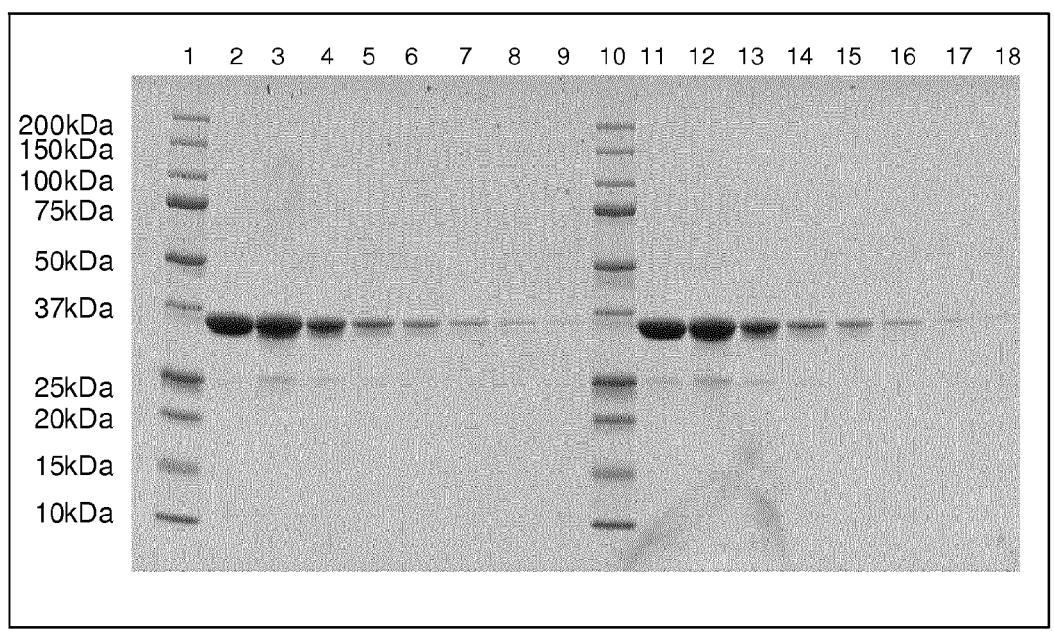
Figure 3:
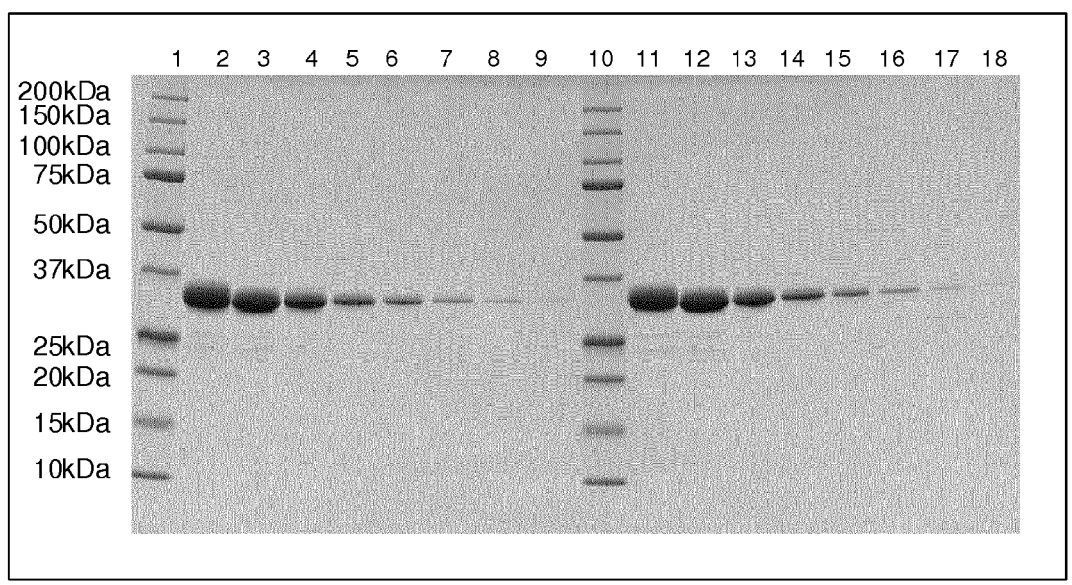

FIG. 3 A shows a Coomassie Blue stained 12% SDS Page gel containing purified fusion protein HBV_Phlp1_4xP5 (BM 321, lane 1 and 10: 5 ug molecular marker, lane 2, 3, 11 and 12 5 ug BM321, lane 4 and 13 2 ug BM321, lane 5 and 14 1 ug BM321, lane 6 and 15 0.5 ug BM321, lane 7 and 16 0.25 ug BM321, lane 8 and 17 0.1 ug BM 321, lane 9 and 18 0.05 ug BM321). Lanes 1 to 9 are under reducing and lanes 10-18 under non-reducing conditions.

FIG. 3 B shows a Coomassie Blue stained 12% SDS Page gel containing purified fusion protein HBV_Phlp2_4xP3 (BM 322, lane 1 and 10: 5 ug molecular marker, lane 2, 3, 11 and 12 5 ug BM322, lane 4 and 13 2 ug BM322, lane 5 and 14 1 ug BM322, lane 6 and 15 0.5 ug BM322, lane 7 and 16 0.25 ug BM322, lane 8 and 17 0.1 ug BM 322, lane 9 and 18 0.05 ug BM322). Lanes 1 to 9 are under reducing and lanes 10-18 under non-reducing conditions.

FIG. 3 C shows a Coomassie Blue stained 12% SDS Page gel containing purified fusion protein HBV_Phlp5_V2 (BM 325, lane 1 and 10: 5 ug molecular marker, lane 2, 3, 11 and 12 5 ug BM325, lane 4 and 13 2 ug BM325, lane 5 and 14 1 ug BM325, lane 6 and 15 0.5 ug BM325, lane 7 and 16 0.25 ug BM325, lane 8 and 17 0.1 ug BM 325, lane 9 and 18 0.05 ug BM325). Lanes 1 to 9 are under reducing and lanes 10-18 under non-reducing conditions.

FIG. 3 D shows a Coomassie Blue stained 12% SDS Page gel containing purified fusion protein HBV_Phlp6_4xP1 (BM 326, lane 1 and 10: 5 ug molecular marker, lane 2, 3, 11 and 12 5 ug BM326, lane 4 and 13 2 ug BM326, lane 5 and 14 1 ug BM326, lane 6 and 15 0.5 ug BM326, lane 7 and 16 0.25 ug BM326, lane 8 and 17 0.1 ug BM 326, lane 9 and 18 0.05 ug BM326). Lanes 1 to 9 are under reducing and lanes 10-18 under non-reducing conditions.

Figure 4:
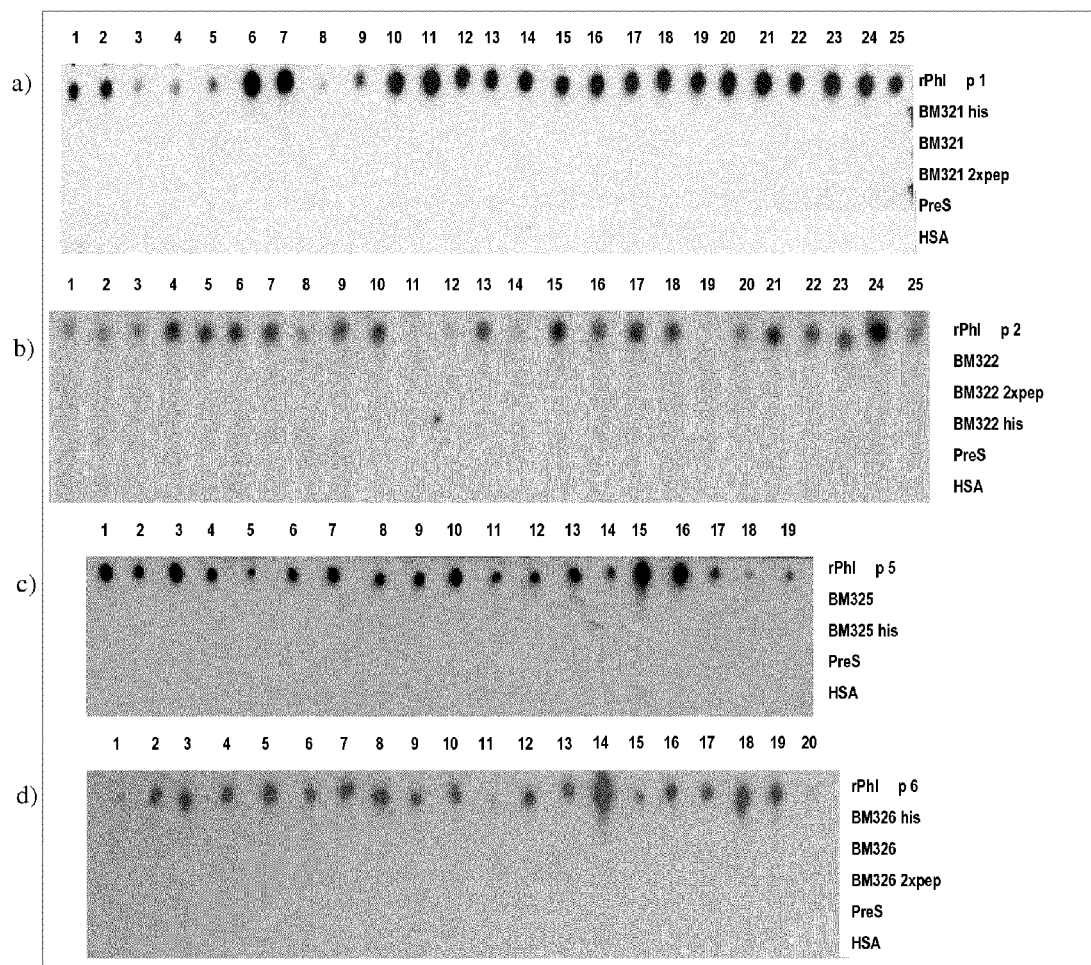

FIG. 4 demonstrates the lack of IgE reactivity of fusion peptides derived from grass pollen allergens. IgE binding of fusion proteins in comparison to the complete allergen was tested by IgE dot-blot assay. Sera from the indicated number of grass pollen allergic patients were incubated with dotted proteins and bound IgE was detected with 125I-labelled anti-human IgE. No IgE binding was detected for any of the four peptide-carrier fusion proteins. a) shows the results from the dot blot assay using HBV_Phlp1_4xP5 (BM321); b) shows the results from the dot blot assay using HBV_Phlp2_4xP3 (BM322); c) shows the results from the blot assay using HBV_Phlp5_V2 (BM325); d) shows the results from form the dot blot assay using HBV_Phlp6_4xP1 (BM326).

Figure 5:
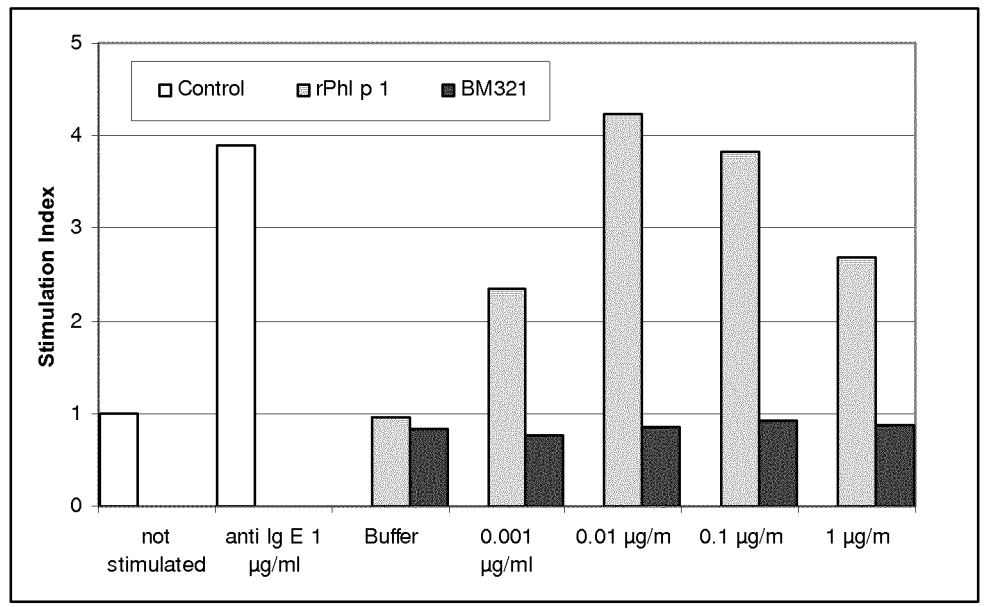

FIG. 5 shows the low allergenic activity of grass pollen allergen derived fusion protein HBV_Phlp1_4xP5 (BM321) as determined by CD203c expression on basophils of allergic patients. PBMCs from grass pollen allergic patients were incubated with serial dilutions of Phl p 1 (light grey bars) or BM321 (dark grey bars). Induction of CD203c was measured as mean florescense intensities, and calculated stimulation indices are shown on the y-axis.

Figure 6:
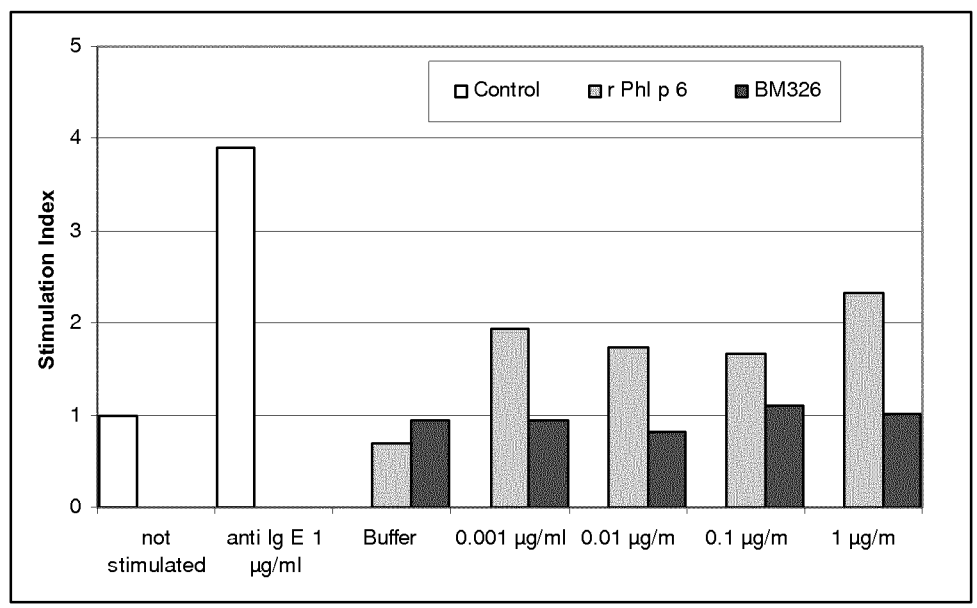
Figure 7A:
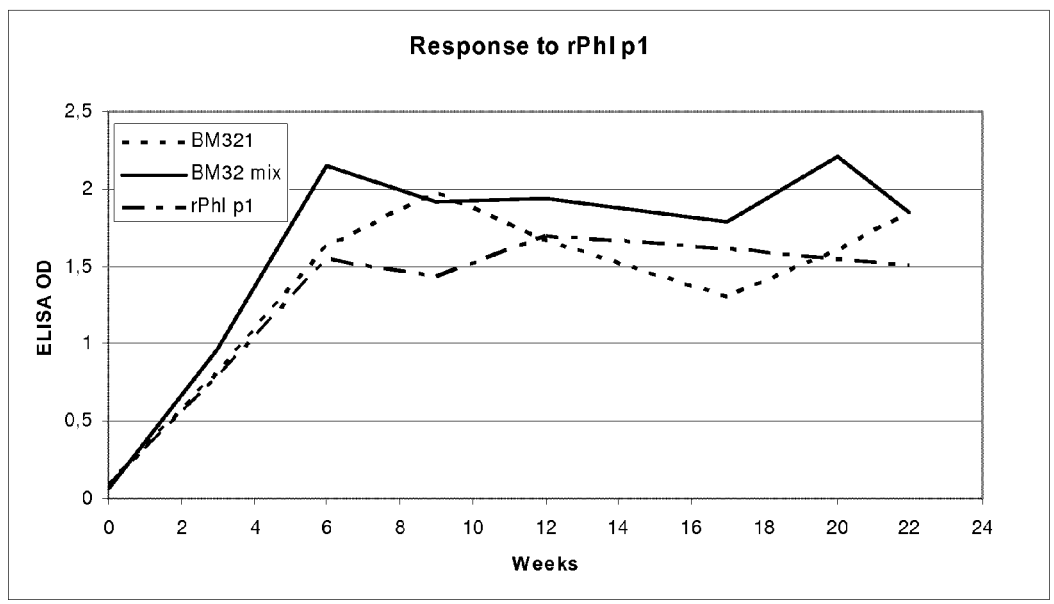
Figure 7B:
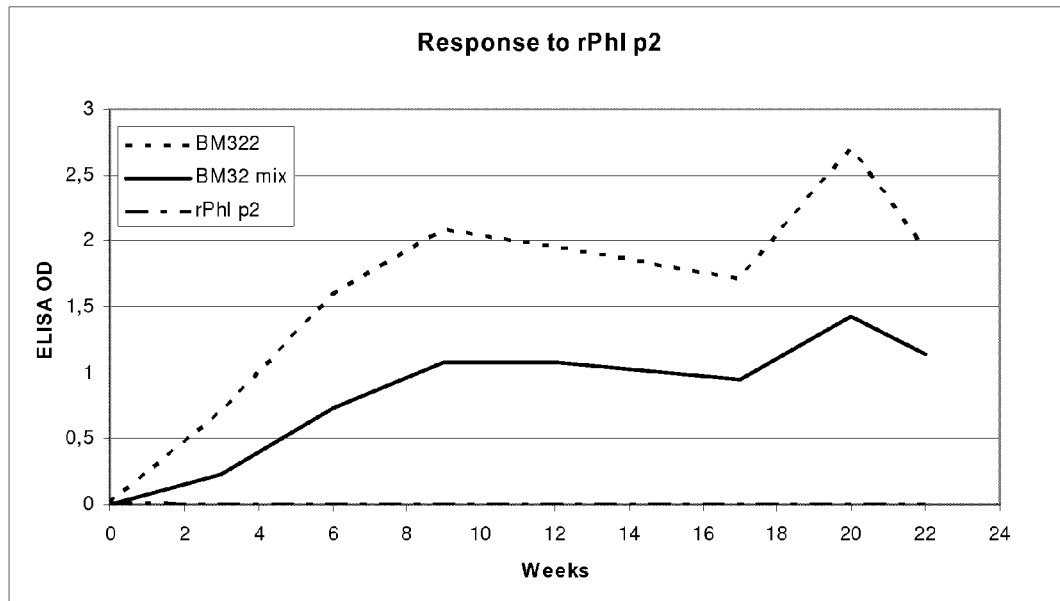
Figure 7C:
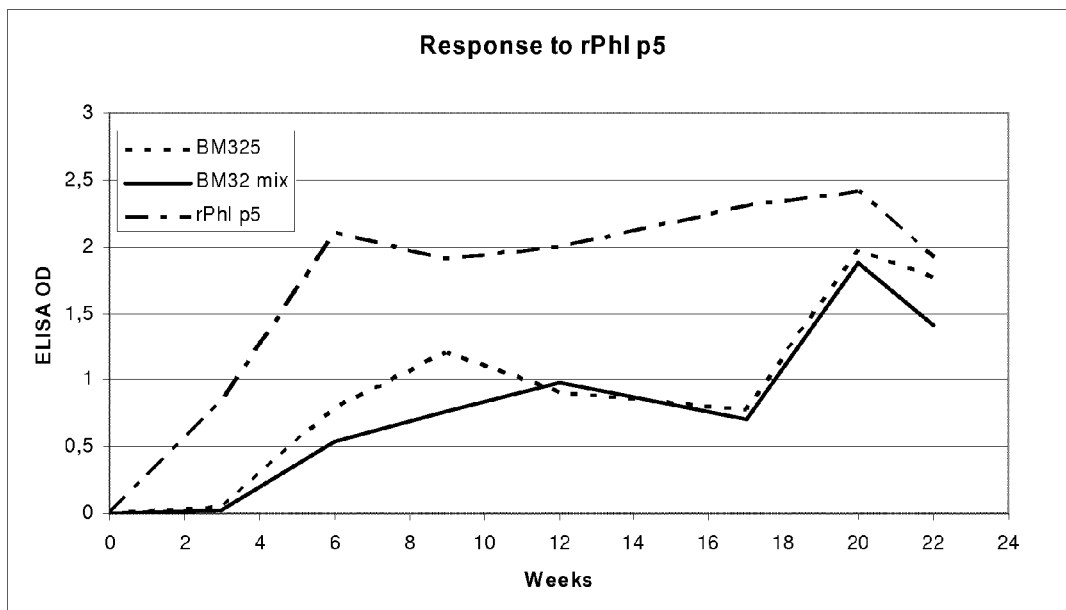
Figure 7D:
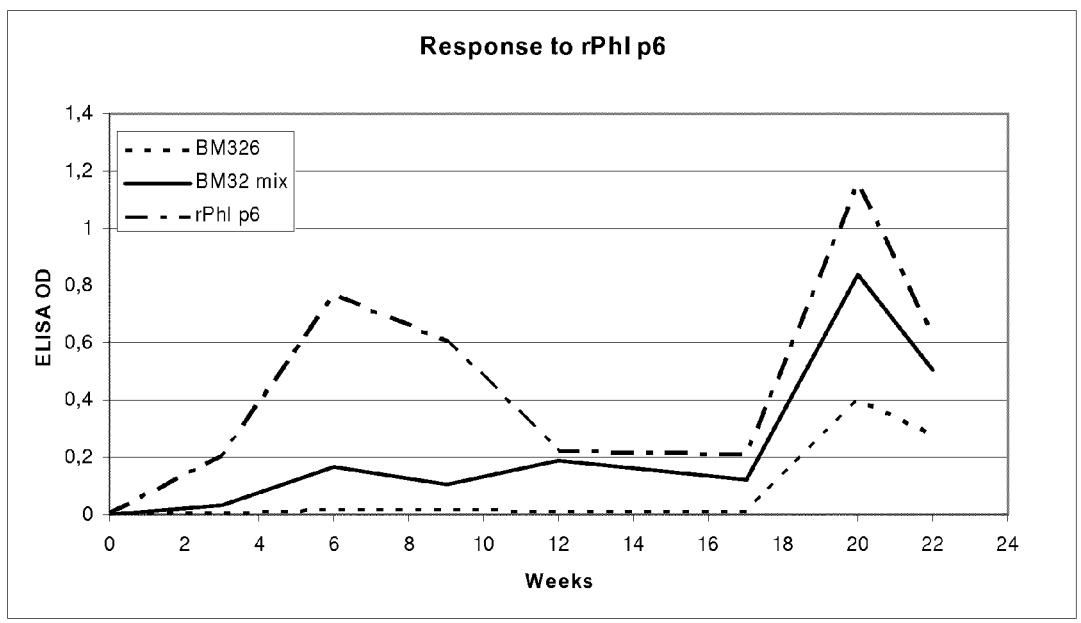

FIG. 6 shows the low allergenic activity of grass pollen allergen derived fusion protein HBV_Phlp6_4xP1 (BM326) as determined by CD203c expression on basophils of allergic patients. PBMCs from grass pollen allergic patients were incubated with serial dilutions of Phl p 6 (light grey bars) or BM326 (dark grey bars). Induction of CD203c was measured as mean florescense intensities, and calculated stimulation indices are shown on the y-axis.

FIG. 7 shows Timothy grass pollen allergen-specific IgG1 responses in mice. Groups of 4 mice were immunized with 20 ug of fusion proteins (single fusion proteins and combination of 4 fusion proteins) and 10 µg each (Phl p1 and 5) or 5 µg each (Phl p2 and 6) of wild-type allergen at study week 0 and 3 followed by a boost immunization at study week 17. Antigens were administered subcutaneously in the back region of the animals. Blood was collected at study week 0, 3, 6, 9, 12, 17, 20 and 22 from the tail vein of the mice. In study weeks with immunizations blood was collected one day before the immunization. Immune sera of mice were investigated for the presence of allergen-specific IgG1 by ELISA. Pre-Immune sera before the first immunization were negative in all animals. Individual fusion proteins were compared to the application of a mixture of fusion proteins.

a) Immune response against rPhl p 1 antigen for HBV_Phlp1_4xP5 (BM321 as single component), BM321 in a mixture with BM322, BM325 and BM326, and rPhl p 1 immunized mice.
b) Immune response against rPhl p 2 antigen for HBV_Phlp2_4xP3 (BM321 as single component), BM322 in a mixture with BM321, BM325 and BM326, and rPhl p 2 immunized mice.
c) Immune response against rPhl p 5 antigen for HBV_Phlp5_V2 (BM325 as single component), BM325 in a mixture with BM321, BM322 and BM326, and rPhl p 5 immunized mice.
d) Immune response against rPhl p 6 antigen for HBV_Phlp6_4xP1 (BM326 as single component), BM326 in a mixture with BM321, BM322 and BM325, and rPhl p 6 immunized mice.

Figure 8:
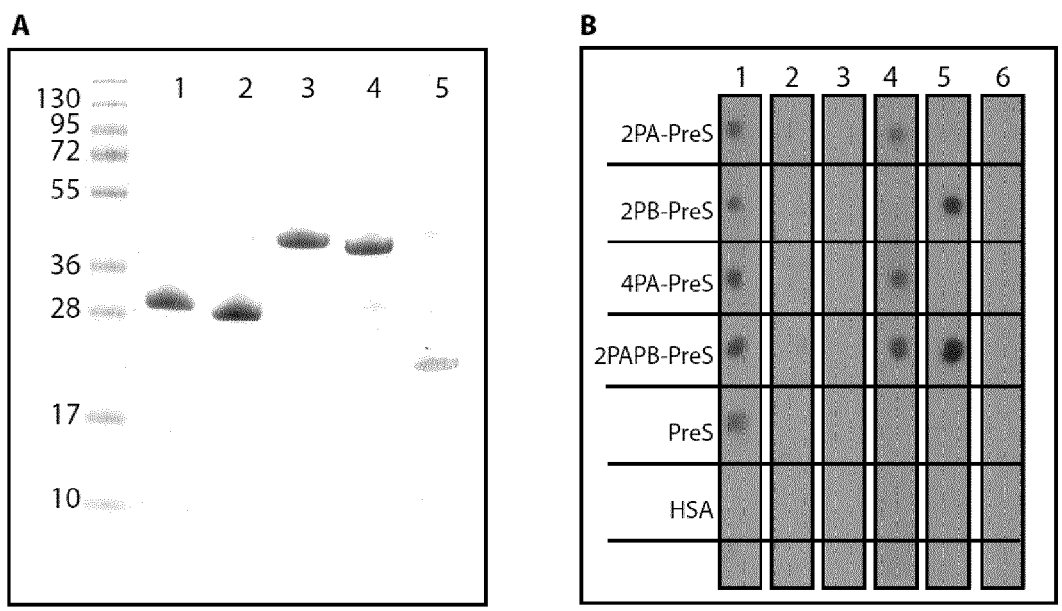

FIG. 8 shows the molecular and immunological characterization of recombinant fusion proteins. A. Coomassie-stained SDS-PAGE showing four PreS fusion proteins with Bet v1 derived peptides (lane 1: 2xPA-PreS, lane 2: 2xPB-PreS, lane 3: 4xPA-PreS, lane 4: 2xPA2xPB-PreS) and the carrier PreS (lane 5). B. Nitrocellulose dotted recombinant fusion proteins and PreS are probed with a rabbit anti-PreS serum (lane 1), rabbit preimmune-serum (lane 3) buffer control for rabbit antibodies (lane 3) and monoclonal antibodies directed against Bet v 1-derived peptide P2' (mAb2) (lane 4) and P4' (mAb12) (lane 5) and buffer control for monoclonal mouse antibodies (lane 6).

Figure 9A:
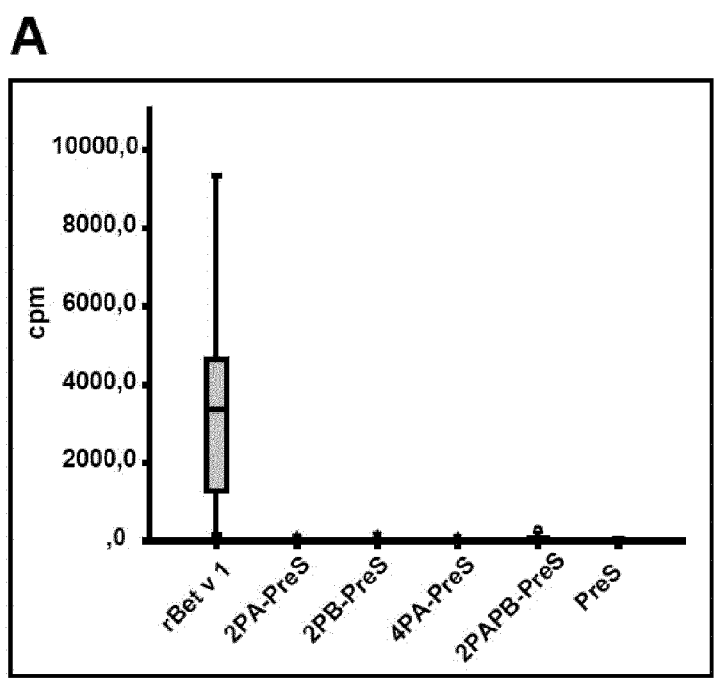

FIG. 9 A shows IgE reactivity of rBet v 1 and recombinant fusion proteins of PreS with Bet v 1 derived peptides. Sera from birch pollen allergic patients, from non-allergic controls and only buffer were tested for their reactivity to dot-blotted rBet v 1, the four recombinant fusion proteins (2PA-PreS, 2PB-PreS, 4PA-PreS, 2PA2PB-PreS) and PreS alone. Bound human IgE was detected with 125I-labeled anti-human IgE antibodies. Counts per minute (cpm) corresponding to bound IgE are measured with a γ-counter and indicated at Y-axis. Box plots show the results of 50 birch pollen allergic patients.

Figure 9B:
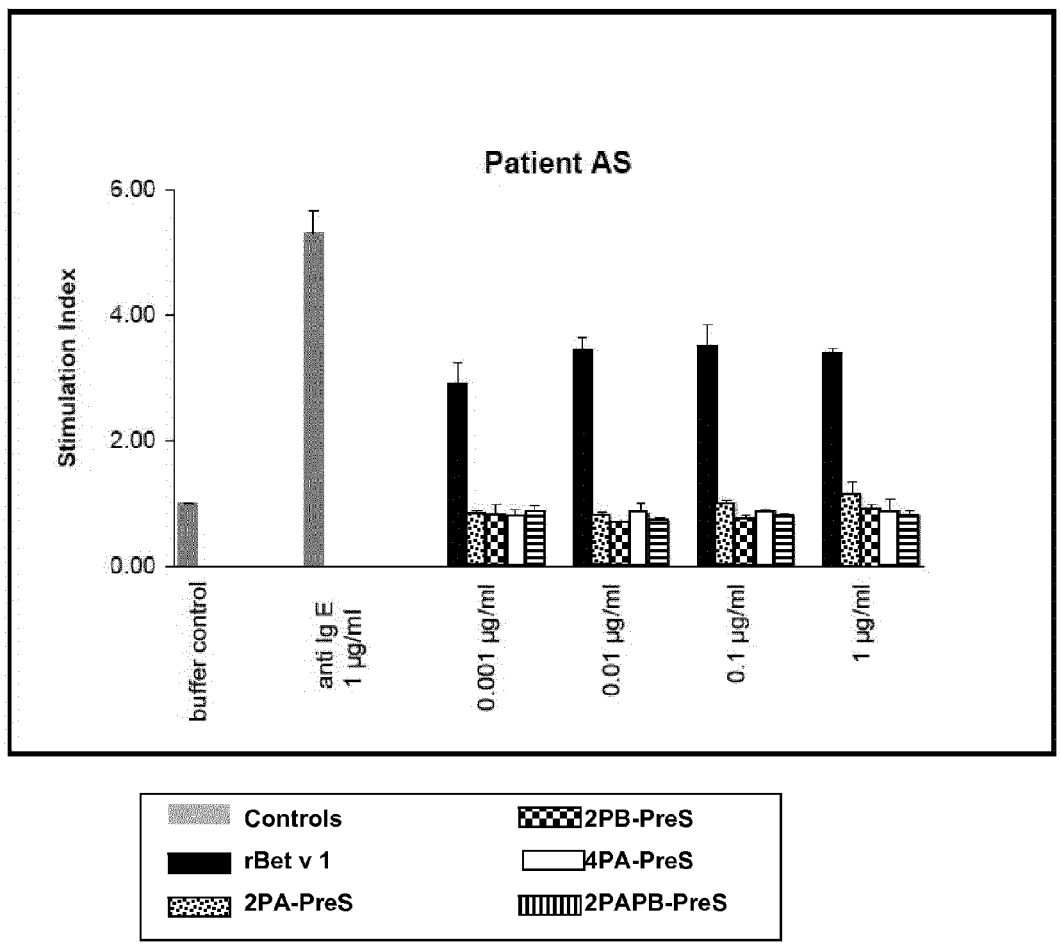

FIG. 9B shows the basophil activation by rBet v1 and the four PreS fusion proteins as measured by CD 203c upregulation. Blood samples of birch pollen allergic patients were exposed to increasing concentrations (0.001-1 µg/ml) of antigens, anti-IgE of buffer control (Co). Results of one representative patient are shown. CD 203c expression was determined by FACS analysis and is displayed as stimulation index (SI (y-axis). Means of triplicate measurements are shown and standard deviations are indicated.

Figure 10:
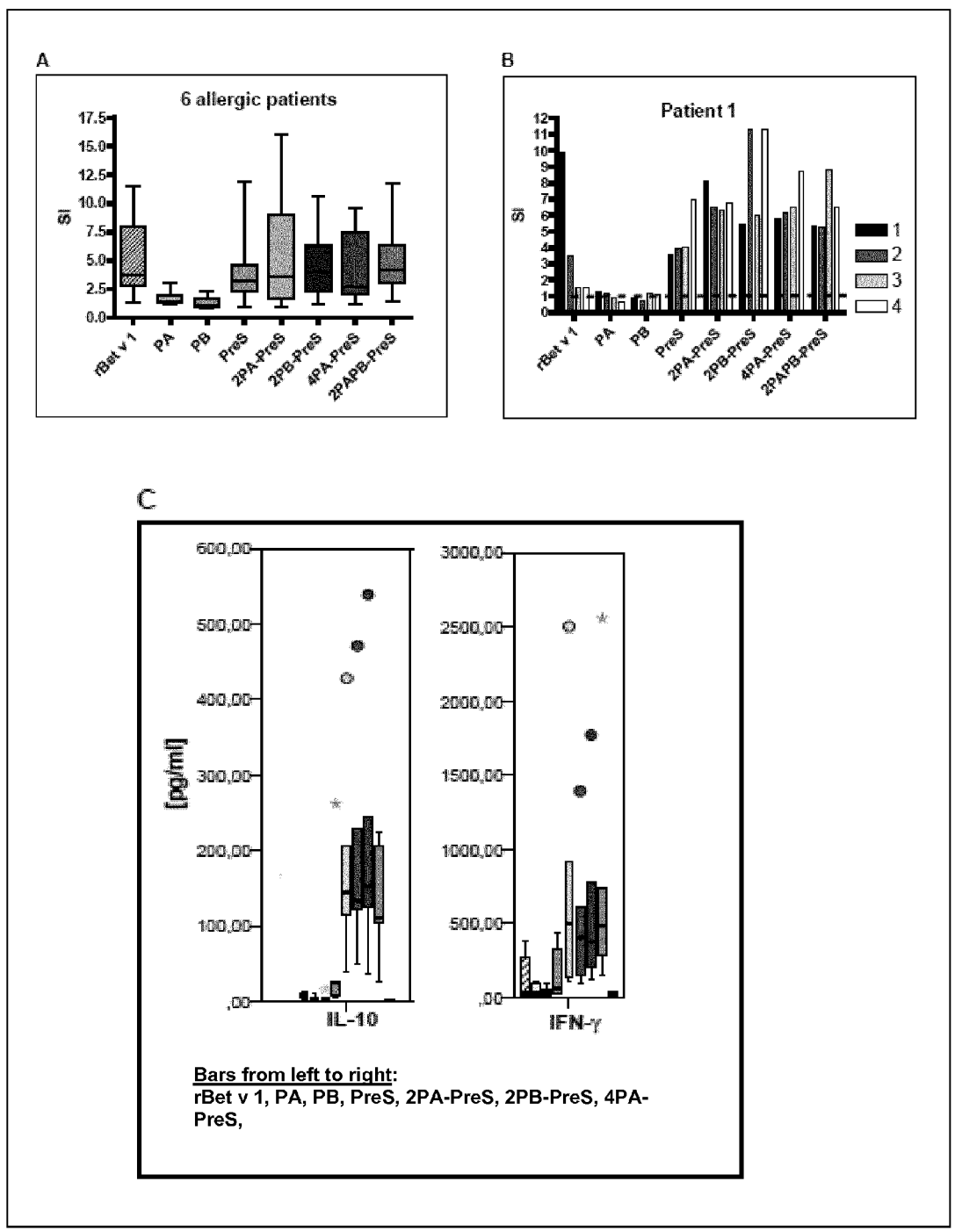
Figure 11A:
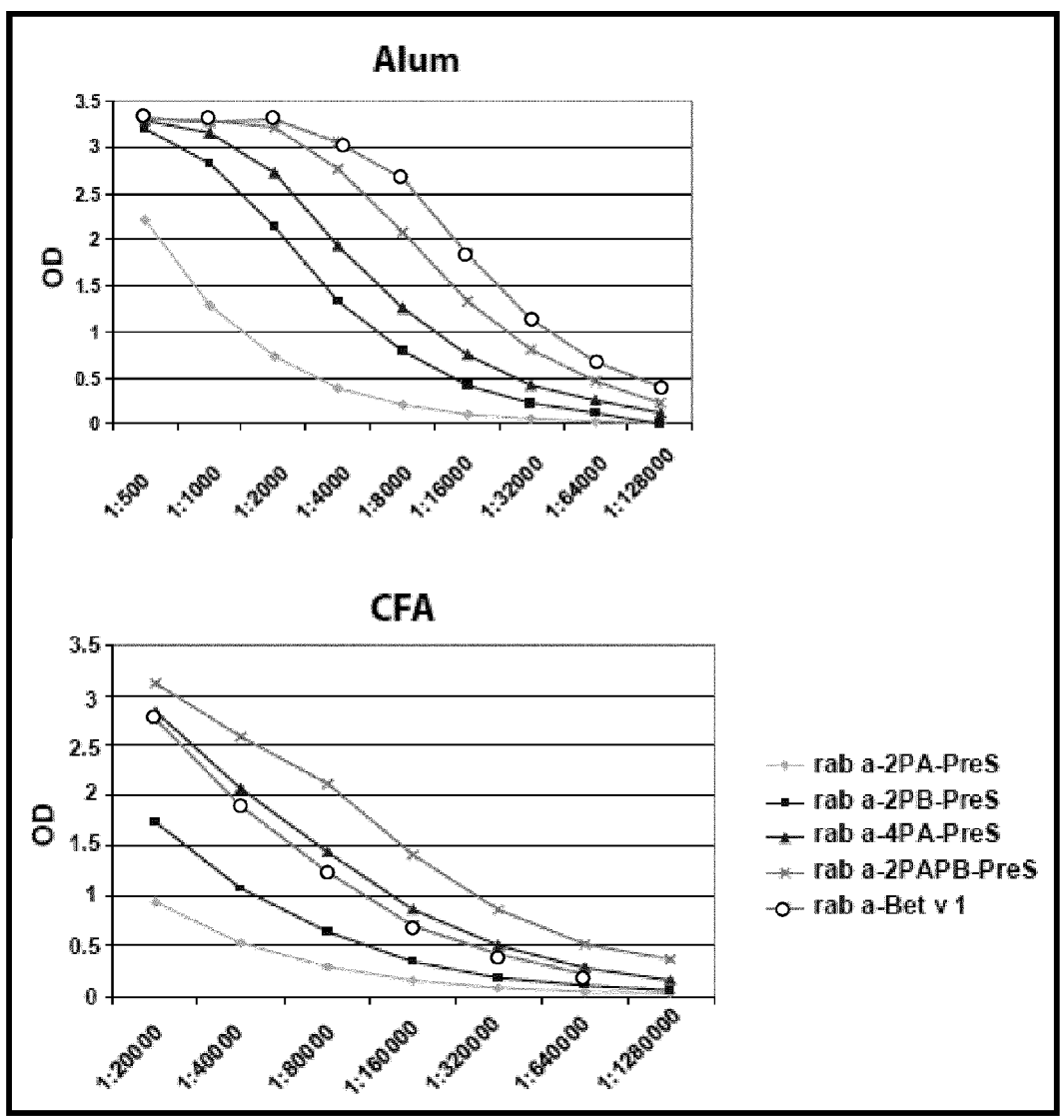
Figure 11B:
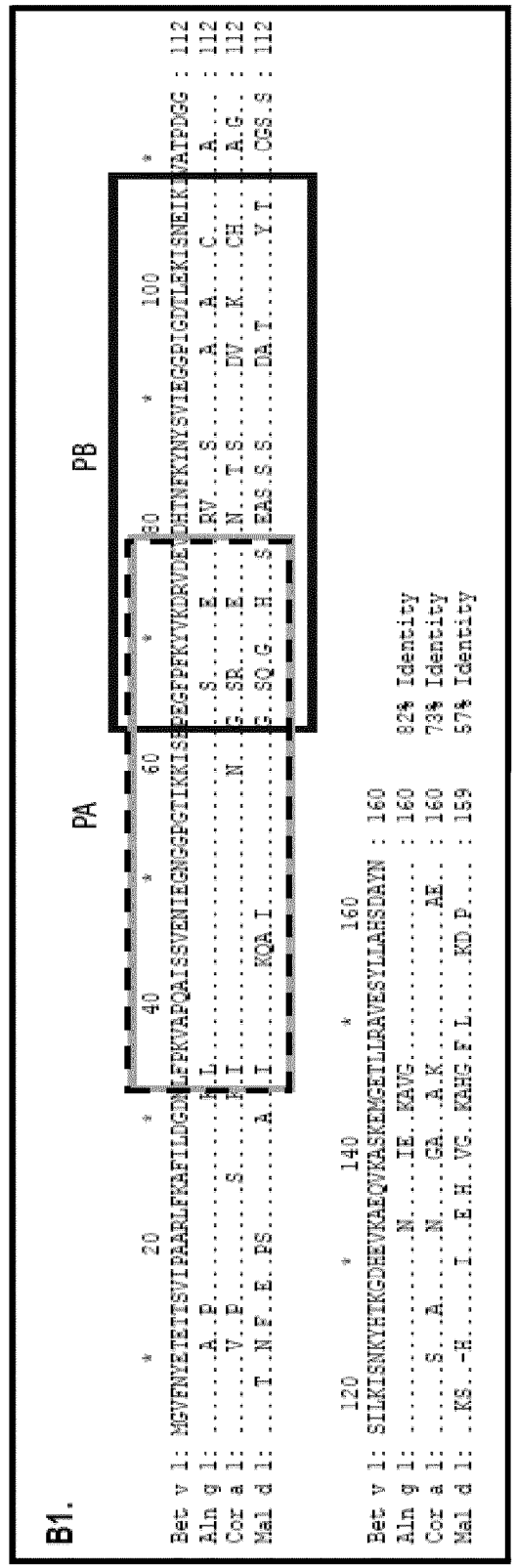
Figure 11B:
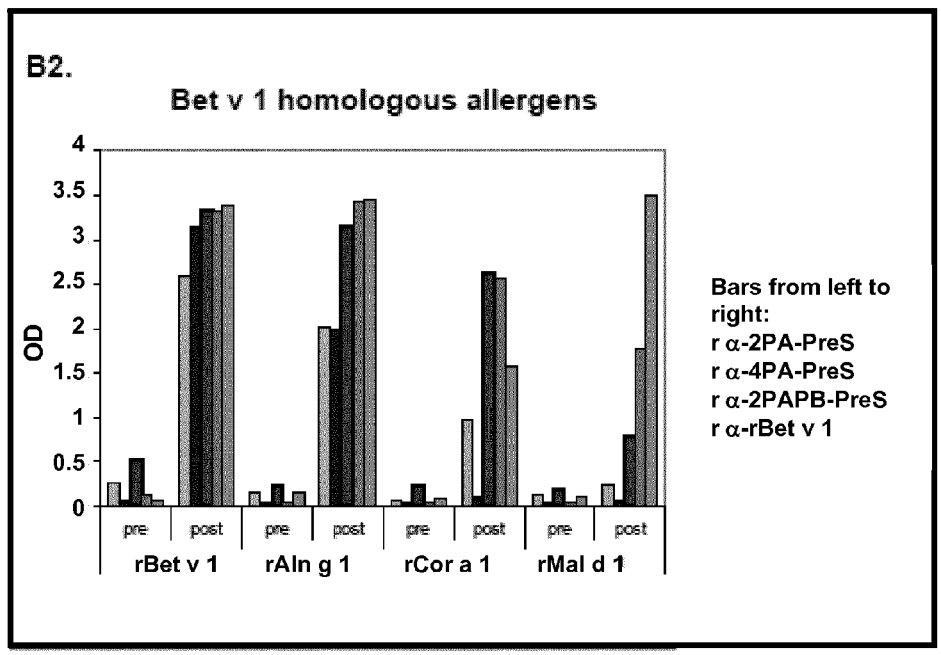
Figure 11C:
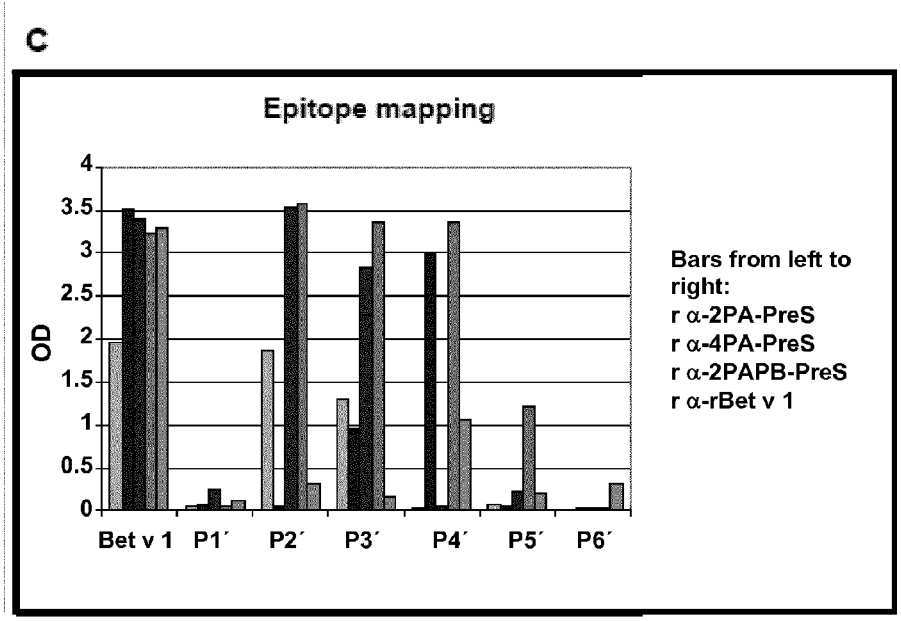

FIG. 10 shows lymphoproliferative responses and cytikine production of PBMC of birch pollen allergic patients. PBMCs of birch pollen allergic patients have been stimulated with equimolar amounts of rBet v 1, the Bet v 1 derived peptides PA and PB, PreS alone, and PreS fusion proteins (i.e. 2PA-PreS, 2PB-PreS, 4PA-PreS, 2PAPB-PreS). Stimulation indices (SI) (y-axes) are displayed.

(A) SI for the highest concentration (5 µg/well of Bet v 1 and equimolar amounts of the peptides, PreS and PreS fusion proteins) of 6 birch pollen allergic patients are shown as box blots, where 50% of the values are within the boxes and non-outliers are between the bars. The lines within the boxes indicate the median values.

(B) SI for four concentrations (1=5 µg/well, 2=2.5 µg/well, 3=1.25 µg/ml, 4=0.63 µg/well of rBet v1 and equimolar amounts of the peptides, PreS and PreS fusion proteins) are shown for one representative patient.

(C) Cytokine production in supernatants of PBMCs of 6 birch pollen allergic patients, stimulated with 2.5 μg/mL of rBet v 1 and equimolar amounts of peptides PA and PB, PreS and four PreS fusion proteins, have been measured. Observed concentrations (pg/mL) (y-axes) after stimulation with antigens are shown in box blots, where 50% of the values are within the boxes and non-outliers are between the bars. The lines within the boxes indicate the median values.

FIG. 11 shows the induction of IgG antibodies specific for rBet v 1 and Bet v 1 homologous allergens after subcutaneous immunization by PreS fusion proteins in rabbits.
(A) Rabbits have been immunized with Alumhydroxide-adsorbed (Alum) (top) or complete Freund's adjuvant (CFA)-adsorbed (bottom) fusion proteins (2PA-PreS, 2PB-PreS, 4PA-PreS, 2PAPB-PreS) and rBet v 1. Rabbit IgG specific for rBet v 1 has been measured and mean optical density (OD) values for duplicate measurements are displayed (y-axes) for different dilutions of rabbit anti-sera (x-axes).
(B1) Multiple sequence alignment of Bet v 1 and Bet v 1-homologous allergens in alder (Aln g 1), hazel (Cor a 1) and apple (Mal d 1). Same amino acids are indicated as dots, gaps are indicated as dashes. Percentage identity of Bet v 1 homologous allergens to Bet v 1 is shown at the right side. Bet v 1-derived peptide A (PA, dashed line) and peptide B (PB, full line) are framed.
(B2) IgG antibodies of anti-rabbit sera (rab α-2PA-PreS, rab α-2PB-PreS, rab α-4PA-PreS, rab α-2PAPB-PreS) directed against rBet v 1, rAln g 1, rCor a 1 and rMal d 1 (x-axis) have been measured by ELISA. Means of duplicate measurements are shown. Optical density (OD) corresponding to allergen-specific IgG in rabbit sera (post) is displayed in comparison with corresponding preimmune sera (pre) (y-axes).
(C) IgG antibodies of rabbit immunized with rBet v 1 and recombinant fusion proteins (2PA-PreS, 2PB-PreS, 4PA-PreS, 2PAPB-PreS) directed against six Bet v 1-derived peptides (P1'-P6') (x-axis) have been measured by ELISA. Means of optical density (OD) values for duplicate measurements (y-axis) are displayed.

Figure 12:
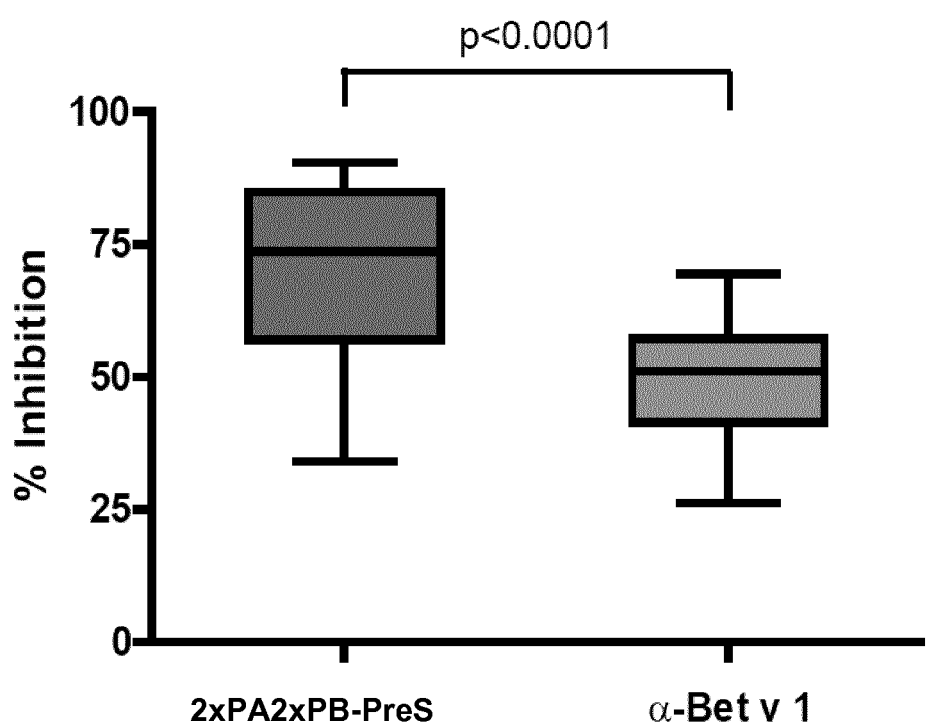

FIG. 12 shows the inhibition of Anti-2xPA2xPB-PreS rabbit serum against allergic patients' IgE compared to rabbit serum against complete rBet v 1. The percentage inhibition of IgE binding to rBet v 1 (y-axes) obtained with anti-2xPA2xPB-PreS and anti-rBet v 1 rabbit sera were determined by means of inhibition ELISA and are displayed as box blots, where 50% of the values are within the boxes and nonoutliers are between the bars. The lines within the boxes indicate the median values. Results of 21 birch pollen allergic patients are shown.

Figure 13:
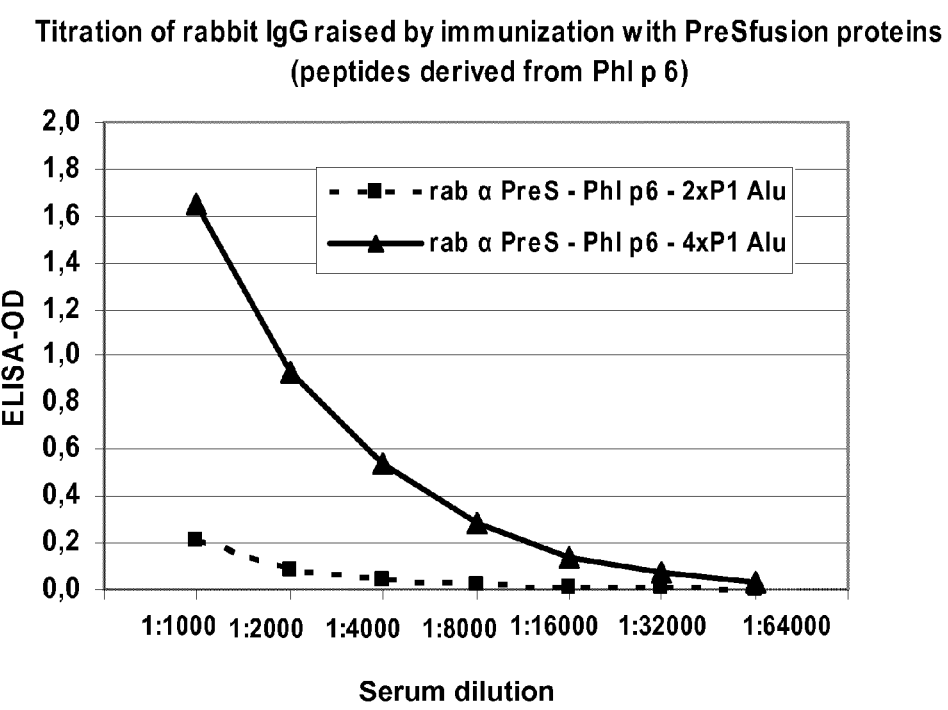
Figure 14A:
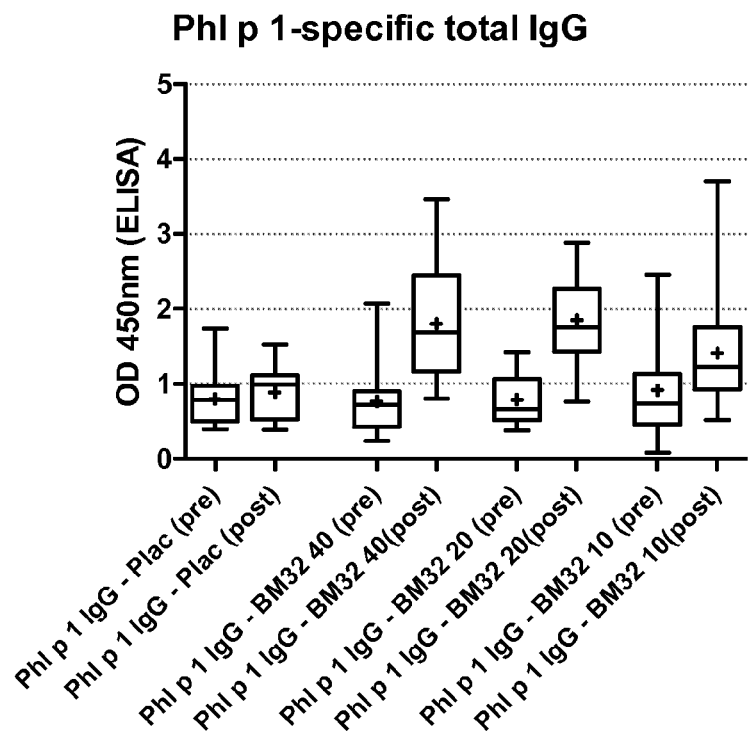
Figure 14B:
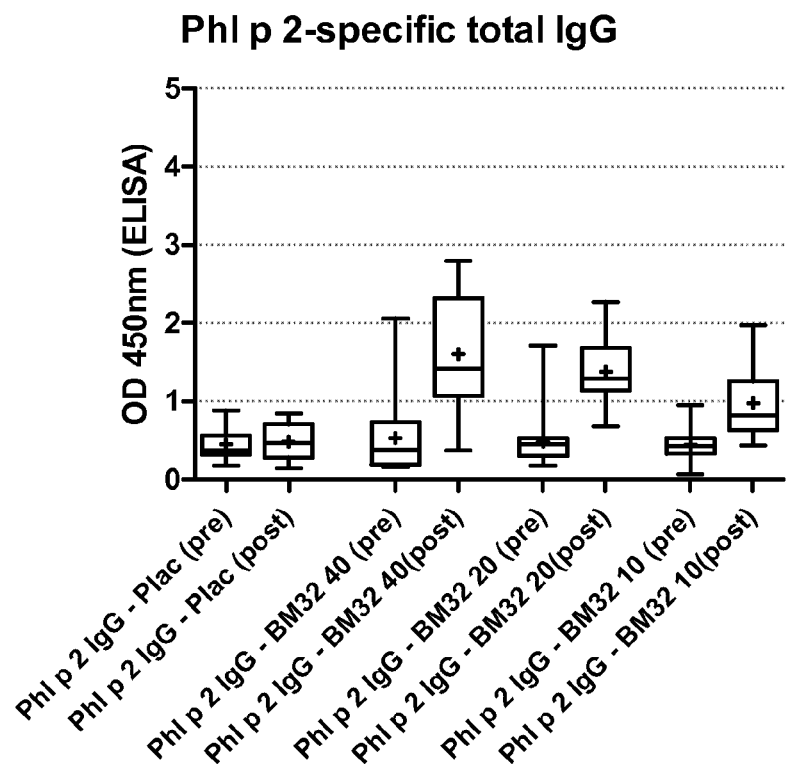
Figure 14C:
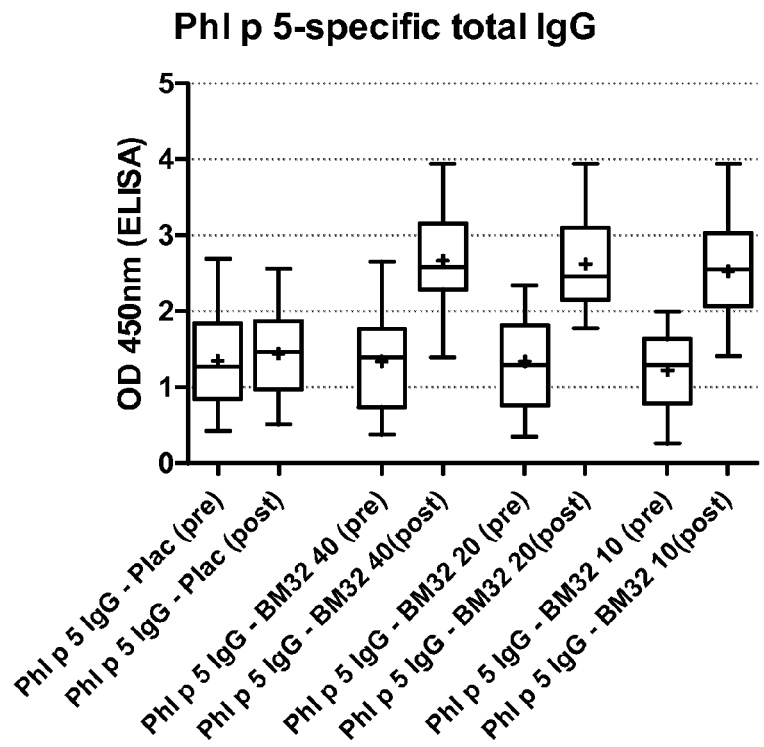
Figure 14D:
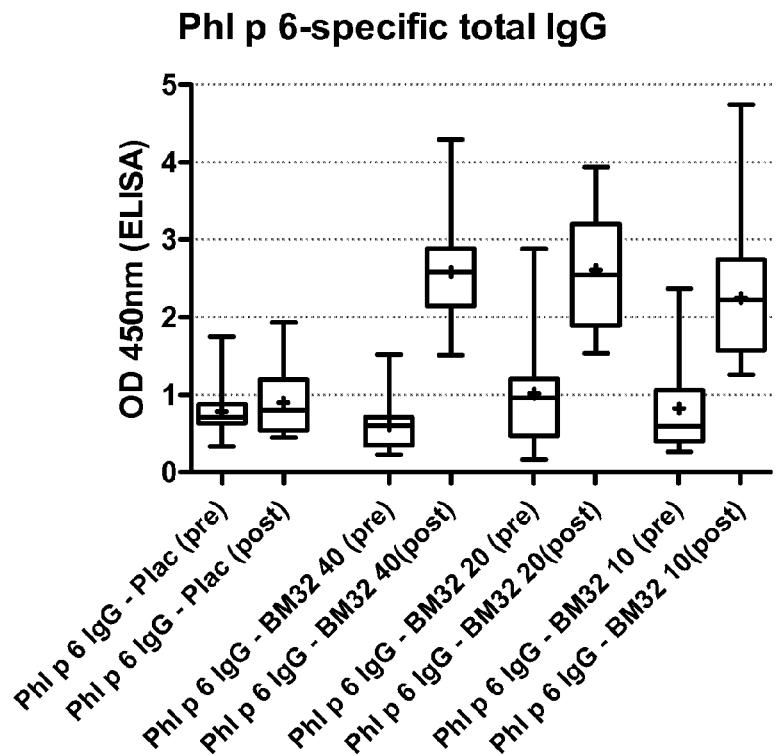

FIG. 13 shows a titration of rabbit IgG raised after immunisation with PreS-fusion proteins containing either 2 or 4 copies of a Phl p 6 derived peptide. For the immunogenicity testing rabbits (New Zealand White rabbits) were immunized with the different fusion proteins using aluminium hydroxide as adjuvant. The induction of specific antibodies was monitored in ELISA assays. Results show that the fusion proteins containing 4 peptides are more immunogenic than the fusion proteins containing 2 peptides.

FIG. 14 shows the induction of a robust IgG response directed to the grass pollen allergens Phl p 1 (A), Phl p2 (B), Phl p 5 (C), and Phl p 6 (D) following in human grass pollen allergics following subcutaneous immunization with a vaccine formulation (BM32) comprising a mixture of the 4 hypoallergenic fusion proteins with SEQ ID No. 14, SEQ ID No. 15, SEQ ID No. 16, and SEQ ID NO. 17. The determination of IgG was carried out by ELISA. IgG levels before treatment (pre) are compared to IgG levels post-treatment (post).

Figure 15:
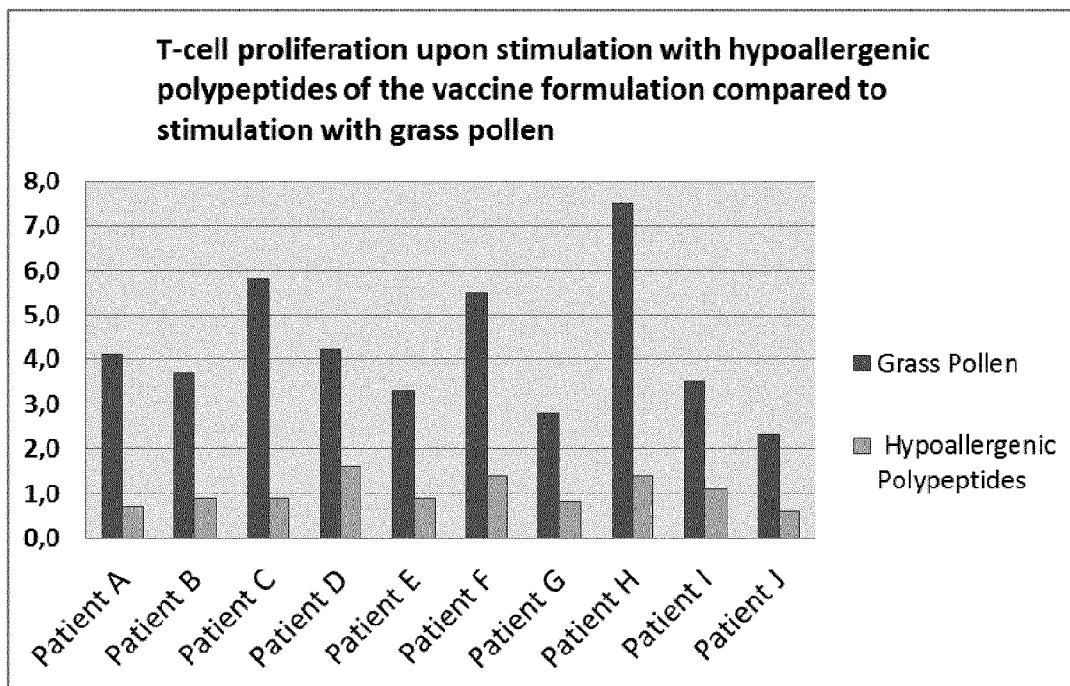

FIG. 15 shows the results of T-cell proliferation assays performed on T-cells from grass pollen allergic individuals after immunization with a vaccine formulation consisting of a mixture of the 4 hypoallergenic fusion proteins with SEQ ID No. 14, SEQ ID No. 15, SEQ ID No. 16, and SEQ ID NO. 17. The T-cell reactivity is strongly reduced or absent if compared to grass pollen. The y-axis of the graph reflects the stimulation index.

Figure 16A:
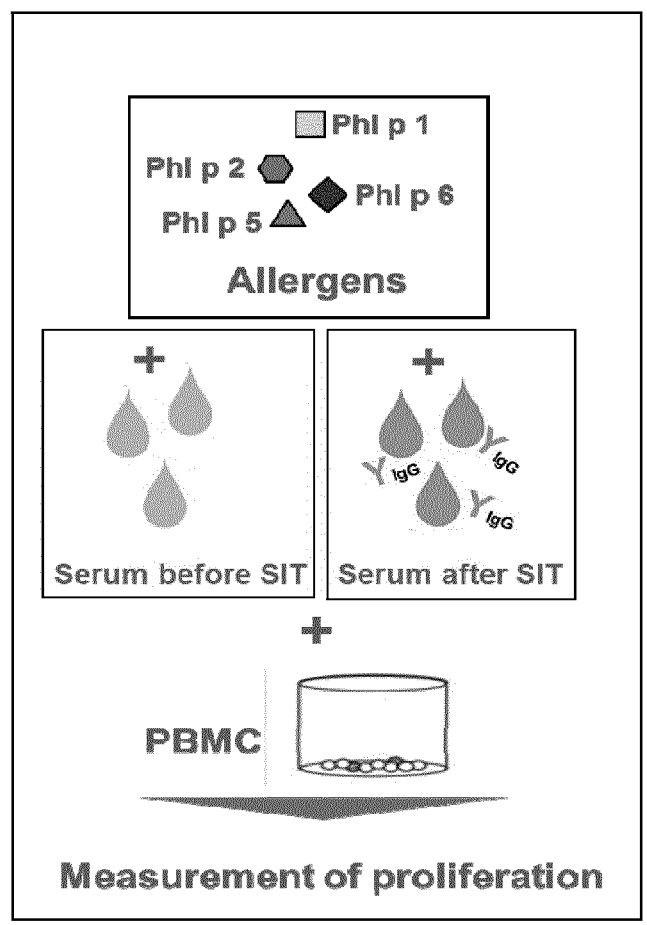
Figure 16B:
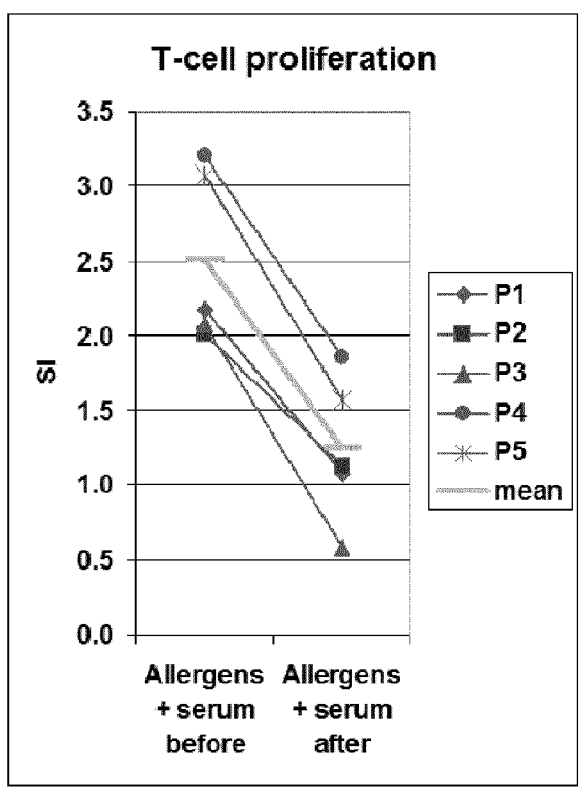

FIG. 16 shows that IgG induced by therapy with a vaccine formulation (BM32) comprising a mixture of the 4 hypoallergenic fusion proteins with SEQ ID No. 14, SEQ ID No. 15, SEQ ID No. 16, and SEQ ID NO. 17 reduces lymphoproliferative responses to grass pollen allergens in human PBMCs. (a) experimental set-up. (b) Results from T-cell proliferation assays performed in the absence (+serum before) and presence (+serum after) of treatment-induced IgG. The y-axis of the graph reflects the stimulation index. P1-P5 indicate results from different study participants.

Figure 17:
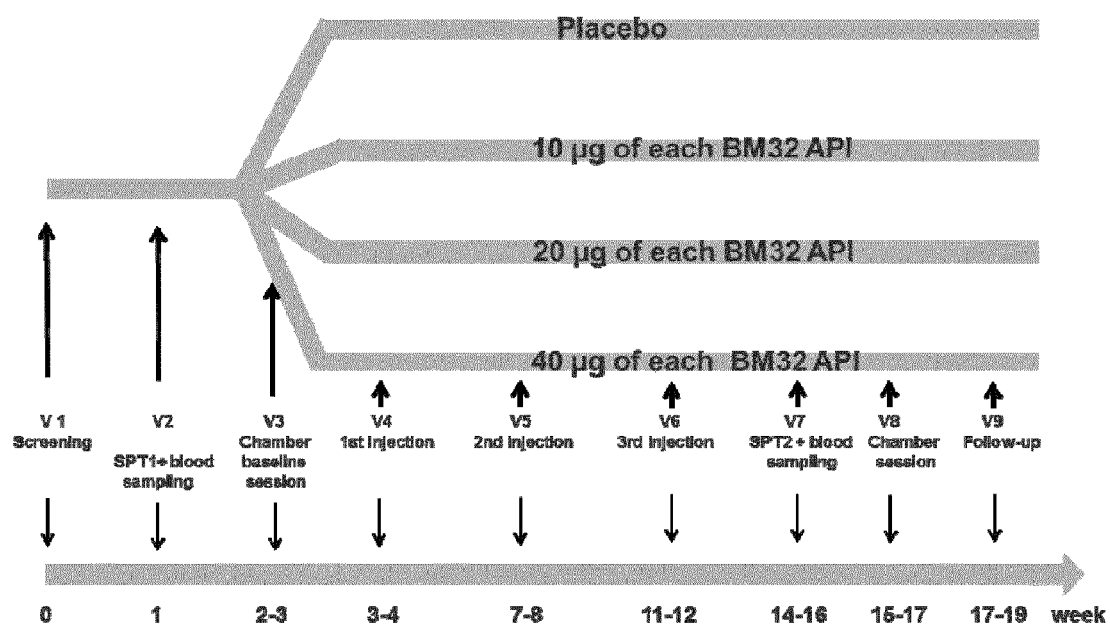

FIG. 17 shows the set-up of a clinical study carried out in 69 grass pollen allergic individuals using the vaccine formulation BM32 comprising a mixture of the 4 hypoallergenic fusion proteins with SEQ ID No. 14, SEQ ID No. 15, SEQ ID No. 16, and SEQ ID NO. 17

FIG. 18 A shows the primary sequence of fusion protein HBV Der p2-2xP2-2xP4 (sequence ID Nr. 149)

FIG. 18 B shows the primary sequence of fusion protein HBV Der p2-3xP2-3xP4 (sequence ID Nr. 150)

FIG. 18 C shows the primary sequence of fusion protein HBV Der p23-2xP4-2xP5 (sequence ID Nr. 151)

FIG. 18 D shows the primary sequence of fusion protein HBV Der p23-4xP6 (sequence ID Nr. 152)

Figure 19A:
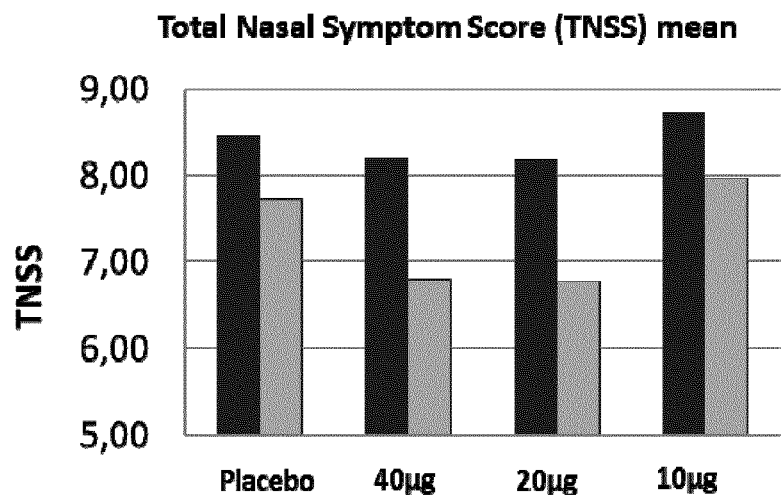

FIG. 19A shows the change in nasal symptoms induced by treatment with 3 subcutaneous injections of the vaccine formulation BM32 comprising a mixture of the 4 hypoallergenic fusion proteins with SEQ ID No. 14, SEQ ID No. 15, SEQ ID No. 16, and SEQ ID NO. 17. Black bars: before treatment, grey bars: after treatment.

Figure 19B:
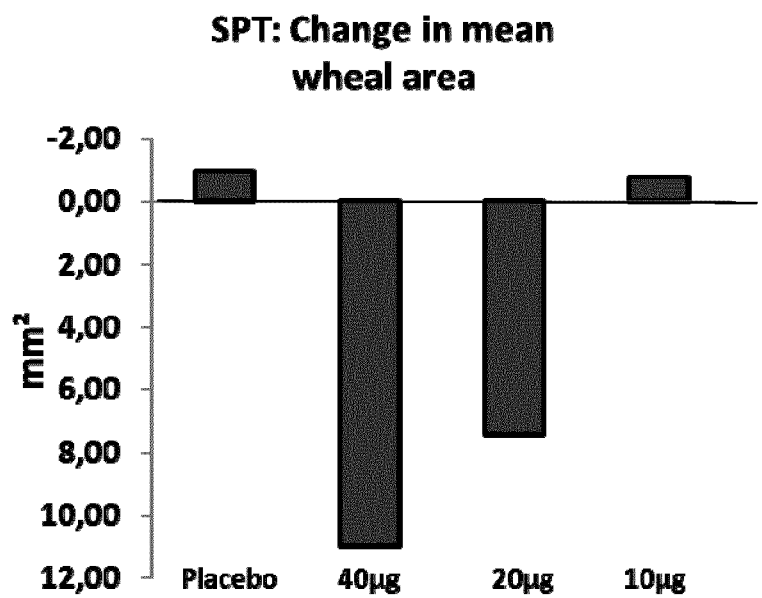

FIG. 19B shows the change in the mean wheal area between titrated skin prick test before and after treatment with the vaccine formulation BM32. The titrated skin prick test was carried out using 8 serial dilutions of grass pollen extract (undiluted to 1:128).

Figure 20:
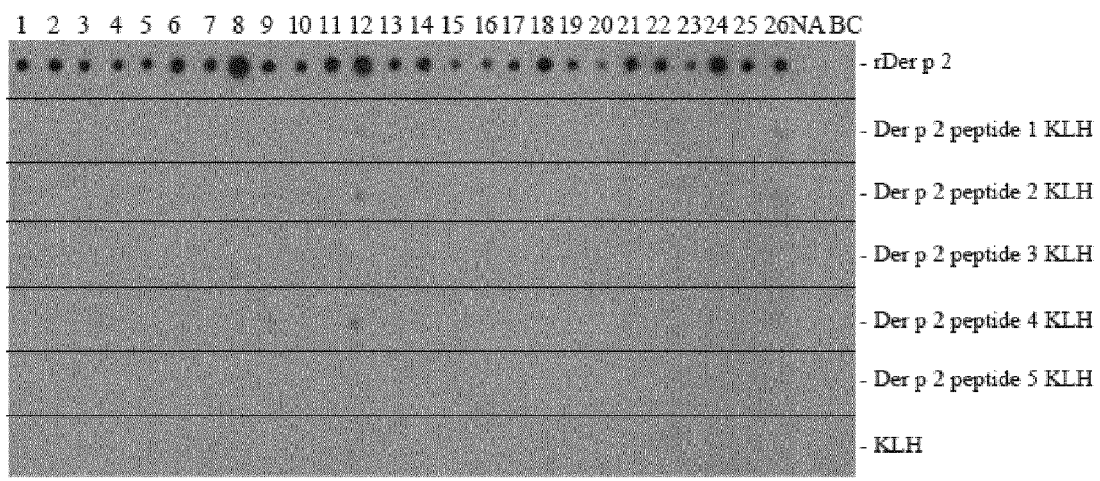

FIG. 20 shows IgE binding of the Der p 2 derived peptides in comparison to the complete allergen tested by an IgE dot-blot assay. Sera from 26 house dust mite allergic patients were incubated with dotted KLH-conjugated peptides and bound IgE was detected with 125I-labelled anti-human IgE. No IgE binding was detected for any of the 5 peptides as in example 26.

EXAMPLES

Example 1

Construction of Expression Plasmid for HBV_Phlp1_4xP5 (BM321)

The synthetic BM321 gene were assembled from synthetic oligo-nucleotides and/or PCR products and was cloned into an appropriate standard vector (pMK-RQkanR). The plasmid was purified from a transformed *E. coli* K12 strain (DH10B-T1R) and concentration was determined by UV spectroscopy. The final synthetic and codon-optimized BM321 DNA-sequence was further cloned into the expression vector pET28b (+) using appropriate restriction sites (NcoI site at the 5"-end and EcoRI at the 3"-end). The plasmid DNA was purified from transformed *E. coli* K12 DH10B (dam+ dcm+) and concentration determined by UV spectroscopy. The final construct was verified by sequencing of the insert. A summary of plasmid data and a plasmid map of final expression vector "pBM-321" is shown below.

Summary of BM321 Sequence Cloned into Final Expression Vector pET-28b(+).

| Sequence | Alias name sequence | Gene size | Plasmid size | Plasmid name | Restriction sites |
|---|---|---|---|---|---|
| BM321 | HBV_Phlp1_4xP5 | 882 bp | 6153 bp | pBM-321 | NcoI/EcoRI |

Example 2

Transformation of Expression Plasmid into Expression Host for HBV_Phlp1_4xP5 (BM321)

Chemically competent *E. coli* BL21(DE3) cells were transformed with the expression plasmid by heat shock method. Transformed cells were plated on LB-agar-plates consisting of 0.5% sodium chloride 1% soy peptone, 0.5% yeast extract, 1.5% agar and 50 µg/mL kanamycin for selection. Cells on LB plates were grown by over-night cultivation at 37° C. Single colonies of transformed BL21(DE3) *E. coli* cells were isolated, cultured in LB-medium and screened for growth and expression of BM321. The best performing clone was selected for the further establishment of a Master Cell Bank.

Example 3

Preparation of a Master Cell Bank for HBV_Phlp1_4xP5 (BM321)

An aliquot of the selected clone was used for inoculation of 150 mL culture medium (composition: 0.5% sodium chloride, 1% soy peptone, 0.5% yeast extract, 50 µg/mL kanamycin). The Master Cell Bank (MCB) culture was incubated at 37° C. under constant agitation at 200 rpm until the culture reached an optical density of $OD_{600}$=1-2. Glycerol was added in order to obtain a final glycerol concentration of 15% v/v and the MCB was aliquoted into 1 mL vials and stored in an ultra deep freezer at −75±10° C.

Example 4

High Cell Density Fed-Batch Fermentation of HBV_PhlP1_4xP5 (BM321)

Synthetic culture medium (100 mL, pH=6.8, salts and trace elements, 10 g/L glucose as carbon source) was inoculated with 1 mL of Master Cell Bank (*E. coli* BL21(DE3)/pBM321) and cultured in a shake flask (37° C., 200 rpm) until an optical density target value of OD=1 was reached. A 22 L stainless steel fermenter was used to perform the fed-batch fermentation. For automatic and reproducible feed control, a recipe was programmed allowing to pre-define specific growth-rate, feed rate, duration of batch-phase and duration of exponential feed-phase. In order to increase the oxygen transfer rate of the fermenter, back-pressure was controlled and set to 1 bar. The fermenter was in-situ sterilized with the synthetic culture medium as mentioned above and the fermentation was started by inoculation with preculture. After depletion of glucose, the exponential feeding phase was started in order to maintain a specific growth rate of $\mu$=0.25 $h^{-1}$. At an OD=45, the expression of recombinant BM321 was induced by the bolus addition of IPTG (0.8 mM final concentration). The culture was harvested at $OD_{600}$=73. BM321 product titer obtained from the fed-batch fermentation was 1.2 g per L culture broth. Afterwards, the bacterial culture broth was cooled down to ≤20° C. and centrifuged at 7,000 rpm (5,500 g) at 4° C. for 15 min. Wet cell biomass was aliquoted and stored at −75° C.

Example 5

Cell Disruption and Clarification

For cell disruption, 748 gram biomass from Example 6 were thawed and subdivided into aliquots á 125 gram and resuspended in a homogenization buffer (20 mM Tris, 1 mM EDTA, 0.1% Triton X-100, pH 11.0) under mechanical agitation at room temperature for 30 min. For cell disruption, a freeze/thaw procedure was applied by freezing −75° C. and subsequent thawing, followed by mechanical homogenisation. The pH of the homogenate was adjusted to pH=10.0. The crude cell homogenate was subjected to a centrifugation step at 7,000 rpm (5,500 g) at 4° C. for 30 min. The supernatants were subjected to precipitation with PEI (polyethyleneimine) under mechanical agitation. Insoluble matters were separated by a subsequent centrifugation step. The clarified supernatants were subjected to the following chromatography step.

Example 6

Chromatographic Purification of HBV_Phlp1_4xP5 (BM321)

A total of 1840 mL of the PEI precipitation supernatant from the clarification step as described in Example 7 were loaded on a 5×30 cm Q-Sepharose FF column and equilibrated with buffer A (TrisHCl, EDTA). Unbound material was removed by washing with buffer A, followed by a wash with buffer C (1 sodium phosphate, EDTA, pH 7.0). Elution of the product fraction was accomplished by a linear gradient elution with 0-100% BM32 buffer E (sodium phosphate, EDTA, NaCl pH 7.0) in BM32 buffer C. Selection of product-containing fractions for pooling was performed according to SDS-PAGE analysis, by densitometric evaluation of fraction purity and by product band intensity.

The pooled fractions from the capture step were adjusted to a conductivity of 115 mS/cm by the addition of 2.5 M sodium chloride, and this feedstock was loaded on a Phenyl Sepharose HP column equilibrated with buffer D (sodium phosphate, EDTA, NaCl pH 7.0). Unbound material was removed by washing with buffer D. Elution of the product fraction was accomplished by a gradient elution from 40-100% buffer C (sodium phosphate, EDTA, pH 7.0) in buffer D. Selection of product-containing fractions for pooling was performed according to SDS-PAGE analysis, by densitometric evaluation of fraction purity and by product band intensity.

The pooled fractions from the intermediate step were adjusted to a conductivity of 80 mS/cm by the addition of 2.5 M sodium chloride, and this feedstock was loaded on a Toyopearl Butyl 650-S column equilibrated with a mixture buffer F (sodium phosphate, EDTA, NaCl pH 7.0). Unbound material was removed by a gradient wash with 80-0% BM32 buffer F in buffer C (sodium phosphate, EDTA, pH 7.0). Elution of the fraction was accomplished by a gradient elution from 0-1 buffer G (sodium phosphate, EDTA, isopropanol, pH 7.0) in buffer C. Selection of product-containing fractions for pooling was performed according to SDS-PAGE analysis, by densitometric evaluation of fraction purity and by product band intensity.

Example 7

Manufacturing of HBV_Phlp2_4xP3 (BM322), HBV_Phlp5_V2 (BM325), and HBV_Phlp6_4xP1 (BM326)

For expression and manufacturing of the recombinant molecules according to the invention, namely HBV_Phlp2_4xP3 (BM322), HBV_Phlp5_V2 (BM325), and HBV_Phlp6_4xP1 (BM326), the same, similar or comparable methods and procedures as described in Example 1, Example 2, Example 3, Example 4, Example 5 and Example 6 were applied.

Example 8

Preparation of an Injectable Formulation Consisting of a Mixture of HBV_PhlP1_4xP5 (BM321); HBV_PhlP2_4xP3 (BM322), HBV_PhlP5_V2 (BM325), and HBV_PhlP6_4xP1 (BM326)

Each of the recombinant purified proteins was dissolved in an isotonic buffer containing 0.9% sodium chloride and 2 mM sodium phosphate and to each protein solution an appropriate amount of aluminium hydroxide was added. A mixture containing equal parts of the four resulting suspensions was prepared and aliquoted under sterile condition into sealed vials. The injectable formulation obtained by this procedure contained 0.4 mg/mL of each HBV_PhlP1_4xP5; HBV_PhlP2_4xP3, HBV_PhlP5_V2 and HBV_PhlP6_4xP1.

Example 9

Preparation of his-Tagged HBV_Betv1_4xPA

The gene coding for fusion proteins consisting of PreS fused with Bet v 1-derived peptide PA twice at the N- and C-terminus (i.e. 4PA-PreS) was synthesized by ATG:biosynthetics, Merzhausen, Germany and inserted into the NdeI/XhoI sites of the vector pET-17b (Novagen, Germany). The DNA sequences were confirmed by means of automated sequencing of both DNA strands (Microsynth, Balgach, Switzerland).

The fusion protein was expressed in *E. coli* strain BL21 (DE3; Stratagene, La Jolla, Calif.). Cells were grown in Luria Bertani-medium containing 50 μg/mL kanamycin to an OD of 0.6. Protein expression was induced by adding isopropyl-β-D-thiogalactopyranoside to a final concentration of 1 mmol/L over night at 37° C. Cells were harvested by centrifugation at 3500 rpm for 10 minutes. The protein product was mainly detected in the inclusion body fraction. It was solubilized in 6M GuHCl, 100 mM NaH2PO4, 10 mM TRIS, pH 8.0 over night. The homogenate was centrifuged at 14,000 g for 18 minutes. Supernatants of were incubated with 2 mL of a previously equilibrated Ni-NTA resin for 4 hours (Qiagen, Hilden, Germany) and the suspensions were subsequently loaded onto a column, washed with 2 column volumes of washing buffer (8 mol/L urea, 100 mmol/L NaH2PO4, and 10 mmol/LTris-HCl [pH=6.1]), and eluted with the same buffer (pH=3.5). The purified protein was dialyzed against water.

The purity of recombinant proteins was analyzed by Coomassie-stained SDS-PAGE (12.5%) under reducing conditions.

The identity of the fusion protein was confirmed by the means of dot blot using monoclonal antibodies, specific for Bet v 1-derived peptides P2' (mAb2) and P4' (mAb12) and PreS-specific rabbit antibodies as well as corresponding rabbit preimmune IgGs. One μg of PreS fusion proteins, PreS and HSA (control) have been immobilized on nitrocellulose and were incubated with monocolonal as well as rabbit sera diluted 1:1000 have at 4° C. Bound antibodies were detected with iodine $^{125}$-labelled rabbit anti-mouse IgG (mAb2, mAb12) or $^{125}$I-goat anti-rabbit IgG (rabbit anti-PreS, rabbit preimmune) (Perkin-Elmer, Waltham, Mass.) diluted 1:500 for 2 hours and visualized by autoradiography. Furthermore ELISA plates (Maxisorp, Nunc, Denmark) were coated with 2 μg of PreS fusion protein and PreS, diluted in 0.1 mol/L carbonate buffer, pH 9.6 washed with PBS containing 0.05% vol/vol Tween 20 (PBST) 3 times and blocked for 2 hours with 1% BSA-PBST. Subsequently plates were incubated with mAb2, mAb12, anti-PreS rabbit serum and rabbit anti-Bet v 1 antibodies in a dilution of 1:5000 (dilution buffer: 0.5% wt/vol BSA in PBST) overnight at 4° C. After washing 5 times, bound IgG antibodies have been detected with a HRP-labelled sheep anti-mouse antibody (for mAb2, mAb12) or HRP-labelled donkey anti-rabbit antibody (rabbit sera) (both GE Healthcare, Uppsala, Sweden) and colour reaction was developed.

Example 10

Preparation of his-Tagged HBV_Betv1_2xPA2xPB (BM31)

Genes coding for fusion protein consisting of PreS fused twice with Bet v 1-derived peptides at the N- and C-terminus 2xPA2xPB-PreS) was synthesized by GenScript Piscataway, N.J., USA, 2PAPB-Pres) and inserted into the NdeI/XhoI sites of the vector pET-17b (Novagen, Germany). The DNA sequences were confirmed by means of automated sequencing of both DNA strands (Microsynth, Switzerland).

The recombinant PreS fusion proteins was expressed in *E. coli* strain BL21 (DE3; Stratagene, Calif.). Cells were grown in Luria Bertani-medium containing 50 μg/mL kanamycin to an OD of 0.6. Protein expression was induced by adding isopropyl-β-D-thiogalactopyranoside to a final concentration of 1 mmol/L over night at 37° C. Cells were harvested by centrifugation at 3500 rpm for 10 minutes. Proteins were mainly detected in the inclusion body fraction. The resulting protein was solubilized in 6M GuHCl, 100 mM NaH2PO4, 10 mM TRIS, pH 8.0 over night. The homogenate was centrifuged at 14,000 g for 18 minutes. Supernatants of were incubated with 2 mL of a previously equilibrated Ni-NTA resin for 4 hours (Qiagen, Hilden, Germany) and the suspensions were subsequently loaded onto a column, washed with 2 column volumes of washing buffer (8 mol/L urea, 100 mmol/L NaH2PO4, and 10 mmol/LTris-HCl [pH=6.1]), and eluted with the same buffer (pH=3.5). Protein was dialyzed against 10 mM NaH2PO4.

The purity of recombinant proteins was analyzed by Coomassie-stained SDS-PAGE (12.5%) under reducing conditions. The identity of the fusion proteins was confirmed by the means of dot blot using monoclonal antibodies, specific for Bet v 1-derived peptides P2' (mAb2) and P4' (mAb12) and PreS-specific rabbit antibodies as well as corresponding rabbit preimmune IgGs. One μg of PreS fusion protein, PreS and HSA (control) have been immobilized on nitrocellulose and were incubated with monocolonal as well as rabbit sera diluted 1:1000 have at 4° C. Bound antibodies were detected with iodine 125-labelled rabbit anti-mouse IgG (mAb2, mAb12) or 125I-goat anti-rabbit IgG (rabbit anti-PreS, rabbit preimmune) (Perkin-Elmer, Waltham, Mass.) diluted 1:500 for 2 hours and visualized by autoradiography. Furthermore ELISA plates (Maxisorp, Nunc, Rosklide, Denmark) were coated with 2 µg of PreS fusion protein and PreS, diluted in 0.1 mol/L carbonate buffer, pH 9.6 washed with PBS containing 0.05% vol/vol Tween 20 (PBST) 3 times and blocked for 2 hours with 1% BSA-PBST. Subsequently plates were incubated with mAb2, mAb12, anti-PreS rabbit serum and rabbit anti-Bet v 1 antibodies in a dilution of 1:5000 (dilution buffer: 0.5% wt/vol BSA in PBST) overnight at 4° C. After washing 5 times, bound IgG antibodies have been detected with a HRP-labelled sheep anti-mouse antibody (for mAb2, mAb12) or HRP-labelled donkey anti-rabbit antibody (rabbit sera) (both GE Healthcare, Uppsala, Sweden) and colour reaction was developed.

Example 11

Detection of IgE Reactivity of Fusion Protein HBV_Phlp1_4xP5 (BM321)

IgE binding in comparison to the complete allergen was tested by IgE dot-blot assay. Sera from grass pollen allergic patients were incubated with dotted proteins and bound IgE was detected with 125I-labelled anti-human IgE. No IgE binding was detected for HBV_Phlp1_4xP5 (BM321) as shown in FIG. 4A.

Example 12

Detection of IgE Reactivity of Fusion Protein HBV_Phlp2_4xP3 (BM322)

IgE binding in comparison to the complete allergen was tested by IgE dot-blot assay. Sera from grass pollen allergic patients were incubated with dotted proteins and bound IgE was detected with 125I-labelled anti-human IgE. No IgE binding was detected for HBV_Phlp2_4xP3 (BM321) as shown in FIG. 4B.

Example 13

Detection of IgE Reactivity of Fusion Protein HBV_Phlp5_V2 (BM325)

IgE binding in comparison to the complete allergen was tested by IgE dot-blot assay. Sera from grass pollen allergic patients were incubated with dotted proteins and bound IgE was detected with 125I-labelled anti-human IgE. No IgE binding was detected for HBV_Phlp5_V2 (BM325) as shown in FIG. 4C.

Example 14

Detection of IgE Reactivity of Fusion Protein HBV_Phlp6_4xP1 (BM326)

IgE binding in comparison to the complete allergen was tested by IgE dot-blot assay. Sera from grass pollen allergic patients were incubated with dotted proteins and bound IgE was detected with 125I-labelled anti-human IgE. No IgE binding was detected for HBV_Phlp1_4xP1 (BM326) as shown in FIG. 4D.

Example 15

Detection of IgE Reactivity of Fusion Protein HBV_etV1_4xPA and HBV_Betv1_2xPA2xPB (BM31)

IgE binding in comparison to the complete allergen was tested by IgE dot-blot assay. Sera from grass pollen allergic patients were incubated with dotted proteins and bound IgE was detected with 125I-labelled anti-human IgE. No IgE binding was detected for both fusion proteins as shown in FIG. 5

Example 16

Rabbit Anti-r89P5 Antibodies Block Patient's IgE-Binding to rPhl p 1

To determine the ability of peptide-induced rabbit Ig to inhibit the binding of allergic patients' IgE antibodies to rPhl p 1, ELISA plates were coated with 1 µg/ml rPhl p 1, washed and blocked. The plates were preincubated with 1:100-diluted rabbit anti-peptide (HBV_Phlp1_4xP5, KLHP5), a rabbit anti rPhl p 1 and, for control purposes, with the corresponding preimmune sera. After washing, plates were incubated with human sera from Phl p 1-allergic patients (1:3 diluted) and bound IgE was detected with mouse anti-human IgE (Pharmingen 1:1000) and then with sheep anti-mouse IgG POX-coupled (Amersham Bioscience) 1:2000. The percentage of inhibition of IgE-binding achieved by preincubation with the anti-peptide antisera was calculated as follows: $100 - OD_i/OD_P \times 100$.

$OD_i$ and $OD_P$ represent the extinctions after preincubation with the rabbit immune and preimmune serum, respectively. Table 1 shows the capacity of anti-Phl p 1 peptide antibodies to inhibit the binding of 13 allergic patients' IgE to complete rPhl p 1. Anti-fusion protein sera blocked the IgE-binding to the same extent as sera against rPhl p 1 and KLHP5. Table 2 shows the inhibition (in %) of all 13 patients.

TABLE 1

% inhibition of 13 patients' IgE-binding to rPhl p 1 after incubation with rabbit anti-rPhl p 1, anti-HBV_Phlp1_4xP5 and anti-KLHP5 antisera

| | % inhibition | | |
|---|---|---|---|
| patient | rPhl p 1 | HBV_Phlp1_4xP5 | KLHP5 |
| 1 | 83.63 | 86.11 | 85.17 |
| 2 | 88.74 | 95.69 | 93.85 |
| 3 | 95.66 | 96.80 | 98.42 |
| 4 | 97.43 | 97.72 | 96.29 |
| 5 | 92.77 | 90.84 | 88.45 |
| 6 | 93.56 | 91.93 | 90.07 |
| 7 | 95.00 | 94.56 | 96.84 |
| 8 | 85.25 | 89.10 | 90.05 |
| 9 | 97.07 | 104.72 | 93.73 |
| 10 | 91.55 | 103.02 | 95.47 |
| 11 | 98.85 | 102.43 | 100.49 |
| 12 | 94.01 | 92.12 | 93.91 |
| 13 | 87.75 | 59.62 | 42.98 |
| Mean | 92.41 | 92.59 | 89.67 |

Example 17

Rabbit Anti-HBV_Phlp2_4xP3 Antibodies Block Patient's IgE-Binding to rPhl p 2

To determine the ability of peptide-induced rabbit Ig to inhibit the binding of allergic patients' IgE antibodies to rPhl p 2, ELISA plates were coated with 1 μg/ml rPhl p 2, washed and blocked. The plates were preincubated with 1:100-diluted rabbit anti-peptide (HBV_Phlp2_4xP3, KLHP3), a rabbit anti rPhl p 2 and, for control purposes, with the corresponding preimmune sera. After washing, plates were incubated with human sera from Phl p 2-allergic patients (1:3 diluted) and bound IgE was detected with mouse anti-human IgE (Pharmingen 1:1000) and then with sheep anti-mouse IgG POX-coupled (Amersham Bioscience) 1:2000. The percentage of inhibition of IgE-binding achieved by preincubation with the anti-peptide antisera was calculated as follows: $100-OD_i/OD_P \times 100$.

$OD_i$ and $OD_P$ represent the extinctions after preincubation with the rabbit immune and preimmune serum, respectively. Table 2 shows the capacity of anti-Phl p 2 peptide antibodies to inhibit the binding of 19 allergic patients' IgE to complete rPhl p 2. Anti-fusion protein sera blocked the IgE-binding to the same extent as sera against rPhl p 2 and KLHP3. Table 2 shows the inhibition (in %) of all 19 patients.

TABLE 2

% inhibition of 19 patients' IgE-binding to rPhl p 2 after incubation with rabbit anti-rPhlp 1, anti-HBV_Phlp2_4xP3 and anti-KLHP3 antisera

| patient | rPhl p 2 | HBV_Phlp2_4xP3 | KLHP3 |
|---|---|---|---|
| 1 | | 98.24 | 81.36 |
| 2 | | 97.50 | 83.90 |
| 3 | 96.46 | 98.57 | 90.58 |
| 4 | | 98.31 | 86.77 |
| 5 | | 96.46 | 81.17 |
| 6 | | 99.43 | 72.45 |
| 9 | 91.25 | 91.38 | 90.44 |
| 8 | | 95.78 | 54.49 |
| 9 | | 98.60 | 87.55 |
| 10 | | 95.45 | 82.68 |
| 11 | 91.36 | 96.70 | 78.21 |
| 12 | | 98.47 | 90.21 |
| 13 | | 97.67 | 93.20 |
| 14 | | 96.57 | 85.64 |
| 15 | | 97.00 | 91.35 |
| 16 | 93.73 | 98.06 | 83.62 |
| 17 | | 95.55 | 76.27 |
| 18 | | 95.91 | 86.49 |
| 19 | | 95.90 | 83.99 |
| Mean | 93.20 | 97.19 | 83.18 |

Example 18

Rabbit Anti-HBV_Phlp5_V2 Antibodies Block Patient's IgE-Binding to rPhl p 5

To determine the ability of peptide-induced rabbit Ig to inhibit the binding of allergic patients' IgE antibodies to rPhl p 5, ELISA plates were coated with 1 μg/ml rPhl p 5, washed and blocked. The plates were preincubated with 1:100-diluted rabbit anti-peptide (HBV_Phlp2_V2), a rabbit anti rPhl p 5 and, for control purposes, with the corresponding preimmune sera. After washing, plates were incubated with human sera from Phl p 5-allergic patients (1:3 diluted) and bound IgE was detected with mouse anti-human IgE (Pharmingen 1:1000) and then with sheep anti-mouse IgG POX-coupled (Amersham Bioscience) 1:2000. The percentage of inhibition of IgE-binding achieved by preincubation with the anti-peptide antisera was calculated as follows: $100-OD_i/OD_P \times 100$.

$OD_i$ and $OD_P$ represent the extinctions after preincubation with the rabbit immune and preimmune serum, respectively. Table 3 shows the capacity of anti-Phl p 5 peptide antibodies to inhibit the binding of 16 allergic patients' IgE to complete rPhl p 5. Anti-fusion protein sera blocked the IgE-binding to the same extent as sera against rPhl p 5 and better than KLH peptide mix. Table 3 shows the inhibition (in %) of all 16 patients.

TABLE 3

% inhibition of 13 patients' IgE-binding to rPhl p 5 after incubation with rabbit anti-rPhl p 1, anti-HBV_Phlp5_V2 and anti-KLH peptide mix antisera

| | % inhibition | | |
|---|---|---|---|
| patient | rPhl p 5 | HBV_Phlp5_V2 | KLHPmix |
| 1 | 99.00 | 96.69 | 91.74 |
| 2 | 94.57 | 94.15 | 68.42 |
| 3 | 98.98 | 95.88 | 85.74 |
| 4 | 97.39 | 88.38 | 80.23 |
| 5 | 98.95 | 93.74 | 62.33 |
| 6 | 98.52 | 93.36 | 78.82 |
| 9 | 97.22 | 91.35 | 79.94 |
| 8 | 96.02 | 89.70 | 80.14 |
| 9 | 97.09 | 88.48 | 61.11 |
| 10 | 99.30 | 84.03 | 92.92 |
| 11 | 99.50 | 94.09 | 86.46 |
| 12 | 95.45 | 88.97 | 81.31 |
| 13 | 96.22 | 93.34 | 60.87 |
| 14 | 90.86 | 94.80 | 83.02 |
| 15 | 98.45 | 94.15 | 83.60 |
| 16 | 94.68 | 92.46 | 91.77 |
| Mean | 97.01 | 92.10 | 79.28 |

Example 19

Rabbit Anti-HBV_Phlp6_4xP1 Antibodies Block Patient's IgE-Binding to rPhl p 6

To determine the ability of peptide-induced rabbit Ig to inhibit the binding of allergic patients' IgE antibodies to rPhl p 6, ELISA plates were coated with 1 μg/ml rPhl p 6, washed and blocked. The plates were preincubated with diluted rabbit anti-peptide (HBV_Phlp6_4xP1, KLHP1), a rabbit anti rPhl p 6 and, for control purposes, with the corresponding preimmune sera. After washing, plates were incubated with human sera from Phl p 6-allergic patients (1:3 diluted) and bound IgE was detected with mouse anti-human IgE (Pharmingen 1:1000) and then with sheep anti-mouse IgG POX-coupled (Amersham Bioscience) 1:2000. The percentage of inhibition of IgE-binding achieved by preincubation with the anti-peptide antisera was calculated as follows: $100-OD_i/OD_P \times 100$. $OD_i$ and $OD_P$ represent the extinctions after preincubation with the rabbit immune and preimmune serum, respectively. Table 4 shows the capacity of anti-Phl p 6 peptide antibodies to inhibit the binding of 21 allergic patients' IgE to complete rPhl p 6. Anti-fusion protein sera blocked the IgE-binding to the same extent as sera against rPhl p 6 and KLHP1. Table 4 shows the inhibition (in %) of all 21 patients.

TABLE 4

% inhibition of 21 patients' IgE-binding to rPhl p 6 after incubation with rabbit anti-rPhlp 6, anti-HBV_Phlp6_4xP1 and anti-KLHP1 antisera

| | % inhibition | | |
|---|---|---|---|
| patient | rPhl p 6 | HBV_Phlp6_4xP1 | KLHP1 |
| 1 | 96.52 | 95.96 | 95.64 |
| 2 | 88.26 | 91.20 | 88.06 |
| 3 | 95.07 | 95.39 | 94.10 |
| 4 | 82.77 | 83.74 | 81.98 |
| 5 | 96.71 | 96.35 | 95.20 |
| 6 | 95.46 | 93.38 | 92.83 |
| 7 | 90.52 | 88.07 | 86.06 |
| 8 | 86.69 | 85.14 | 83.08 |
| 9 | 89.09 | 91.56 | 89.00 |
| 10 | 97.05 | 96.48 | 97.42 |
| 11 | 86.97 | 89.19 | 84.95 |
| 12 | 37.22 | 49.14 | 44.90 |
| 13 | 75.97 | 79.19 | 75.85 |
| 14 | 91.05 | 92.13 | 87.93 |
| 15 | 89.01 | 88.25 | 85.82 |
| 16 | 92.46 | 91.82 | 91.30 |
| 17 | 78.99 | 84.13 | 77.93 |
| 18 | 47.25 | 67.02 | 67.825 |
| 19 | 93.84 | 86.62 | 79.841 |
| 20 | 58.42 | 56.69 | 71.388 |
| 21 | 39.92 | 56.69 | 67.797 |
| Mean | 81.39 | 83.36 | 82.81 |

Example 20

IgE Reactivity of PreS Fusion Proteins Determined by Dot Blot and ELISA

Purified rBet v 1, recombinant fusion proteins 4xPA-PreS, 2xPA2xPB-PreS were tested for their IgE reactivity by RAST-based, non-denaturing dot blot assays. Two µg of the purified proteins and, for control purposes, HSA were dotted onto nitrocellulose membrane strips (Schleicher & Schuell, Dassel, Germany).

Nitrocellulose strips were blocked in buffer A (Vrtala, J Clin Invest, 1997) and incubated with sera from birch pollen allergic patients (n=50), sera from non-allergic persons (n=3) diluted 1:10, buffer control and positive control (1:1000 diluted rabbit anti-rBet v 1 antiserum). Bound IgE antibodies were detected with $^{125}$I-labelled anti-human IgE antibodies (BSM Diagnostica, Vienna, Austria), bound rabbit antibodies with a $^{125}$I-labeled goat anti-rabbit antiserum (Perkin-Elmer) and visualized by autoradiography (Valenta et al., 1992). Additionally, ELISA plates were coated with rBet v 1 and the purified PreS fusion proteins (5 µg/mL). After washing and blocking as described above, plates were incubated with sera of birch pollen allergic patients (n=21) and three non-allergic control sera diluted 1:5. Bound IgE was detected by purified mouse anti human IgE (BD Pharmingen) diluted 1:1000 overnight and visualized with HRP-labelled sheep anti mouse IgG (GE Healthcare) diluted 1:2000. After washing, colour reaction was determined as described above.

Example 21

Allergen-Induced Upregulation of CD203c of Allergic Patients' Basophils

Heparinized blood samples were obtained from birch allergic patients after informed consent was given and were incubated with increasing concentrations of rBet v 1, 4PA-PreS, 2PAPB-PreS ranging from 0.001 to 1 mg/mL, a monoclonal anti-IgE antibody (Immunotech, Marseille, France) as positive control, or PBS (negative control) for 15 min (37° C.). CD 203c expression was determined as previously described.

Example 22

Lymphoproliferative Responses and Cytokine Induction in PBMC from Birch Pollen Allergic Patients PBMCs from birch pollen allergic patients (n=6) have been isolated by Ficoll (Amersham Biosciences, Uppsala, Sweden) density gradient centrifugation. Subsequently PBMCs were resuspended in AIM V medium (Life Technologies, Grand Island, N.Y.) to a final concentration of $2\times10^5$ cells/well and stimulated with decreasing antigen doses (equimolar amounts of 5 µg/well rBet v 1, PA, PB, PreS, 2PA-PreS, 2PB-PreS, 4PA-PreS, 2PAPB-PreS), with medium alone (negative control) or with IL-2 (4 IE/well) (positive control). After 6 days, proliferative responses were measured by [$^3$H] thymidine incorporation and are expressed as stimulation indices (SI).

Furthermore cytokine production of 17 different cytokines (i.e. IL-10, IL-2, IL-4, IL-5, IL-6, IL-7, IL-8, IL-10, IL-12, IL-13, IL-17, IFN-γ, TNF-α, G-CSF, GM-CSF, MIP-1β, MCP-1) has been measured after 6 days of stimulation with Bio-plex Pro Human Cytokine 17-Plex Panel (Bio-Rad Laboratories) according the manufacturer's instructions. Briefly, the undiluted supernatants were mixed with anti-cytokine/chemokine mouse monoclonal antibodies coupled to different beads as capture antibodies (Bio-Rad). An 8-point standard curve was used to achieve low-end sensitivity. After washing, anti-cytokine biotinylated detection antibody was added. The reaction was visualized by adding Streptavidin-labelled Phycoerythrin (PE) and assay buffer. The samples were analyzed on a Luminex 100 instrument (Biosource, Nivelles, Belgium) and the data were acquired using the Bio-Plex Manager 6.0 software. All samples were analyzed in one run. Results are shown in FIG. 10.

Example 23

Analysis of Rabbit Sera Immunized with rBet v 1 and PreS Fusion Proteins for their Recognition of rBet v 1, Bet v 1 Homologous Allergens and Bet v 1-Derived Peptides by ELISA ELISA plates (Maxisorp, Nunc) were coated either with 1 µg/ml rBet v 1 or homologous allergens in alder (rAln g 1), hazel (rCor a 1), apple (rMal d1) and additionally with several Bet v 1-derived peptides in a concentration of 1 µg/ml overnight at 4° C. After washing and blocking as described above sera from rabbits immunized with rBet v 1 and the PreS fusion proteins conjugated to alum or CFA, were incubated in serial 1:2 dilutions ranging from 1:500 to 1:1 280 000 and in a concentration of 1:1000. Bound rabbit IgG was detected with HRP-labelled donkey anti-rabbit antibodies (GE Healthcare) and colour reaction was determined as described above.

Example 24

Inhibition of Allergic Patients' IgE Binding to rBet v 1

An inhibition ELISA was used to study the inhibition of the binding of birch pollen allergic patients' IgE to rBet v 1.

ELISA plates were coated with rBet v 1 in a concentration of 1 µg/ml at 4° C. overnight. After washing and blocking plates were pre-incubated with rabbit sera directed against the PreS fusion protein 2PAPB-PreS and anti-Bet v 1 rabbit serum in a dilution of 1:80 and 1:160 in comparison with rabbit preimmune sera overnight at 4° C. After an additional washing step sera of birch pollen allergic patients diluted 1:5 were added overnight at 4° C. and bound human IgE were detected with a 1:1000 diluted alkaline phosphatase-conjugated mouse monoclonal anti human IgE antibody (BD Pharmingen). The percentage of inhibition of IgE binding to rBet v 1 after pre-incubation with 2PAPB-PreS rabbit antisera and Bet v 1 rabbit antisera was calculated as follows: percent inhibition=$100-(OD^i \times 100/OD^p)$. $OD^p$ and $OD^i$ represent the extinctions after pre-incubation with specific rabbit IgG ($OD^i$) or preimmune sera ($OD^p$), respectively. (FIG. 12)

Example 25

Use of a Vaccine Formulation Comprising a Mixture of 4 Hypoallergenic Fusion Proteins for the Treatment of Grass Pollen Allergy in Grass Pollen Allergic Human Individuals An injectable formulation of hypoallergenic fusion proteins SEQ ID No. 14, SEQ ID No. 15, SEQ ID No. 16, and SEQ ID No. 17 with aluminum hydroxide was prepared as described in example 8. In the course of a clinical study, the vaccine was administered 3 times subcutaneously to 69 grass pollen allergic human subjects. (FIG. 17)

Vaccination with the vaccine formulation led to a robust IgG immune response. Induction of allergen-specific IgG following s.c. injection of the 3 different dose levels of the vaccine and placebo was determined by ELISA in the sera collected from the study participants before and after treatment with 3 s.c. injections of the vaccine formulation. (FIG. 14).

For this purpose, ELISA plates (Nunc Maxisorp, Roskilde, Denmark) were coated with 5 µg/ml of the antigens Phl p 1, Phl p 2, Phl p 5, and Phl p 6 or human serum albumin (HSA) as control over night at 4° C. After washing with PBS containing 0.5% Tween 20 (PT) and blocking with 2% w/v BSA in PT, plates were subsequently incubated with 1:10 to 1:100 diluted sera from patients, serum from a non-atopic individual or buffer alone in triplicates overnight at 4° C. Bound IgE antibodies were detected with HRP-coupled anti-human IgE antibodies diluted in PT, 0.5% w/v BSA. The colour development was performed by addition of staining solution ABTS (2,2'-Azino-bis(3-ethylbenzthiazoline-6-sulfonic acid)diammonium salt; Sigma-Aldrich, St. Louis, Mo., USA) (100 µl/well). The optical density was measured using an ELISA Reader at 405 nm. The results of IgG assessments are shown in FIG. 14.

The vaccine did not provoke any relevant T-cell reactivity towards the hypoallergenic fusion proteins present in the vaccine formulation as determined by in-vitro T-cell proliferation assay (FIG. 15), thus demonstrating the lack of T-cell reactivity of the hypoallergenic fusion proteins.

T-cell proliferation assays were performed using the following procedure: Peripheral blood mononuclear cells (PBMC) were isolated from heparinised blood samples of the grass pollen allergic patients by Ficoll (Amersham Pharmacia Biotech, Little Chalfont, UK) density gradient centrifugation. PBMC ($2 \times 10^5$) were then cultured in triplicates in 96-well plates (Nunclone; Nalge Nunc International, Roskilde, Denmark) in 200 µl serum-free Ultra Culture medium (BioWhittaker, Rockland, Me.) supplemented with 2 mM L-glutamin (SIGMA, St. Louis, Mo.), 50 µM b-mercaptoethanol (SIGMA) and 0.1 mg gentamicin per ml (SIGMA) at 37° C. and 5% $CO_2$ in a humidified atmosphere. Cells were stimulated with a mixture containing 0.25 µg of each polypeptide component of the vaccine and for comparison an equimolar concentrations of grasspollen extract or for control purposes with 4 U Interleukin-2 per well (Boehringer Mannheim, Germany) or medium alone. After 6 d culture 0.5 µCi per well [3H]thymidine (Amersham Pharmacia Biotech) was added and 16 h thereafter incorporated radioactivity was measured by liquid scintillation counting using a microbeta scintillation counter (Wallac ADL, Freiburg, Germany). Mean cpm were calculated from the triplicates and stimulation indices (SI) were calculated as the quotient of the cpm obtained by antigen or interleukin-2 stimulation and the unstimulated control. Results of proliferation assays are shown in FIG. 15.

Treatment with the vaccine induced IgG antibodies with the capability to modulate the allergen-specific T-cell response as demonstrated by a reduced proliferative response upon stimulation with grass pollen allergens in the presence of treatment-induced IgG. (FIG. 16). For this purpose, T-cell proliferation assays were performed with PBMCs isolated from study participants after treatment as described above with the exception that the stimulation was done with a mixture of the 4 grass pollen allergens Phl p 1, Phl p 2, Phl p5, and Phl p 6 (0.25 µg per allergen) together with serum collected from the same participant before and after the treatment. The experimental set-up and results are shown in FIG. 16.

Reduction of nasal allergy symptoms induced by provocation in a pollen chamber and reduction of skin reactivity as determined by titrated skin prick testing was observed in patients having received 3 injections containing either 20 µg or 40 µg of each of the 4 polypeptides while there was no reduction in those parameters after treatment with doses of 10 µg of each polypeptide. (see FIG. 19).

Example 26

Selection of Peptides Derived from House Dust Mite Allergen Der p 2 and Design of PreS Fusion Proteins Using Those Peptides The 5 non IgE binding Der p 2 derived peptides—Der p2 Pep1 (SEQ ID No. 96), Der p2 Pep2 (SEQ ID No. 97), Der p2 Pep3 (SEQ ID No. 98), Der p2 Pep4 (SEQ ID No. 99), and Der p2 Pep5 (SEQ ID No. 100)—were screened with respect to
  their IgE binding properties (dot blot assay)
  their potential to induce Der p 2 specific T-cell reactions, and (T-cell proliferation assay)
  their ability to induce Der p 2-specific antibodies with the capacity to block human patient's IgE to Der p 2 (inhibition ELISA using rabbit anti-peptide IgG)

For that purpose, each of the peptides was chemically coupled to KLH. KLH and chemical coupling of the peptides was used in this screening experiment because it is an easy-to-use and well established and straight forward model system allowing initial comparison of the different peptides.

IgE binding of the Der p 2 derived peptides in comparison to the complete allergen was tested by IgE dot-blot assay. Sera from 26 house dust mite allergic patients were incubated with dotted KLH-conjugated peptides and bound IgE was detected with 125I-labelled anti-human IgE. No IgE binding was detected for any of the 5 peptides as shown below.

To identify peptides which induce a low lymphoproliferative response in PBMC from house dust mite allergic patients PBMCs isolated from 10 patients were stimulated with the 5

Der p 2 derived peptides alone, the KLH-conjugated peptides, and wild-type Der p 2 for comparison.

PBMCs from all 10 patient were stimulated by the wild-type Der p 2, and there was no or only very low proliferation upon stimulation with Der p2 Pep1, Der p2 Pep2, and Der p2 Pep4. Stimulation with Der p2 Pep3 and Der p2 Pep5 however, resulted in significant proliferation of the PBMCs in 4 out of 10 and 3 out of 10 cases, respectively, indicating that peptides 3 and 5 contain important T-cell epitopes.

To identify the ability of the peptides to induce blocking IgG, rabbits were immunized with the 5 individual KLH-peptide conjugates. Subsequently, the ability of peptide-induced rabbit IgG to inhibit the binding of allergic patients' IgE antibodies to rDer p 2 was investigated by ELISA. ELISA plates were coated with 1 μg/ml rDer p 2, washed and blocked. The plates were preincubated with 1:100-diluted rabbit anti-peptide (KLH-P1, KLH-P2, KLH-P3, KLH-P4, and KLH-P5), a rabbit anti rDer p 2 and, for control purposes, with the corresponding preimmune sera. After washing, plates were incubated with human sera from house dust mite allergic, Der p 2 sensitized patients (1:3 diluted) and bound IgE was detected with mouse anti-human IgE (Pharmingen 1:1000) and then with sheep anti-mouse IgG POX-coupled (Amersham Bioscience) 1:2000. The percentage of inhibition of IgE-binding achieved by preincubation with the anti-peptide antisera was calculated as follows: 100−ODi/ODP×100.

TABLE 5

Inhibition capacity of anti-Der p 2- peptide antibodies to inhibit the binding of 20 allergic patients' IgE to complete rDer p 2. Anti-KLH-peptide sera induced by peptides 2, 3, and 4 blocked the IgE-binding to the same extent as sera against wild-type Der p 2. Table 5 shows the inhibition (in %) of all 20 patients.

| Patient # | Peptide 1 | Peptide 2 | Peptide 3 | Peptide 4 | Peptide 5 | Der p 2 |
|---|---|---|---|---|---|---|
| 1 | 50.63 | 74.41 | 78.36 | 75.50 | 1.07 | 78.26 |
| 2 | 49.61 | 77.15 | 82.95 | 77.85 | 4.16 | 82.74 |
| 3 | 64.73 | 87.41 | 92.13 | 89.25 | 0.00 | 93.34 |
| 4 | 37.98 | 72.24 | 81.08 | 75.60 | 2.48 | 84.25 |
| 5 | 0.00 | 43.56 | 50.52 | 47.28 | 0.00 | 56.70 |
| 6 | 54.12 | 80.63 | 82.64 | 80.94 | 1.10 | 83.21 |
| 7 | 51.43 | 79.64 | 92.08 | 83.25 | 16.16 | 93.51 |
| 8 | 42.93 | 71.02 | 79.55 | 75.44 | 0.83 | 78.35 |
| 9 | 30.33 | 58.36 | 50.94 | 56.49 | 7.76 | 57.03 |
| 10 | 38.46 | 66.79 | 71.20 | 71.25 | 0.00 | 69.06 |
| 11 | 48.15 | 74.60 | 83.13 | 78.97 | 5.59 | 83.56 |
| 12 | 46.06 | 68.54 | 74.05 | 71.32 | 10.05 | 76.46 |
| 13 | 44.71 | 73.62 | 87.29 | 77.19 | 4.97 | 84.34 |
| 14 | 39.20 | 63.55 | 63.94 | 65.30 | 0.00 | 66.20 |
| 15 | 43.62 | 71.82 | 89.94 | 74.54 | 0.51 | 94.39 |
| 16 | 38.09 | 69.94 | 84.08 | 72.45 | 1.29 | 86.83 |
| 17 | 43.63 | 74.16 | 87.12 | 78.50 | 2.98 | 89.10 |
| 18 | 29.09 | 73.75 | 89.97 | 77.59 | 1.38 | 90.66 |
| 19 | 40.44 | 56.77 | 62.09 | 62.30 | 0.00 | 66.16 |
| 20 | 20.89 | 60.85 | 70.76 | 63.16 | 2.69 | 74.98 |
| mean | 40.71 | 69.94 | 77.69 | 72.71 | 3.15 | 79.46 |

TABLE 6

Decision matrix for selection of peptides. Peptides 2 and 4 meet all requirements of peptide fragments of the present invention.

| | peptide is non-IgE binding | peptide induces no or only low T-cell reactivity | peptide induces IgG which inhibit binding of human IgE to Der p 2 | Peptide suitable? |
|---|---|---|---|---|
| Der p2 Pep1 | ✓ | ✓ | X | no |
| Der p2 Pep2 | ✓ | ✓ | ✓ | yes |
| Der p2 Pep3 | ✓ | X | ✓ | no |
| Der p2 Pep4 | ✓ | ✓ | ✓ | yes |
| Der p2 Pep5 | ✓ | X | X | no |

Example 27

Selection of Der p 1 Derived Hypoallergenic Peptides

The ability of Der p 1 derived peptides to induce IgE-blocking IgG antibodies was determined using rabbit-anti-peptide KLH antisera and sera from 6 house dust mite allergic patients in an inhibition ELISA as described in example 26 with the exception that the ELISA plates were coated with wild-type Der p 1 instead of Der p 2.

TABLE 7

Inhibition capacity of anti-Der p 1- peptide antibodies to inhibit the binding of 6 allergic patients' IgE to complete Der p 1. Anti-KLH-peptide sera induced by peptides 1, 2, and 8 were found to block the IgE-binding to a similar extent as sera against wild-type Der p 1. Table 7 shows the inhibition (in %) of 6 patients.

| | Patient I | Patient II | Patient III | Patient IV | Patient V | Patient VI | mean |
|---|---|---|---|---|---|---|---|
| Der p 1 | 72.9 | 91.3 | 80 | 90.8 | 87.5 | 89.7 | 85.4 |
| peptide 1 | 50 | 68.4 | 65.5 | 87.7 | 77.4 | 85.1 | 72.4 |
| peptide 2 | 47.8 | 73.4 | 66.1 | 83.2 | 72.6 | 82.5 | 70.9 |
| peptide 3 | 22.5 | 28.2 | 22.1 | 35.5 | 26.4 | 27.6 | 27.1 |
| peptide 4 | 24.4 | 42.4 | 33.4 | 46.5 | 33.2 | 42 | 37.0 |
| peptide 5 | 22.7 | 31.4 | 23.3 | 38.4 | 30.4 | 31.5 | 29.6 |
| peptide 6 | 1.9 | 12.8 | 3.6 | 5.6 | 4.2 | 5.4 | 5.6 |
| peptide 7 | 30 | 51.8 | 43.5 | 67.4 | 52.1 | 59.6 | 50.7 |
| peptide 8 | 41.1 | 65.8 | 52.8 | 76 | 66.2 | 73.9 | 62.6 |

The invention claimed is:

1. A polypeptide comprising an amino acid sequence selected from the group consisting of SEQ ID No. 14, SEQ ID No. 15, SEQ ID No. 16, SEQ ID No. 17, SEQ ID No. 18, SEQ ID No. 19, SEQ ID No. 20, SEQ ID No. 149, SEQ ID No. 150, SEQ ID No. 151 and SEQ ID No. 152.

2. A composition comprising the polypeptide according to claim 1 and at least one of an adjuvant, a pharmaceutically acceptable excipient and a preservative.

3. A method f treating an allergy in a human or an animal in need thereof, comprising administering the polypeptide of claim 1 to the human or an animal.

4. A method of treating an allergy in a human or an animal in need thereof, comprising administering the composition of claim 2 and wherein the composition comprises a mixture of more than one polypeptide.

5. The polypeptide of claim 1, comprising SEQ ID No. 14.
6. The polypeptide of claim 1, comprising SEQ ID No. 15.
7. The polypeptide of claim 1, comprising SEQ ID No. 16.
8. The polypeptide of claim 1, comprising SEQ ID No. 17.
9. The polypeptide of claim 1, comprising SEQ ID No. 18.
10. The polypeptide of claim 1, comprising SEQ ID No. 19.
11. The polypeptide of claim 1, comprising SEQ ID No. 20.
12. The polypeptide of claim 1, comprising SEQ ID No. 149.
13. The polypeptide of claim 1, comprising SEQ ID No. 150.
14. The polypeptide of claim 1, comprising SEQ ID No. 151.
15. The polypeptide of claim 1, comprising SEQ ID No. 152.
16. The composition of claim 2, comprising SEQ ID No. 14, SEQ ID No. 15, SEQ ID No. 16, and SEQ ID No. 17.
17. The method of claim 4, wherein the composition comprises SEQ ID No. 14, SEQ ID No. 15, SEQ ID No. 16, and SEQ ID No. 17.

* * * * *